(12) United States Patent
Selbo et al.

US009737610B2

(10) Patent No.: US 9,737,610 B2
(45) Date of Patent: Aug. 22, 2017

(54) FORMULATIONS OF RIFAXIMIN AND USES THEREOF

(71) Applicants: Jon Selbo, West Lafayette, IN (US); Jing Teng, West Lafayette, IN (US); Mohammed A. Kabir, Cary, NC (US); Pam Golden, Durham, NC (US)

(72) Inventors: Jon Selbo, West Lafayette, IN (US); Jing Teng, West Lafayette, IN (US); Mohammed A. Kabir, Cary, NC (US); Pam Golden, Durham, NC (US)

(73) Assignee: Salix Pharmaceuticals, Ltd, Bridgewater, NJ (US)

( * ) Notice: Subject to any disclaimer, the term of this patent is extended or adjusted under 35 U.S.C. 154(b) by 0 days.

(21) Appl. No.: 14/250,293

(22) Filed: Apr. 10, 2014

(65) Prior Publication Data

US 2015/0133482 A1 May 14, 2015

Related U.S. Application Data

(63) Continuation of application No. 13/181,481, filed on Jul. 12, 2011, now abandoned.

(60) Provisional application No. 61/363,609, filed on Jul. 12, 2010, provisional application No. 61/419,056, filed on Dec. 2, 2010.

(51) Int. Cl.
*A61K 47/38* (2006.01)
*A61K 9/10* (2006.01)
*A61K 9/20* (2006.01)
*A61K 31/437* (2006.01)
*C07D 498/22* (2006.01)
*A61K 9/14* (2006.01)
*A61K 9/16* (2006.01)
*A61K 9/48* (2006.01)
*A61K 47/32* (2006.01)

(52) U.S. Cl.
CPC ............... *A61K 47/38* (2013.01); *A61K 9/10* (2013.01); *A61K 9/146* (2013.01); *A61K 9/1641* (2013.01); *A61K 9/1652* (2013.01); *A61K 9/2027* (2013.01); *A61K 9/2054* (2013.01); *A61K 9/4858* (2013.01); *A61K 9/4866* (2013.01); *A61K 31/437* (2013.01); *A61K 47/32* (2013.01); *C07D 498/22* (2013.01)

(58) Field of Classification Search
None
See application file for complete search history.

(56) References Cited

U.S. PATENT DOCUMENTS

2005/0101598 A1* 5/2005 Viscomi ............... C07D 498/22
514/224.5
2007/0141143 A1* 6/2007 Smithey ............... A61K 9/1635
424/464
2008/0095754 A1 4/2008 Burke et al.
2009/0011020 A1 1/2009 Viscomi et al.
2009/0011024 A1* 1/2009 Babcock ................ A61K 9/146
424/485
2009/0028940 A1* 1/2009 Jahagirdar ........... A61K 9/1623
424/468
2010/0174064 A1 7/2010 Gushurst et al.

FOREIGN PATENT DOCUMENTS

| DE | WO2009118167 | * 10/2009 |
|---|---|---|
| EP | 2011486 A1 | 1/2009 |
| MX | 2012/004954 A | 9/2012 |
| WO | WO-02051385 A1 | 7/2002 |
| WO | 2006026500 A1 | 3/2006 |
| WO | 2006094737 A2 | 9/2006 |
| WO | WO-2009108730 A2 | 9/2009 |
| WO | WO-2010067072 A1 | 6/2010 |
| WO | 2011061748 A1 | 5/2011 |
| WO | WO-2011051971 A2 | 5/2011 |
| WO | WO-2011061748 A1 | 5/2011 |

OTHER PUBLICATIONS

Leuner et al. (European Journal of Pharmaceutics and Biopharmaceutics 50, 47-60, 2000) Improving drug solubility ....*
Leuner, et al., "Improve Drug Solubility for Oral Delivery using Solid Dispersions," European Journal of Pharmaceutics and Biopharmaceutics, vol. 50, No. 1, pp. 47-60, Jul. 3, 2000.
Hancock, et al., "Characteristics and Significance of Amorphous State in Pharmaceutical Systems," Journal of Pharmaceutical Sciences, vol. 86, No. 1, pp. 1-8, Jan. 1997.
Buhler, "Polyvinylpyrrolidone Excipients for Pharmaceuticals," Povidone, Crospovidone and Copovidone, Springer, Chapter 2, Section 2.4.3, pp. 83-98, 2005.
Vasconcelos et al., "Solid dispersions as strategy to improve oral bioavailability of poor water soluble drugs", *Drug Discovery Today*, 12(23/24):1068-1075, 2007.
Van den Mooter, "Solid Dispersions as a Formulation Strategy for Poorly Soluble Compounds," 20th Annual Symposium of the Finish Society of Physical Pharmacy; Vithi, Finland; Katholieke Universiteit Leuven; 37 pages; Jan. 28-29, 2009.
Martins, et al., "Microstructured Ternary Solid Dispersions to Improve Carbamazepine Solubility," Powder Technology, 215-216, (2012), 156-165.
"EUDRAGIT® Acrylic Drug Delivery Polymers" [retrieved from internet on Jan. 29, 2016]. <URL: <http://eudragit.evonik.com/product/eudragit/en/products-services/eudragit-products/pages/default.aspx>> published on Apr. 23, 2010 as per Wayback Machine.

* cited by examiner

*Primary Examiner* — Tigabu Kassa
(74) *Attorney, Agent, or Firm* — McCarter & English, LLP; Jonathan M. Sparks; Michael J. DeGrazia

(57) ABSTRACT

The present invention relates to new rifaximin forms comprising solid dispersions of rifaximin, methods of making same and to their use in medicinal preparations and therapeutic methods.

15 Claims, 88 Drawing Sheets

Figure 1. Chemical structure of Rifaximin

Overlay of XRPD patterns for Rifaximin/PVP K-90 dispersions obtained from methanol by spray drying.

Top to bottom: 25:75 (w/w) Rifaximin/PVP K-90
50:75 (w/w) Rifaximin/PVP K-90
75:25 (w/w) Rifaximin/PVP K-90
Crystalline Rifaximin as-received Figure 3. mDSC thermogram for 25:75 (w/w) Rifaximin/PVP K-90 dispersion obtained from methanol by spray drying

Figure 4. mDSC thermogram for 50:50 (w/w) Rifaximin/PVP K-90 dispersion obtained from methanol by spray drying

Figure 5. mDSC thermogram for 75:25 (w/w) Rifaximin/PVP K-90 dispersion obtained from methanol by spray drying Figure 6. Overlay of mDSC thermogram for Rifaximin/PVP K-90 dispersions obtained from methanol by spray drying.

Top to bottom: 25:75 (w/w) Rifaximin/PVP K-90
50:75 (w/w) Rifaximin/PVP K-90
75:25 (w/w) Rifaximin/PVP K-90

Overlay of XRPD patterns for Rifaximin/HPMC-P dispersions obtained from methanol by spray drying.

Top to bottom: 25:75 (w/w) Rifaximin/HPMC-P
50:75 (w/w) Rifaximin/HPMC-P
75:25 (w/w) Rifaximin/HPMC-P
Crystalline Rifaximin as-received

Figure 8. mDSC thermogram for 25:75 (w/w) Rifaximin/HPMC-P dispersion obtained from methanol by spray drying

Figure 9. mDSC thermogram for 50:50 (w/w) Rifaximin/HPMC-P dispersion obtained from methanol by spray drying Figure 10. mDSC thermogram for 75:25 (w/w) Rifaximin/HPMC-P dispersion obtained from methanol by spray drying

Figure 11. Overlay of mDSC thermogram for Rifaximin/HPMC-P dispersions obtained from methanol by spray drying.

Top to bottom: 25:75 (w/w) Rifaximin/HPMC-P
                  50:75 (w/w) Rifaximin/HPMC-P
                  75:25 (w/w) Rifaximin/HPMC-P Figure 12. Overlay of XRPD patterns for Rifaximin/HPMC-AS HG dispersions obtained from methanol by spray drying.

Top to bottom: 25:75 (w/w) Rifaximin/HPMC-AS HG
50:75 (w/w) Rifaximin/HPMC-AS HG
75:25 (w/w) Rifaximin/HPMC-AS HG
Crystalline Rifaximin as-received Figure 13. mDSC thermogram for 25:75 (w/w) Rifaximin/HPMC-AS HG dispersion obtained from methanol by spray drying

Figure 14. mDSC thermogram for 50:50 (w/w) Rifaximin/HPMC-AS HG dispersion obtained from methanol by spray drying

Figure 15. mDSC thermogram for 75:25 (w/w) Rifaximin/HPMC-AS HG dispersion obtained from methanol by spray drying

Figure 16. Overlay of mDSC thermogram for Rifaximin/HPMC-AS HG dispersions obtained from methanol by spray drying.

Top to bottom: 25:75 (w/w) Rifaximin/HPMC-AS HG
50:75 (w/w) Rifaximin/HPMC-AS HG
75:25 (w/w) Rifaximin/HPMC-AS HG Figure 17. Overlay of XRPD patterns for Rifaximin/HPMC-AS MG dispersions obtained from methanol by spray drying Top to bottom: 25:75 (w/w) Rifaximin/HPMC-AS MG
50:75 (w/w) Rifaximin/HPMC-AS MG
75:25 (w/w) Rifaximin/HPMC-AS MG
Crystalline Rifaximin as-received Figure 18. mDSC thermogram for 25:75 (w/w) Rifaximin/HPMC-AS MG dispersion obtained from methanol by spray drying

Figure 19. mDSC thermogram for 50:50 (w/w) Rifaximin/HPMC-AS MG dispersion obtained from methanol by spray drying

Figure 20. mDSC thermogram for 75:25 (w/w) Rifaximin/HPMC-AS MG dispersion obtained from methanol by spray drying

Figure 21. Overlay of mDSC thermogram for Rifaximin/HPMC-AS MG dispersions obtained from methanol by spray drying.

Top to bottom: 25:75 (w/w) Rifaximin/HPMC-AS MG
50:75 (w/w) Rifaximin/HPMC-AS MG
75:25 (w/w) Rifaximin/HPMC-AS MG Overlay of XRPD patterns for Rifaximin/Eudragit L100-55 dispersions obtained from methanol by spray drying.

Top to bottom: 25:75 (w/w) Rifaximin/Eudragit L100-55
50:75 (w/w) Rifaximin/Eudragit L100-55
75:25 (w/w) Rifaximin/Eudragit L100-55
Crystalline Rifaximin as-received

Figure 23. mDSC thermogram for 25:75 (w/w) Rifaximin/Eudragit L100-55 dispersion obtained from methanol by spray drying

Figure 24. mDSC thermogram for 50:50 (w/w) Rifaximin/Eudragit L100-55 dispersion obtained from methanol by spray drying

Figure 25. mDSC thermogram for 75:25 (w/w) Rifaximin/Eudragit L100-55 dispersion obtained from methanol by spray drying

Figure 26. Overlay of mDSC thermogram for Rifaximin/Eudragit L100-55 dispersions obtained from methanol by spray drying

Top to bottom: 25:75 (w/w) Rifaximin/Eudragit L100-55
                50:75 (w/w) Rifaximin/Eudragit L100-55
                75:25 (w/w) Rifaximin/Eudragit L100-55

Figure 27. mDSC thergram for 25:75 (w/w) Rifaximin/HPMC-P dispersion stressed at 40 °C/75% RH for 7 d

Figure 28. mDSC thergram for 75:25 (w/w) Rifaximin/HPMC-AS HG dispersion stressed at 40 °C/75% RH for 7 d

Figure 29. mDSC thergram for 75:25 (w/w) Rifaximin/HPMC-AS MG dispersion stressed at 40 °C/75% RH for 7 d

Figure 30. mDSC thergram for 25:75 (w/w) Rifaximin/Eudragit L100-55 dispersion stressed at 40 °C/75% RH for 7 d Figure 31. XRPD pattern for 50:50 (w/w) Rifaximin/HPMC-AS MG dispersion top: 50:50 (w/w) Rifaximin/HPMC-AS MG
bottom: Crystalline Rifaximin as-received Figure 32. Modulate DSC thermograms for 50:50 (w/w) Rifaximin/HPMC-AS MG dispersion

Figure 33. TG-IR analysis for 50:50 (w/w) Rifaximin/HPMC-AS MG dispersion – TGA data

TG-IR analysis for 50:50 (w/w) Rifaximin/HPMC-AS MG dispersion—Gram-Schmidt plot and waterfall plot

Figure 36. XRPD pattern for 25:75 (w/w) Rifaximin/HPMC-P dispersion top: 25:75 (w/w) Rifaximin/HPMC-P
bottom: Crystalline Rifaximin as-received

Figure 37. Modulate DSC thermograms for 25:75 (w/w) Rifaximin/HPMC-P dispersion

Figure 38. TG-IR analysis for 25:75 (w/w) Rifaximin/HPMC-P dispersion – TGA data Figure 41. Overlay of pre-processed XRPD patterns in multivariate mixture analysis.

Figure 42. Estimated Concentrations of Rifaximin (blue) and HPMC-AS MG (red) using Unscrambler MCR analysis.

Figure 43. Estimated XRPD patterns of Rifaximin (blue) and HPMC-AS MG (red) using Unscrambler MCR analysis

Figure 44. Overlay of estimated XRPD pattern of pure rifaximin using MCR and measured XRPD pattern of 100% rifaximin

Figure 45. Overlay of estimated XRPD pattern of pure HPMC-AS MG using MCR and measured XRPD pattern of 100% HPMC-AS MG.

XRPD pattern for combined solids of Rifaximin/HPMC-AS MG/Pluronic ternary dispersion from scale-up attempts Modulate DSC thermogram for combined solids of Rifaximin/HPMC-AS MG/Pluronic ternary dispersion TG-IR analysis for combined solids of Rifaximin/HPMC-AS MG/Pluronic
ternary dispersion from scale-up attempts – TGA thermogram Overlay of IR spectra for X-ray amorphous Rifaximin and combined solids of Rifaximin/HPMC-AS MG/Pluronic ternary dispersion.

top: X-ray amorphous Rifaximin
bottom: Rifaximin/HPMC-AS MG/Pluronic ternary dispersion Overlay of Ramam spectra for X-ray amorphous Rifaximin and combined solids of Rifaximin/HPMC-AS MG/Pluronic ternary dispersion.

top: X-ray amorphous Rifaximin
bottom: Rifaximin/HPMC-AS MG/Pluronic ternary dispersion Particle size analysis report for combined solids of Rifaximin/HPMC-AS MG/Pluronic ternary dispersion from scale-up attempts Dynamic vapor sorption (DVS) analysis for combined solids of Rifaximin/HPMC-AS MG/Pluronic ternary dispersion Overlay of XRPD patterns for Rifaximin/HPMC-AS MG/Pluronic ternary dispersion post-DVS solids and solids as-prepared top: post-DVS solids of Rifaximin/HPMC-AS MG/Pluronic ternary dispersion
bottom: Rifaximin/HPMC-AS MG/Pluronic ternary dispersion as-prepared

FIG. 55

Overlay of XRPD patterns for Rifaximin ternary dispersion post-stressed samples and as-prepared sample top: Rifaximin ternary dispersion after stressed at 40 °C/75%RH for 12 weeks
second: Rifaximin ternary dispersion after stressed at 40 °C/75%RH for 6 weeks
third: Rifaximin ternary dispersion after stressed at 70 °C/75%RH for 3 weeks
fourth: Rifaximin ternary dispersion after stressed at 70 °C/75%RH for 1 week
bottom: Rifaximin ternary dispersion as-prepared

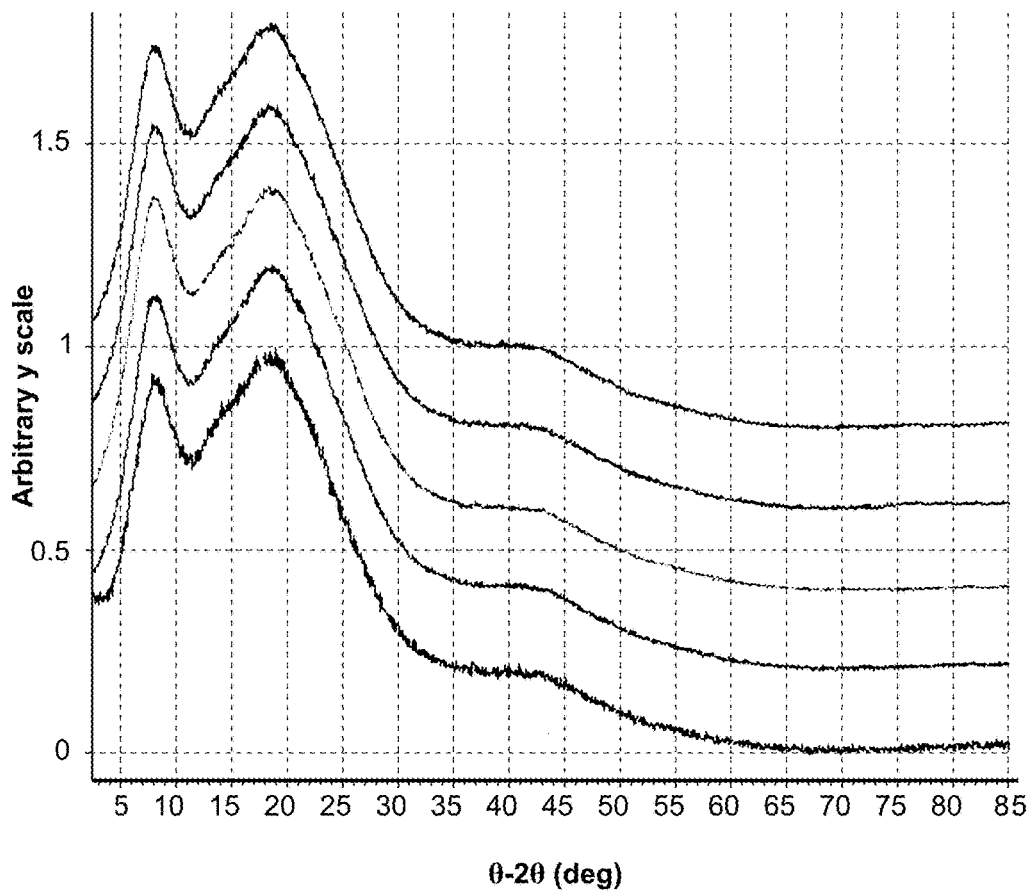

mDSC thermgram for Rifaximin ternary dispersion after 70 °C/75% RH 1week mDSC thermgram for Rifaximin ternary dispersion after 70 °C/75% RH 3weeks mDSC thermgram for Rifaximin ternary dispersion after 40 °C/75% RH 12 weeks

HPMC-AS mDSC thermogram of rifaximin quaternary sample containing 0.063 wt% BHA mDSC thermogram of rifaximin quaternary sample containing 0.063 wt% BHT mDSC thermogram of rifaximin quaternary sample containing 0.094 wt% PG Rifaximin Next generation: non-clinical data Rifaximin SDD in dogs

| SDD dose (mg) | Dose Multiple | $T_{1/2}$ (h) | $T_{max}$ (h) | $C_{max}$ (ng/mL) | Cmax multiple | $AUC_{0-24}$ (ng.h/mL) | AUC Multiple |
|---|---|---|---|---|---|---|---|
| 150 | 1 | 6.1 | 1 | 35.2 | 1 | 95.2 | 1 |
| 275 | 1.8 | 7 | 1.5 | 59 | 1.7 | 169.1 | 1.8 |
| 550 | 3.7 | 5.1 | 0.75 | 80.9 | 2.3 | 200.0 | 2.1 |
| 1100 | 7.3 | 4.3 | 1.5 | 431 | 12.2 | 983.7 | 10.3 |
| 2200 | 14.7 | 5.3 | 2 | 700 | 19.9 | 2165.8 | 22.75 |

Figure 80

Part A dose escalation/dose selection

- N = 10 male subjects
- 3 ascending single doses (SDD powder in capsule)
  - 75, 250, 550 mg planned
- Plasma PK samples collected for 24 h
- Urine and feces collected in total for 24 h
- ~7 day washout between doses
- Safety, tolerability, and plasma PK data reviewed at each decision point for next dose selection Example SDD dose escalation: Subject 001

| Dose | Dose multiple | $T_{1/2}$ (h) | $T_{max}$ (h) | $C_{max}$ (ng/mL) | $C_{max}$ multiple | $AUC_{0-24}$ (ng.h/mL) | $AUC_{0-24}$ multiple |
|---|---|---|---|---|---|---|---|
| 75 MG IR | 1 | 15.7 | 0.5 | 4.1 | 1.0 | 11.2 | 1.0 |
| 250 MG IR | 3.3 | 7.6 | 0.5 | 8.2 | 2.0 | 21.7 | 1.9 |
| 550 MG IR | 7.3 | 10.6 | 1 | 23.1 | 5.7 | 66.4 | 5.9 |

Example SDD dose escalation: Subject 006

| Dose | Dose multiple | $T_{1/2}$ (h) | $T_{max}$ (h) | $C_{max}$ (ng/mL) | $C_{max}$ multiple | $AUC_{0-24}$ (ng.h/mL) | $AUC_{0-24}$ multiple |
|---|---|---|---|---|---|---|---|
| 75 MG IR | 1 | 5.1 | 1.5 | 8.4 | 1 | 24.7 | 1 |
| 250 MG IR | 3.3 | 7.6 | 1 | 22.0 | 2.6 | 67.2 | 2.7 |
| 550 MG IR | 7.3 | 10.2 | 3 | 58.8 | 7 | 234.1 | 9.5 |

Dose escalation mean data (linear scale)

Dose escalation mean data (log scale)

Rifaximin SDD dose escalation summary

| Mean Pk parameters Dose | Dose multiple | $T_{1/2}$* (h) | $T_{max}$** (h) | $C_{max}$ (ng/mL) | $C_{max}$ multiple | $AUC_{0-24}$ (ng.h/mL) | $AUC_{0-24}$ multiple | % of dose in urine (0-24h) |
|---|---|---|---|---|---|---|---|---|
| 75 MG IR | 1 | 9.2 | 1.25 | 4.8 | 1 | 16.1 | 1 | 0.21 |
| 150 MG IR | 2 | 9.2 | 2.5 | 12.5 | 2.6 | 47.6 | 3.0 | - |
| 250 MG IR | 3.3 | 12.8 | 1 | 19.9 | 4.1 | 62.9 | 3.9 | 0.18 |
| 550 MG IR | 7.3 | 12.9 | 1 | 25.5 | 5.3 | 98.7 | 6.1 | 0.13 |

Figure 86
Dose/ dosage form comparison

Mean PK parameters:

| Formulation and conditions | Dose | $T_{1/2}^*$ (h) | $T_{max}^{**}$ (h) | $C_{max}$ (ng/mL) | $AUC_{0-24}$ (ng.h/mL) |
|---|---|---|---|---|---|
| SDD in gelatin capsules, healthy | 75 MG | 9.2 | 1.25 | 4.8 | 16.1 |
| | 150 MG | 9.2 | 2.5 | 12.5 | 47.6 |
| | 250 MG | 12.8 | 1 | 19.9 | 62.9 |
| | 550 MG | 12.9 | 1 | 25.5 | 98.7 |
| Marketed tablet, healthy (RFPK1007) | 550 MG | 1.8 | 0.75 | 4.0 | 11.1* |
| Marketed tablet, IBS | 550 MG | 3.1 | 0.775 | 3.5 | 9.7§ |
| Marketed tablet, C-P A | 550 MG | 8.1 | 1 | 19.5 | 118§ |
| Marketed tablet, C-P B | 550 MG | 10.5 | 1 | 25.1 | 161§ |
| Marketed tablet, C-P C | 550 MG | 6.6 | 1 | 35.5 | 246§ |

*Geometric mean; **Median; §AUC(0-12h); *AUC(0-∞)

Figure 87
Dose/ dosage form comparison

Mean PK parameters: 6.4-fold difference in $C_{max}$  ~8.9-fold difference in AUC

| Formulation and conditions | Dose (mg) | $T_{1/2}$* (h) | $T_{max}$** (h) | $C_{max}$ (ng/mL) | $AUC_{0-24}$ (ng.h/mL) |
|---|---|---|---|---|---|
| SDD in gelatin capsules, healthy | 75 | 9.2 | 1.25 | 4.8 | 16.1 |
| | 150 | 9.2 | 2.5 | 12.5 | 47.6 |
| | 250 | 12.8 | 1 | 19.9 | 62.9 |
| | 550 | 12.9 | 1 | 25.5 | 98.7 |
| Marketed tablet, healthy (RFPK1007) | 550 | 1.8 | 0.75 | 4.0 | 11.1# |
| Marketed tablet, IBS | 550 | 3.1 | 0.775 | 3.5 | 9.7§ |
| Marketed tablet, C-P A | 550 | 8.1 | 1 | 19.5 | 118§ |
| Marketed tablet, C-P B | 550 | 10.5 | 1 | 25.1 | 161§ |
| Marketed tablet, C-P C | 550 | 6.6 | 1 | 35.5 | 246§ |

*Geometric mean; **Median; §AUC(0-12h); #AUC(0-∞)

FORMULATIONS OF RIFAXIMIN AND USES THEREOF

RELATED APPLICATIONS

This application is a continuation of U.S. patent application Ser. No. 13/181,481 filed 12 Jul. 2011 which claims the benefit of U.S. Provisional Application No. 61/363,609 filed 12 Jul. 2010, and U.S. Provisional Application No. 61/419,056, filed 2 Dec. 2010, the entire contents of each of which are hereby incorporated herein by reference.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and pancreatic insufficiency among other diseases. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res*, 14 (2), 51-56, (1994)).

Rifaximin is described in Italian Patent IT 1154655 and EP 0161534, both of which are incorporated herein by reference in their entirety for all purposes. EP 0161534 discloses a process for rifaximin production using rifamycin O as the starting material (The Merck Index, XIII Ed., 8301). U.S. Pat. No. 7,045,620 B1 and PCT Publication WO 2006/094662 A1 disclose polymorphic forms of rifaximin. There is a need in the art for formulations of rifaximin to better treat gastrointestinal and other diseases.

SUMMARY

Provided herein are solid dispersion forms of rifaximin with a variety of polymers and polymer concentrations.

In one aspect, provided herein are forms solid dispersion of rifaximin.

In one embodiment, the form solid dispersion of rifaximin is characterized by an XRPD substantially similar to one or more of the XRPDs of FIGS. 2, 7, 12, 17, 22, 31, and 36.

In one embodiment, the form solid dispersion of rifaximin is characterized by a Thermogram substantially similar to FIGS. 3-6, 8-11, 13-16, 18-21, 23-26, 27-30, and 32.

In one embodiment, the form has the appearance of a single glass transition temperature (Tg).

In one embodiment, a Tg of a form increases with an increased rifaximin concentration In one embodiment, a form stressed at 70° C./75% RH for 1 week, solids are still x-ray amorphous according to XRPD.

In one embodiment, a form stressed at 70° C./75% RH for 3 weeks, solids are still x-ray amorphous according to XRPD.

In one embodiment, a form stressed at 70° C./75% RH for 6 weeks, solids are still x-ray amorphous according to XRPD.

In one embodiment, a form stressed at 70° C./75% RH for 12 weeks, solids are still x-ray amorphous according to XRPD.

In one aspect, provided herein are microgranules comprising one or more of the solid dispersion forms of rifaximin described herein.

In one embodiment, the microgranules further comprise a polymer.

In one embodiment, the polymer comprises one or more of polyvinylpyrrolidone (PVP) grade K-90, hydroxypropyl methylcellulose phthalate (HPMC-P) grade 55, hydroxypropyl methylcellulose acetate succinate (HPMC-AS) grades HG and MG, or a polymethacrylate (Eudragit® L100-55).

In specific embodiments, the microgranules comprises 25-75% polymer, 40-60% polymer, or 40-50% polymer. In an exemplary embodiment, the microgranules comprises 42-44% polymer.

In one embodiment, the microgranules comprise equal amounts of rifaximin and polymer.

In another embodiment, the microgranules further comprising an intragranular release controlling agent. In exemplary embodiments, the intragranular release controlling agent comprises a pharmaceutically acceptable excipient, disintegrant, crosprovidone, sodium starch glycolate, corn starch, microcrystalline cellulose, cellulosic derivatives, sodium bicarbonate, and sodium alginate.

In one embodiment, the intragranular release controlling agent comprises between about 2 wt % to about 40 wt % of the microgranule, about 5 wt % to about 20 wt % of the microgranule, or about 10 wt % of the microgranule.

In another embodiment, the intragranular release controlling agent comprises a pharmaceutically acceptable disintegrant, e.g., one selected from the group consisting of crosprovidone, sodium starch glycolate, corn starch, microcrystalline cellulose, cellulosic derivatives, sodium bicarbonate, and sodium alginate.

In another embodiment, the microgranules further comprise a wetting agent or surfactant, e.g., a non-ionic surfactant.

In one embodiment, the non-ionic surfactant comprises between about 2 wt % to about 10 wt % of the microgranule, between about 4 wt % to about 8 wt % of the microgranule, or about 5.0 wt % of the microgranule.

In one embodiment, the non-ionic surfactant comprises a poloxamer, e.g., poloxamer 407 also known as Pluronic F-127.

In another embodiment, the microgranules further comprise an antioxidant.

In exemplary embodiments, the antioxidant is butylated hydroxyanisole (BHA), butylated hydroxytoluene (BHT) or propyl gallate (PG).

In another embodiment, the antioxidant comprises between about 0.1 wt % to about 3 wt % of the microgranule or between about 0.5 wt % to about 1 wt % of the microgranule.

In another aspect, provided herein are pharmaceutical compositions comprising the microgranules described herein.

In one embodiment, the pharmaceutical compositions further comprise one or more pharmaceutically acceptable excepients.

In one embodiment, the pharmaceutical compositions are tablets or capsules.

In one embodiment, the pharmaceutical compositions comprises a disintegrant.

In one embodiment, the polymer comprises one or more of polyvinylpyrrolidone (PVP) grade K-90, hydroxypropyl methylcellulose phthalate (HPMC-P) grade 55, hydroxypropyl methylcellulose acetate succinate (HPMC-AS) grades HG and MG, or a polymethacrylate (Eudragit® L100-55).

In one aspect, provided herein are pharmaceutical solid dispersion formulations comprising: rifaximin, HPMC-AS, at a rifaximin to polymer ratio of 50:50, a non-ionic, surfactant polyol and a intragranular release controlling agent.

In one embodiment, the intragranular release controlling agent comprises about 10 wt % of the formulation.

In one aspect, provided herein are processes for producing a solid dispersion of rifaximin comprising: making a slurry of methanol, rifaximin, a polymer and a surfactant; spray drying the slurry; and blending the spray dried slurry with a intragranular release controlling agent.

In one aspect, provided herein are processes for producing a solid dispersion of rifaximin comprising: making a slurry of methanol, rifaximin, HPMC-AS MG and Pluronic F-127; spray drying the slurry; and blending the spray dried slurry with a intragranular release controlling agent.

In one embodiment, the intragranular release controlling agent comprises croscarmellose sodium.

A process for producing form solid dispersion of rifaximin comprising one or more of the methods listed in Tables 1-5.

In one embodiment, pharmaceutical compositions comprising SD rifaximin, a polymer, a surfactant, and a release controlling agent are provided. In one embodiment, provided are pharmaceutical compositions comprising SD rifaximin, HPMC-AS, pluronic F127, and croscarmellose Na (CS). In one embodiment, the pharmaceutical compositions are tablets or pills.

In additional embodiments, the pharmaceutical compositions further comprise fillers, glidants or lubricants.

In specific embodiments, the pharmaceutical compositions comprise the ratios of components set forth in Table 37.

Other embodiment and aspects are disclosed infra.

BRIEF DESCRIPTION OF THE DRAWINGS

FIG. 55. An exemplary overlay of XRPD patterns for Rifaximin ternary dispersion post-stressed samples and as-prepared sample.

FIG. 64. Rifaximin spray dried dispersion (SDD) capsule dissolution.

FIG. 65. Rifamixin SDD with 10% CS formulation.

FIG. 66. Rifaximin SDD with 10% CS formulation. Rifaxamin SDD capsules dissolution.

FIG. 68. Effects of media pH on dissolution.

FIG. 69. Effects of media pH on dissolution.

FIG. 70. Effects of media pH on dissolution.

FIG. 80 summarizes the dose escalation/regional absorption study, part A dose escalation/dose selection.

FIG. 86 is a Table of dose/dosage form comparison.

FIG. 87 is a Table of dose/dosage form comparison. This table compares SDD at increasing doses to the current crystalline formulation in terms of systemic PK.

DETAILED DESCRIPTION

Figure 1:
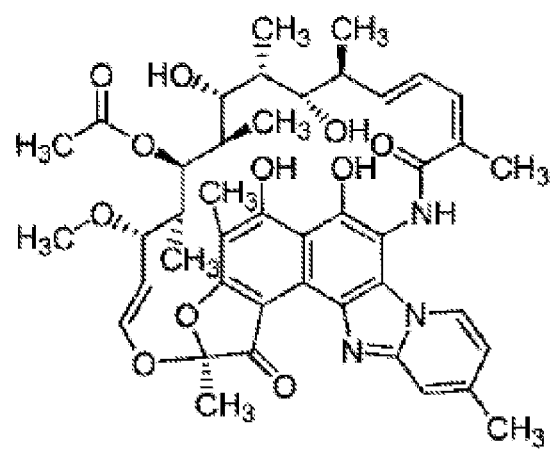
FIG. 1. Chemical structure of Rifaximin.
Figure 2:
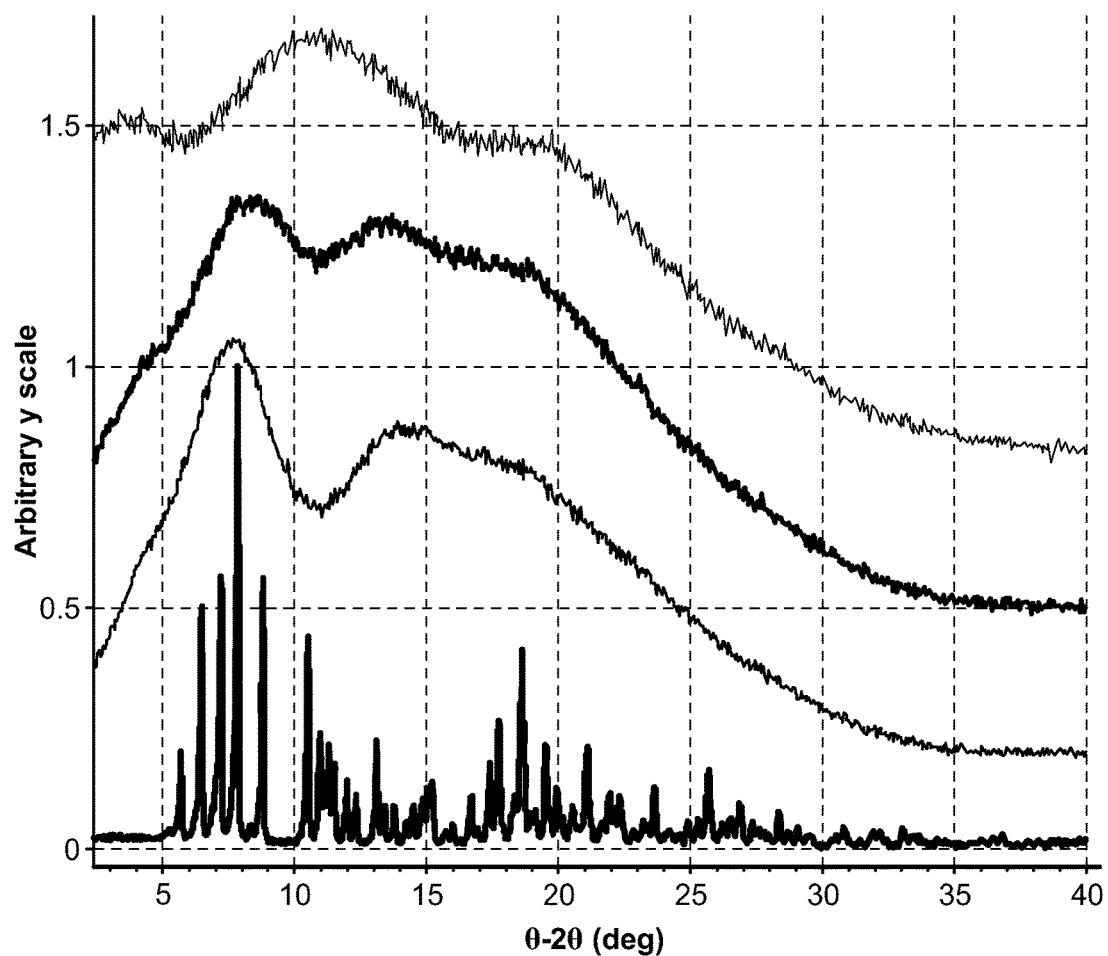
FIG. 2. Overlay of XRPD patterns for Rifaximin/PVP K-90 dispersions obtained from methanol by spray drying.
Figure 3:
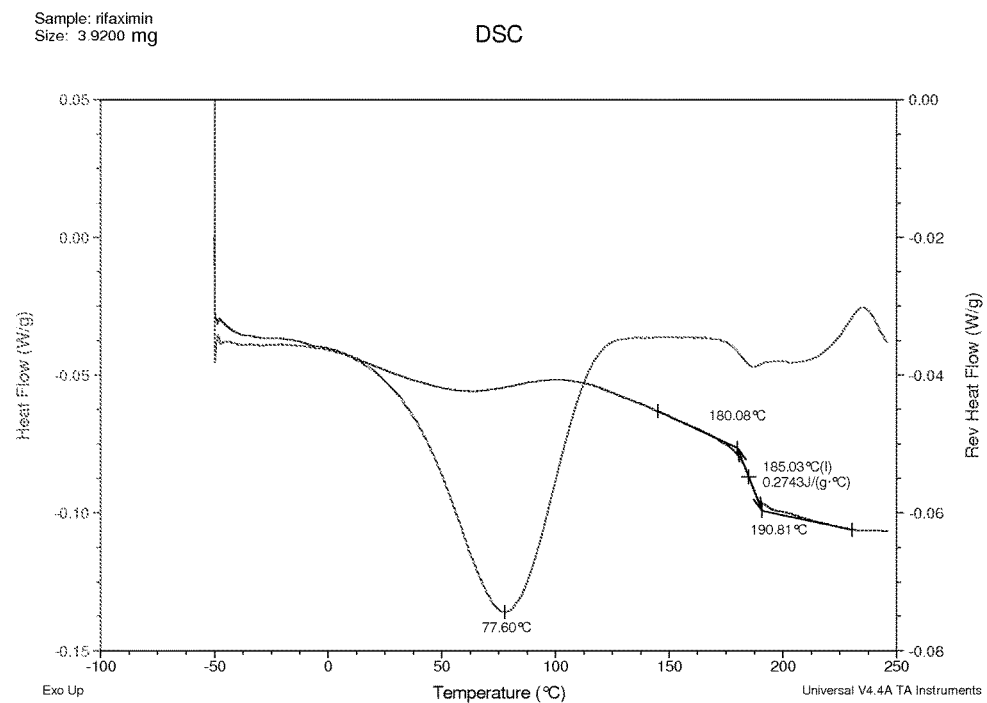
FIG. 3. mDSC thermogram for 25:75 (w/w) Rifaximin/PVP K-90 dispersion obtained from methanol by spray drying.
Figure 4:
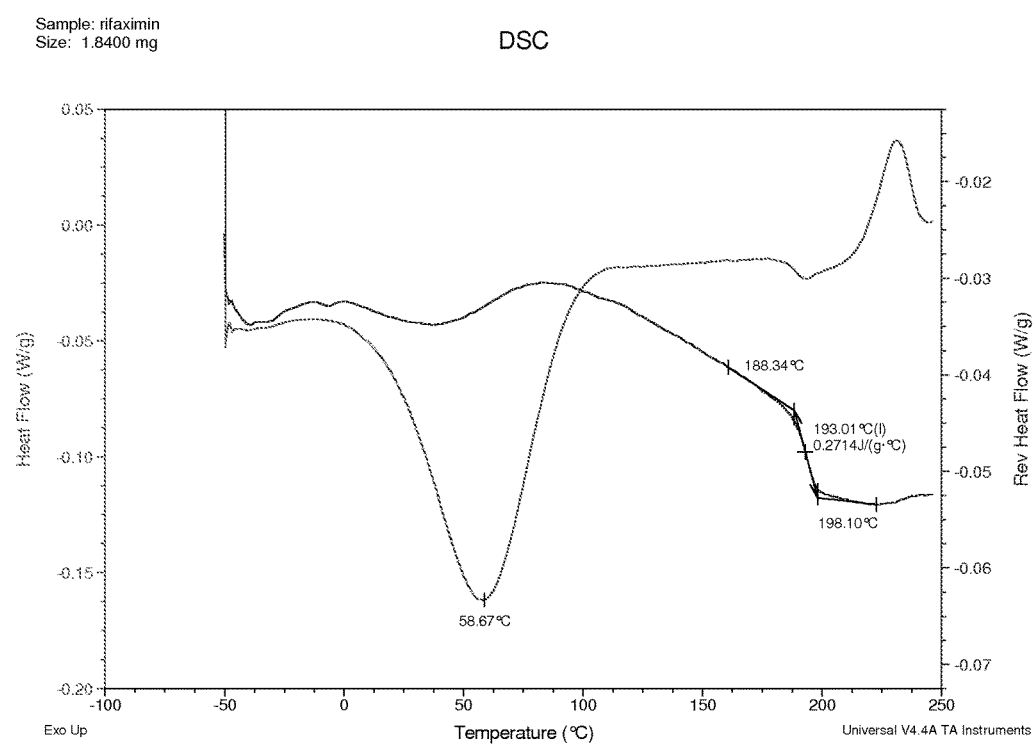
FIG. 4. mDSC thermogram for 50:50 (w/w) Rifaximin/PVP K-90 dispersion obtained from methanol by spray drying.
Figure 5:
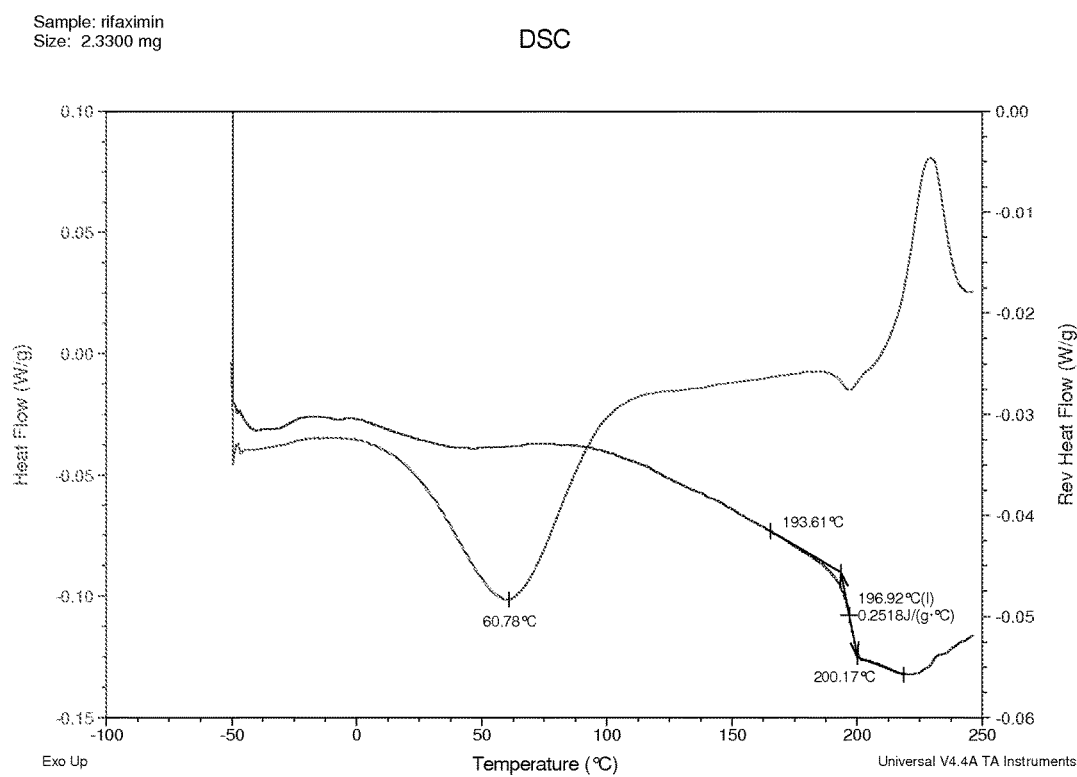
FIG. 5. mDSC thermogram for 75:25 (w/w) Rifaximin/PVP K-90 dispersion obtained from methanol by spray drying.
Figure 6:
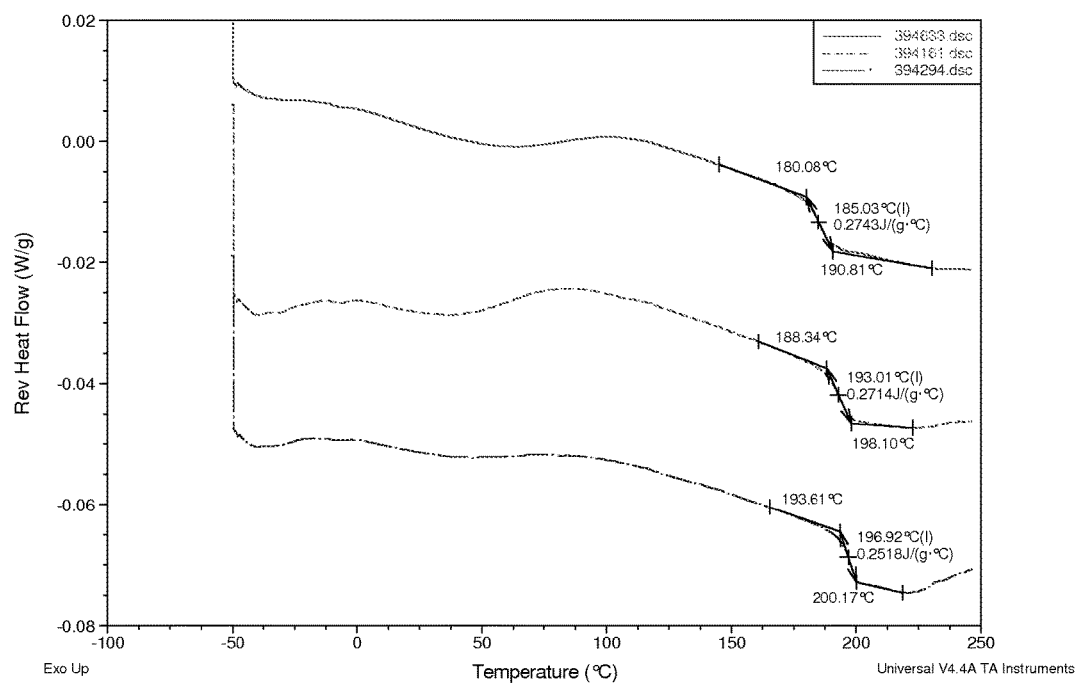
FIG. 6. Overlay of mDSC thermogram for Rifaximin/PVP K-90 dispersions obtained from methanol by spray drying.
Figure 7:
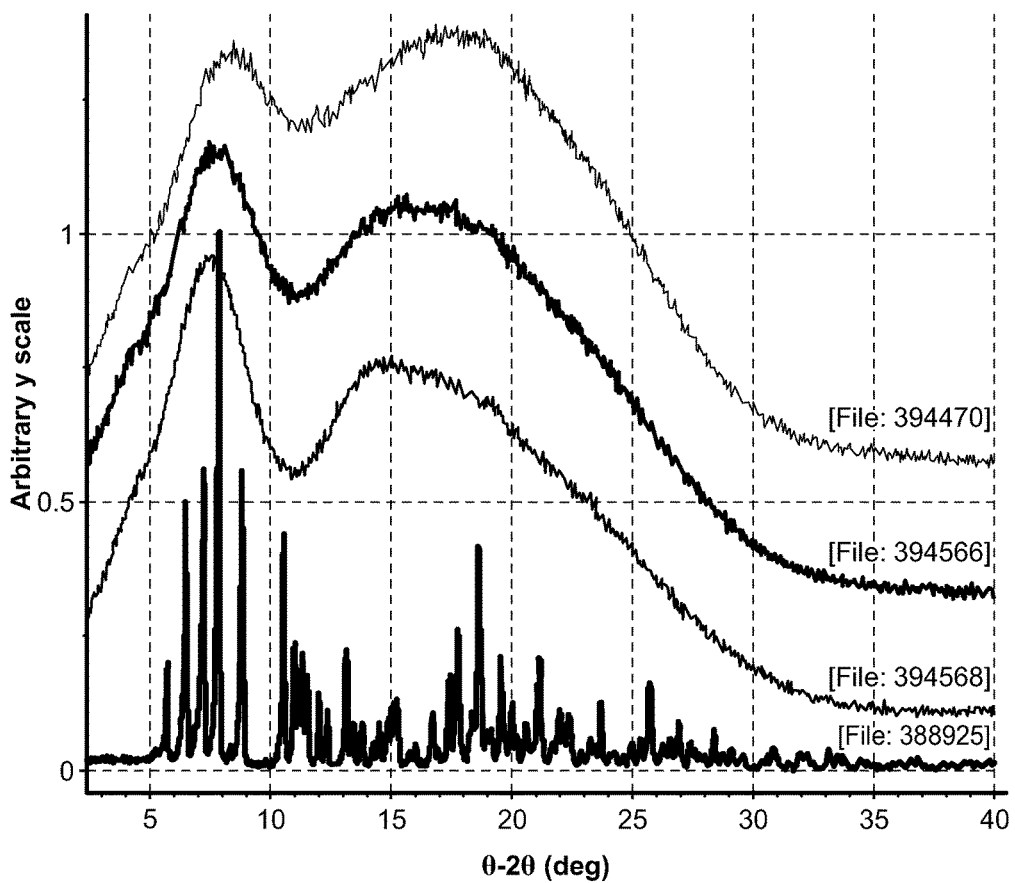
FIG. 7. Overlay of XRPD patterns for Rifaximin/HPMC-P dispersions obtained from methanol by spray drying.
Figure 8:
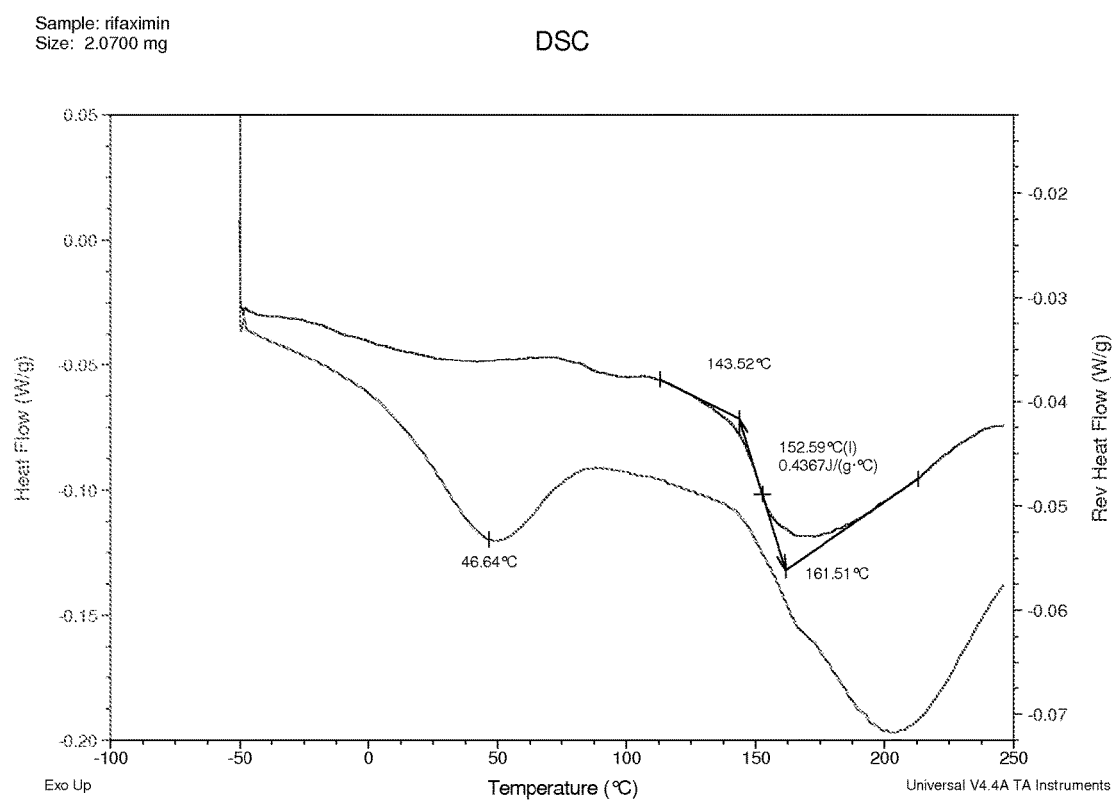
FIG. 8. mDSC thermogram for 25:75 (w/w) Rifaximin/HPMC-P dispersion obtained from methanol by spray drying.
Figure 9:
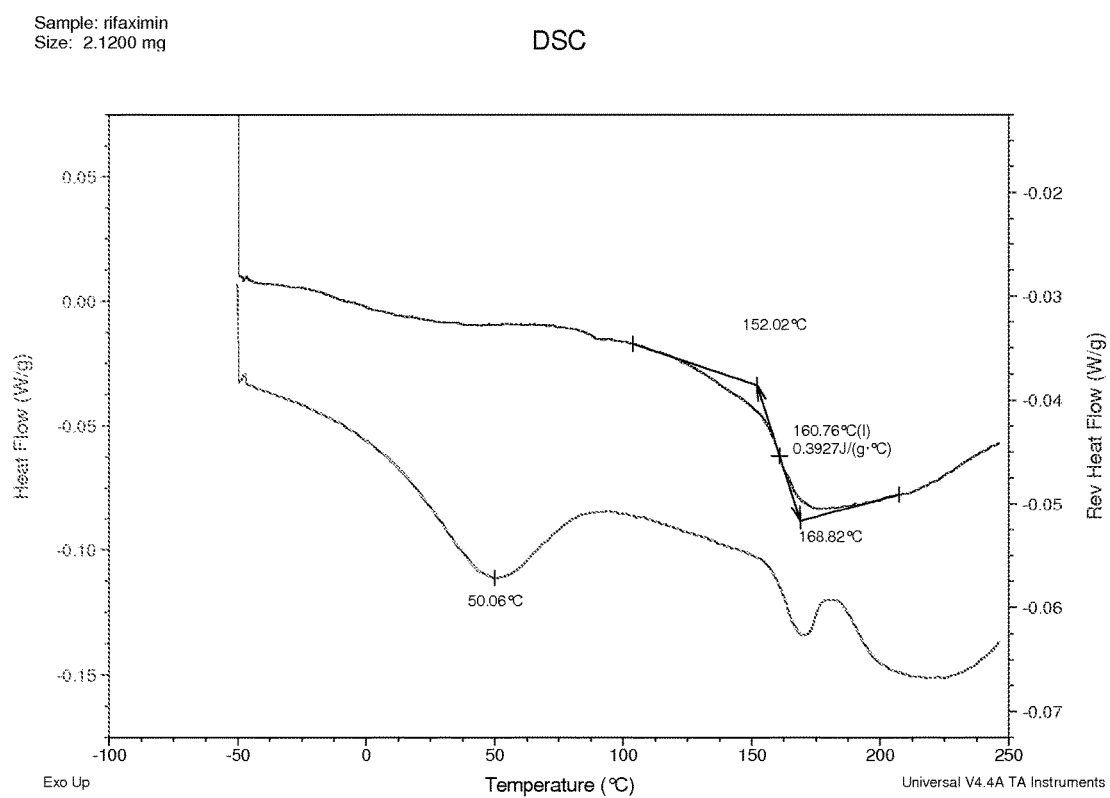
FIG. 9. mDSC thermogram for 50:50 (w/w) Rifaximin/HPMC-P dispersion obtained from methanol by spray drying.
Figure 10:
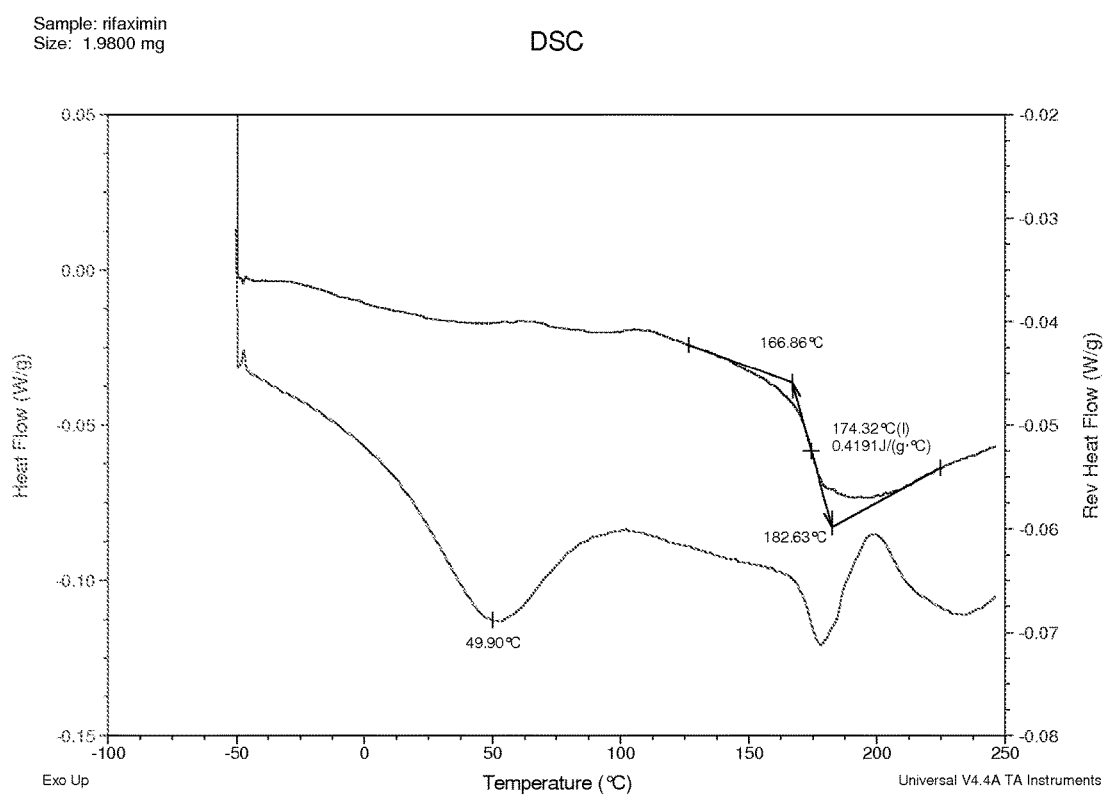
FIG. 10. mDSC thermogram for 75:25 (w/w) Rifaximin/HPMC-P dispersion obtained from methanol by spray drying.

Embodiments described herein relate to the discovery of new solid dispersion forms of rifaximin with a variety of polymers and polymer concentrations. In one embodiment the use of one or more of new solid dispersion forms of the antibiotic known as Rifaximin (INN), in the manufacture of medicinal preparations for the oral or topical route is contemplated. For example, the solid dispersion forms of rifaximin are used to create pharmaceutical compositions, e.g., tablets or capsules, or microgranules comprising solid dispersion forms of rifaximin. Exemplary methods for producing rifaximin microgranules are set forth in the examples. Rifaximin microgranules can be formulated into pharmaceutical compositions as described herein.

Embodiments described herein also relate to administration of such medicinal preparations to a subject in need of treatment with antibiotics. Provided herein are solid dispersion forms of rifaximin with a variety of polymers and polymer concentrations.

As used herein, the term "intragranular release controlling agent" include agents that cause a pharmaceutical composition, e.g., a microgranule, to breakdown thereby releasing the active ingredient, e.g., rifaximin. Exemplary intragranular release controlling agent, include disintegrants such as crosprovidone, sodium starch glycolate, corn starch, microcrystalline cellulose, cellulosic derivatives, sodium bicarbonate, and sodium alginate.

In one embodiment, the intragranular release controlling agent comprises between about 2 wt % to about 40 wt % of the microgranule, about 5 wt % to about 20 wt % of the microgranule, about 8-15 wt % or about 10 wt % of the microgranule.

In another embodiment, the microgranule comprises a surfactant, e.g., a non-ionic surfactant. In one embodiment, the non-ionic surfactant comprises between about 2 wt % to about 10 wt % of the microgranule, between about 4 wt % to about 8 wt % of the microgranule, about 6 to about 7 wt % of the microgranule, or about 5.0 wt % of the microgranule.

In another embodiment, the microgranule comprises an antioxidant. In one embodiment, the antioxidant comprises between about 0.1 wt % to about 3 wt % of the microgranule, between 0.3 wt % to about 2 wt % or between about 0.5 wt % to about 1 wt % of the microgranule.

As used herein, the term "intragranular" refers to the components that reside within the microgranule. As used herein, the term "extragranular" refers to the components of the pharmaceutical composition that are not contained within the microgranule.

As used herein, the term polymorph is occasionally used as a general term in reference to the forms of rifaximin and includes within the context, salt, hydrate, polymorph cocrystal and amorphous forms of rifaximin. This use depends on context and will be clear to one of skill in the art.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about ±0.2 degrees 2-θ. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

As used herein, "similar" in reference to a form exhibiting characteristics similar to, for example, an XRPD, an IR, a Raman spectrum, a DSC, TGA, NMR, SSNMR, etc, indicates that the polymorph or cocrystal is identifiable by that method and could range from similar to substantially similar, so long as the material is identified by the method with variations expected by one of skill in the art according to the experimental variations, including, for example, instruments used, time of day, humidity, season, pressure, room temperature, etc.

As used herein, "rifaximin solid dispersion," "rifaximin ternary dispersion," "solid dispersion of rifaximin," "solid dispersion", "solid dispersion forms of rifaximin", "SD", "SDD", and "form solid dispersion of rifaximin" are intended to have equivalent meanings and include rifaximin polymer dispersion composition. These compositions are XRPD amorphous, but distinguishable from XRPD of amorphous rifaximin. As shown in the Examples and Figures, the rifaximin polymer dispersion compositions are physically chemically distinguishable from amorphous rifaximin, including different Tg, different XRPD profiles and different dissolution profiles.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/ or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from a bowel disorder or other disorder treatable by rifaximin or who could otherwise benefit from the administration of rifaximin solid dispersion compositions as described herein, such as human and non-human animals. The term "non-human animals" includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, e.g., subjects suffering from one or more of an immune suppression, subjects that have been exposed to other subjects with a bacterial infection, physicians, nurses, subjects traveling to remote areas known to harbor bacteria that causes travelers' diarrhea, subjects who drink amounts of alcohol that damage the liver, subjects with a history of hepatic dysfunction, etc.

The language "a prophylactically effective amount" of a composition refers to an amount of a rifaximin solid dispersion formulation or otherwise described herein which is effective, upon single or multiple dose administration to the subject, in preventing or treating a bacterial infection.

The language "therapeutically effective amount" of a composition refers to an amount of a rifaximin solid dispersion effective, upon single or multiple dose administration to the subject to provide a therapeutic benefit to the subject. In one embodiment, the therapeutic benefit is wounding or killing a bacterium, or in prolonging the survivability of a subject with such a bowel or skin disorder. In another embodiment, the therapeutic benefit is inhibiting a bacterial infection or prolonging the survival of a subject with such a bacterial infection beyond that expected in the absence of such treatment.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

In respect to possible adverse events coupled to the therapeutic use of rifaximin, the induction of bacterial resistance to the antibiotics is of particular relevance.

From this point of view, any differences found in the systemic absorption of the forms of rifaximin disclosed herein may be significant, because at sub-inhibitory concentration of rifaximin, such as in the range from 0.1 to 1 µg/ml, selection of resistant mutants has been demonstrated to be possible (Marchese A. et al. *In vitro activity of rifaximin, metronidazole and vancomycin against clostridium difficile and the rate of selection of spontaneously resistant mutants against representative anaerobic and aerobic bacteria, including ammonia-producing species. Chemotherapy,* 46(4), 253-266, (2000)).

Forms, formulations and compositions of rifaximin have been found to have differing in vivo bioavailability properties. Thus, the polymorphs disclosed herein would be useful in the preparation of pharmaceuticals with different characteristics for the treatment of infections. This would allow generation of rifaximin preparations that have significantly different levels of adsorption with $C_{max}$ values from about 0.0 ng/ml to 5.0 µg/ml. This leads to preparation of rifaximin compositions that are from negligibly to significantly adsorbed by subjects undergoing treatment. One embodiment described herein is modulating the therapeutic action of rifaximin by selecting the proper form, formulation and/or composition, or mixture thereof, for treatment of a subject. For example, in the case of invasive bacteria, the most bioavailable form, formulation and/or composition can be selected from those disclosed herein, whereas in case of non-invasive pathogens less adsorbed forms, formulations and/or compositions of rifaximin can be selected, since they may be safer for the subject undergoing treatment. A form, formulation and/or composition of rifaximin may determine solubility, which may also determine bioavailability.

For XRPD analysis, accuracy and precision associated with third party measurements on independently prepared samples on different instruments may lead to variability which is greater than ±0.1° 2θ. For d-space listings, the wavelength used to calculate d-spacings was 1.541874 A, a weighted average of the Cu—Kα1 and Cu—Kα2 wavelengths. Variability associated with d-spacing estimates was calculated from the USP recommendation, at each d-spacing, and provided in the respective data tables and peak lists.

Methods of Treatment

Provided herein are methods of treating, preventing, or alleviating bowel related disorders comprising administering to a subject in need thereof an effective amount of one or more of the solid dispersion compositions of rifaximin. Bowel related disorders include one or more of irritable bowel syndrome, diarrhea, microbe associated diarrhea, *Clostridium difficile* associated diarrhea, travelers' diarrhea, small intestinal bacterial overgrowth, Crohn's disease, diverticular disease, chronic pancreatitis, pancreatic insufficiency, enteritis, colitis, hepatic encephalopathy, minimal hepatic encephalopathy or pouchitis.

The length of treatment for a particular bowel disorder will depend in part on the disorder. For example, travelers' diarrhea may only require treatment duration of 12 to about 72 hours, while Crohn's disease may require treatment durations from about 2 days to 3 months. Dosages of rifaximin will also vary depending on the diseases state. Proper dosage ranges are provided herein infra. The polymorphs and cocrystals described herein may also be used to treat or prevent apathology in a subject suspected of being exposed to a biological warfare agent.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

Topical skin infections and vaginal infections may also be treated with the rifaximin compositions described herein. Thus, described herein are methods of using a solid dispersion composition of rifaximin (SD rifaximin compositions) to treat vaginal infections, ear infections, lung infections, periodontal conditions, rosacea, and other infections of the skin and/or other related conditions. Provided herein are vaginal pharmaceutical compositions to treat vaginal infection, particularly bacterial vaginosis, to be administered topically, including vaginal foams and creams, containing a therapeutically effective amount of SD rifaximin compositions, preferably between about 50 mg and 2500 mg. Pharmaceutical compositions known to those of skill in the art for the treatment of vaginal pathological conditions by the topical route may be advantageously used with SD rifaximin compositions. For example, vaginal foams, ointments, creams, gels, ovules, capsules, tablets and effervescent tablets may be effectively used as pharmaceutical compositions containing SD rifaximin compositions, which may be administered topically for the treatment of vaginal infections, including bacterial vaginosis. Also provided herein are method of using SD rifaximin compositions to treat gastric dyspepsia, including gastritis, gastroduodenitis, antral gastritis, antral erosions, erosive duodenitis and peptic ulcers. These conditions may be caused by the *Helicobacter pylori*. Pharmaceutical formulations known by those of skill in the art with the benefit of this disclosure to be used for oral administration of a drug may be used. Provided herein are methods of treating ear infections with SD rifaximin compositions. Ear infections include external ear infection, or a middle and inner ear infection. Also provided herein are methods of using SD rifaximin compositions to treat or prevent aspiration pneumonia and/or sepsis, including the prevention of aspiration pneumonia and/or sepsis in patients undergoing acid suppression or undergoing artificial enteral feedings via a Gastrostomy/Jejunostomy or naso/oro gastric tubes; prevention of aspiration pneumonia in patients with impairment of mental status, for example, for any reason, for subjects undergoing anesthesia or mechanical ventilation that are at high risk for aspiration pneumonia. Provided herein are methods to treat or to prevent periodontal conditions, including plaque, tooth decay and gingivitis. Provided herein are methods of treating rosacea, which is a chronic skin condition involving inflammation of the cheeks, nose, chin, forehead, or eyelids.

Pharmaceutical Preparations

Embodiments also provide pharmaceutical compositions, comprising an effective amount of one or more SD rifaximin compositions, or microgranules comprising SD forms of rifaximin described herein (e.g., described herein and a pharmaceutically acceptable carrier). In a further embodiment, the effective amount is effective to treat a bacterial infection, e.g., small intestinal bacterial overgrowth, Crohn's disease, hepatic encephalopathy, antibiotic associated colitis, and/or diverticular disease. Embodiments also provide pharmaceutical compositions, comprising an effective amount of rifaximin SD compositions.

For examples of the use of rifaximin to treat Travelers' diarrhea, see Infante R M, Ericsson C D, Zhi-Dong J, Ke S, Steffen R, Riopel L, Sack D A, DuPont, H L., Enteroaggregative *Escherichia coli* Diarrhea in Travelers: Response to Rifaximin Therapy. *Clinical Gastroenterology and Hepatology*. 2004; 2:135-138; and Steffen R, M.D., Sack DA, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology*. May 2003, Volume 98, Number 5, all of which are incorporated herein by reference in their entirety. Examples of treating hepatic encephalopathy with rifaximin see, for example, N. Engl J Med. 2010_362_1071-1081.

Embodiments also provide pharmaceutical compositions comprising rifaximin SD compositions and a pharmaceutically acceptable carrier. Embodiments of the pharmaceutical composition further comprise excipients, for example, one or more of a diluting agent, binding agent, lubricating agent, intragranular release controlling agent, e.g., a disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin SD composition is administered to the subject using a pharmaceutically-acceptable formulation, e.g., a pharmaceutically-acceptable formulation that provides sustained or delayed delivery of the SD rifaximin composition to a subject for at least 2, 4, 6, 8, 10, 12 hours, 24 hours, 36 hours, 48 hours, one week, two weeks, three weeks, or four weeks after the pharmaceutically-acceptable formulation is administered to the subject. The pharmaceutically-acceptable formulations may contain microgranules comprising rifaximin as described herein.

In certain embodiments, these pharmaceutical compositions are suitable for topical or oral administration to a subject. In other embodiments, as described in detail below, the pharmaceutical compositions described herein may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those SD rifaximin compositions and cocrystals presented herein, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these compositions include the step of bringing into association a SD rifaximin composition(s) or microgranules containing the SD rifaximin compositions with the carrier and, optionally, one or more accessory ingredients. In general, the formulations are prepared by uniformly and intimately bringing into association a SD rifaximin composition with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a SD rifaximin composition(s) as an active ingredient. A compound may also be administered as a bolus, electuary or paste.

The SD compositions of rifaximin disclosed herein can be advantageously used in the production of medicinal preparations having antibiotic activity, containing rifaximin, for both oral and topical use. The medicinal preparations for oral use will contain an SD composition of rifaximin together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; coloring, flavoring, disintegrants, and sweetening agents.

Embodiments described herein include SD rifaximin composition administrable by the oral route, for instance coated and uncoated tablets, of soft and hard gelatin capsules, sugar-coated pills, lozenges, wafer sheets, pellets and powders in sealed packets or other containers.

Pharmaceutical compositions for rectal or vaginal administration may be presented as a suppository, which may be prepared by mixing one or more SD rifaximin composition(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Compositions which are suitable for vaginal administration also include pessaries, tampons, creams, gels, pastes, foams or spray formulations containing such carriers as are known in the art to be appropriate.

Dosage forms for the topical or transdermal administration of a SD rifaximin composition(s) include powders, sprays, ointments, pastes, creams, lotions, gels, solutions, patches and inhalants. The active SD rifaximin composition(s) may be mixed under sterile conditions with a pharmaceutically-acceptable carrier, and with any preservatives, buffers, or propellants which may be required.

Ointments, pastes, creams and gels may contain, in addition to SD rifaximin composition(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a SD rifaximin composition(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The SD rifaximin composition(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a SD rifaximin composition(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions suitable for parenteral administration may comprise one or more SD rifaximin composition(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

When the SD rifaximin composition(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the SD rifaximin composition(s) are formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 25 to 3000 mg per day. Other doses include, for example, 600 mg/day, 1100 mg/day and 1650 mg/day. Other exemplary doses include, for example, 1000 mg/day, 1500 mg/day, from between 500 mg to about 1800 mg/day or any value in-between.

A preferred dose of the SD rifaximin composition disclosed herein is the maximum that a subject can tolerate without developing serious side effects. Preferably, the SD rifaximin composition is administered at a concentration of about 1 mg to about 200 mg per kilogram of body weight, about 10 to about 100 mg/kg or about 40 mg to about 80 mg/kg of body weight. Ranges intermediate to the above-recited values are also intended to be part. For example, doses may range from 50 mg to about 2000 mg/day.

In combination therapy treatment, the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the rifaximin SD composition is less than its effective amount in case the other therapeutic agent is not administered. In another embodiment, the effective amount of the conventional agent is less than its effective amount in case the rifaximin SD composition is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same subject's visit.

In certain embodiments, one or more compounds and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a SD rifaximin composition may be repeated and the administration may be separated by at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months. A treatment for hepatic encephalopathy may be, for example, for the remainder of the subject's life span. A treatment for IBS may be intermittent for weeks or months at a time or for the remainder of the subject's life.

Compositions and Formulations

Rifaximin solid dispersions, pharmaceutical compositions comprising SD rifaximin or microgranules comprising rifaximin solid dispersions, can be made from, for example, polymers including polyvinylpyrrolidone (PVP) grade K-90, hydroxypropyl methylcellulose phthalate (HPMC-P) grade 55, hydroxypropyl methylcellulose acetate succinate (HPMC-AS) grades HG and MG, and a polymethacrylate (Eudragit® L100-55). Rifaximin solid dispersion compositions are comprised of, for example, 10:90, 15:85, 20:80, 25:75, 30:70, 40:60, 50:50 60:40, 70:30, 75:25, 80:20, 85:15, and 90:10 (Rifaximin/polymer, by weight). Preferred solid dispersions are comprised of 25:75, 50:50 and 75:25 (Rifaximin/polymer, by weight). In addition to rifaximin and polymer, solid dispersions may also comprise surfactants, for example, non-ionic, surfactant polyols.

An example of a formulation comprises about 50:50 (w/w) Rifaximin:HPMC-AS MG with from between about 2 wt % to about 10 wt % of a non-ionic, surfactant polyol, for example, Pluronic F-127.

One example of a formulation comprises 50:50 (w/w) Rifaximin:HPMC-AS MG with about 5.9 wt %) of a non-ionic, surfactant polyol, for example, Pluronic F-127. Spray dried rifaximin ternary dispersion (50:50 (w/w) rifaximin: HPMC-AS MG with 5.9 wt % Pluronic F-127) was blended with 10 wt % croscarmellose sodium and then filled into gelatin capsules. Each capsule contains 275 mg of rifaximin and the blend formulation is 85:5:10 of 50:50 (w/w) Rifaximin:HPMC-AS MG:Pluronic:croscarmellose sodium (calculated in total solids). Other examples of microgranules and pharmaceutical compositions comprising SD rifaximin are described in the examples.

To form the rifaximin solid dispersion, the components, e.g., rifaximin, polymer and methanol are mixed and then spray dried. Exemplary conditions are summarized in Table 9 and the procedure outlined below and in Examples 3 and 4.

Exemplary Spray Drying Process Parameters, include for example:
Spray Dryer—e.g., PSD 1;
Single or multi-fluid nozzle: e.g., a two Fluid Niro Nozzle;
Nozzle orifice—0.1-10 mm;
Inlet gas temperature—75-150±5 deg C.;
Process gas flow (mmH2O)—20-70, preferred 44;

Atomizing gas pressure—0.7-1 bar;

Feed rate—2-7 kg/Hr;

Outlet temperature—30-70±3 deg C.;

Solution temperature—20-50 deg C.; and

Post spray drying vacuum dry at 20-60 deg C., for between about 2 and 72 hrs.

Article of Manufacture

Another embodiment includes articles of manufacture that comprise, for example, a container holding a rifaximin SD pharmaceutical composition suitable for oral or topical administration of rifaximin in combination with printed labeling instructions providing a discussion of when a particular dosage form should be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising SD rifaximin composition or formulation wherein the container holds preferably rifaximin composition in unit dosage form and is associated with printed labeling instructions advising of the differing absorption when the pharmaceutical composition is taken with and without food.

Packaged compositions are also provided, and may comprise a therapeutically effective amount of rifaximin. Rifaximin SD composition and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of the solid dispersion forms of rifaximin and instructions for use. The instructions for use may contain proscribing information, dosage information, storage information, and the like.

Packaged compositions are also provided, and may comprise a therapeutically effective amount of an SD rifaximin composition and a pharmaceutically acceptable carrier or diluent, wherein the composition is formulated for treating a subject suffering from or susceptible to a bowel disorder, and packaged with instructions to treat a subject suffering from or susceptible to a bowel disorder.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The chemical structure of Rifaximin is shown below in FIG. 1.

Example 1

Solid Dispersions of Rifaximin

Various polymers were formulated with rifaximin into solids prepared by methanol and spray drying at small scale (~1 g). Polymers, including polyvinylpyrrolidone (PVP) grade K-90, hydroxypropyl methylcellulose phthalate (HPMC-P) grade 55, hydroxypropyl methylcellulose acetate succinate (HPMC-AS) grades HG and MG, and a polymethacrylate (Eudragit® L100-55) were used. Solids have compositions of 25:75, 50:50 and 75:25 (Rifaximin/polymer, by weight).

Samples generated were observed under polarized light microscope after preparation and were characterized by XRPD. The results are included in Table 1 through Table 5. Birefringence with extinction (B/E) was not observed for any of the samples, indicating solids without crystalline order were obtained. No sharp peaks were evident by visual inspection of XRPD patterns of these samples, consistent with non-crystalline materials, as shown in FIG. 2 (with PVP K-90), FIG. 7 (with HPMC-P), FIG. 12 (with HMPC-AS HG), FIG. 12 (with HMPC-AS MG), and FIG. 17 (with Eudragit L100-55).

Materials were characterized by mDSC where the appearance of a single glass transition temperature (Tg), provides support for a non-crystalline fully miscible dispersion. All the dispersions prepared with PVP K-90 display a single apparent Tg at approximately 185° C. (FIG. 3, 25:75 w/w), 193° C. (FIG. 4, 50:50 w/w), and 197° C. (FIG. 5, 75:25) respectively. The change in heat capacity (ΔCp) at Tg is approximately 0.3 J/g·° C. for each dispersion. A non-reversible endotherm, which is likely due to the residual solvent in the materials, was observed in each of Rifaximin/PVP K-90 dispersions centered at approximately 78° C., 59° C. and 61° C.

From FIG. 6, Tg of Rifaximin/PVP K-90 dispersions increases with the increased Rifaximin concentration, which is due to the higher Tg of Rifaximin (199° C.) than PVP K-90 (174° C.). Evidence of a single Tg may suggest that the components of the dispersion are intimately mixed, or miscible.

Dispersions prepared with other polymers also display a single apparent Tg, as a step change in the reversing heat flow signal by mDSC. Dispersions prepared with HPMC-P exhibit Tg at 153° C. (FIG. 8, 25:75 w/w), 161° C. (FIG. 9, 50:50 w/w) and 174° C. (FIG. 10, 75:25 w/w) respectively, with ΔCp at Tg approximately 0.4 J/g·° C.

With HPMC-AS HG, dispersions display Tg at 137° C. (FIG. 13, 25:75 w/w), 154° C. (FIG. 14, 50:50 w/w) and 177° C. (FIG. 15, 75:25 w/w) respectively; ΔCp at Tg is approximately 0.4 or 0.3 J/g·° C.

With HPMC-AS MG, dispersions display Tg at 140° C. (FIG. 18, 25:75 w/w), 159° C. (FIG. 19, 50:50 w/w) and 177° C. (FIG. 10, 75:25 w/w) respectively; ΔCp at Tg is approximately 0.4 or 0.3 J/g·° C.

Dispersions prepared with Eudragit L100-55 exhibit Tg at 141° C. with ΔCp approximately 0.5 J/g·° C. (FIG. 23, 25:75 w/w), 159° C. with ΔCp approximately 0.3 J/g·° C. (FIG. 24,

Figure 25:
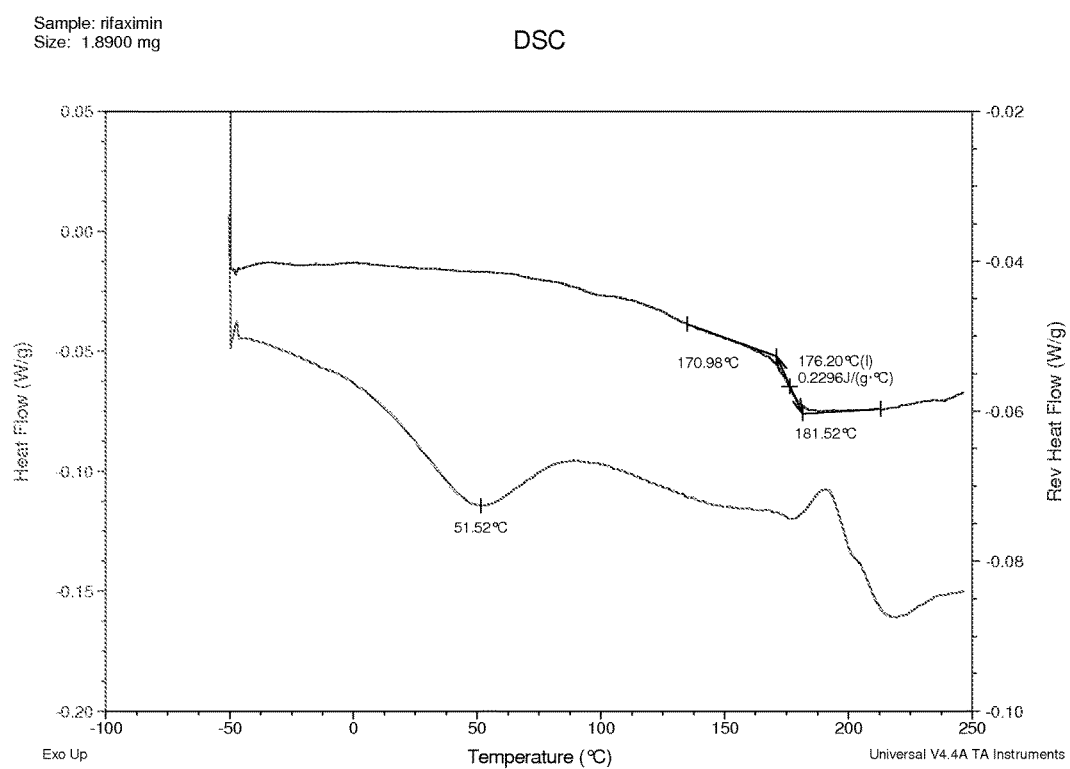
FIG. 25. mDSC thermogram for 75:25 (w/w) Rifaximin/Eudragit L100-55 dispersion obtained from methanol by spray drying.

50:50 w/w), and 176° C. with ΔCp at Tg approximately 0.2 J/g.° C. (FIG. 25, 75:25 w/w) respectively.

Figure 11:
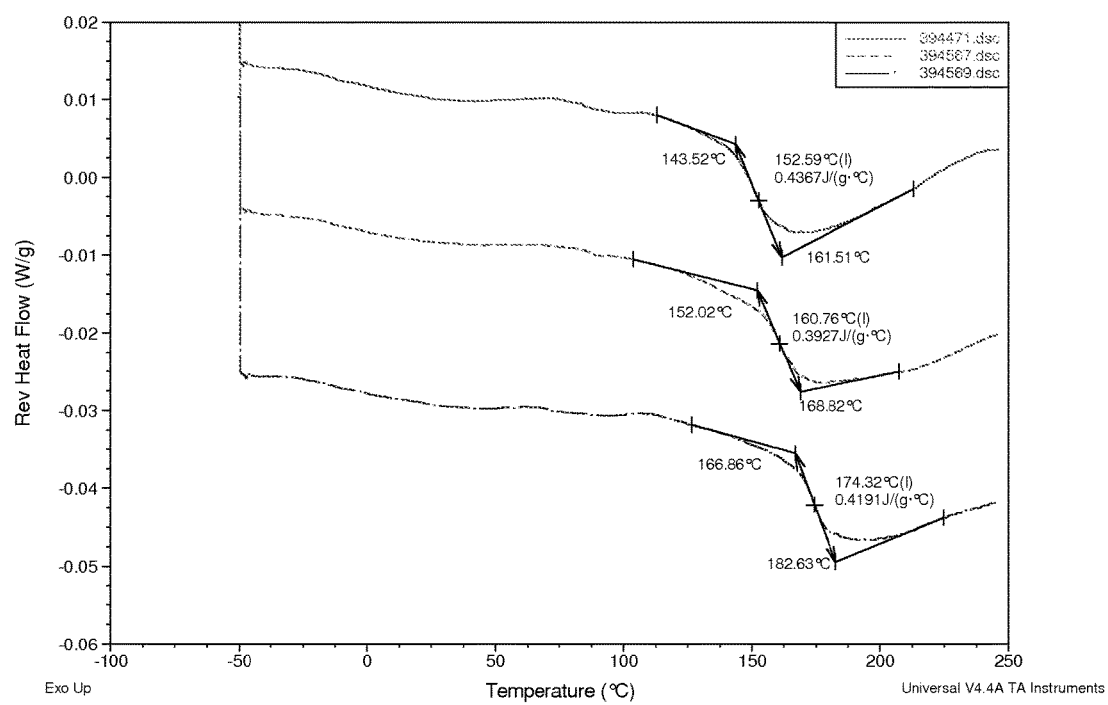
FIG. 11. Overlay of mDSC thermogram for Rifaximin/HPMC-P dispersions obtained from methanol by spray drying.
Figure 12:
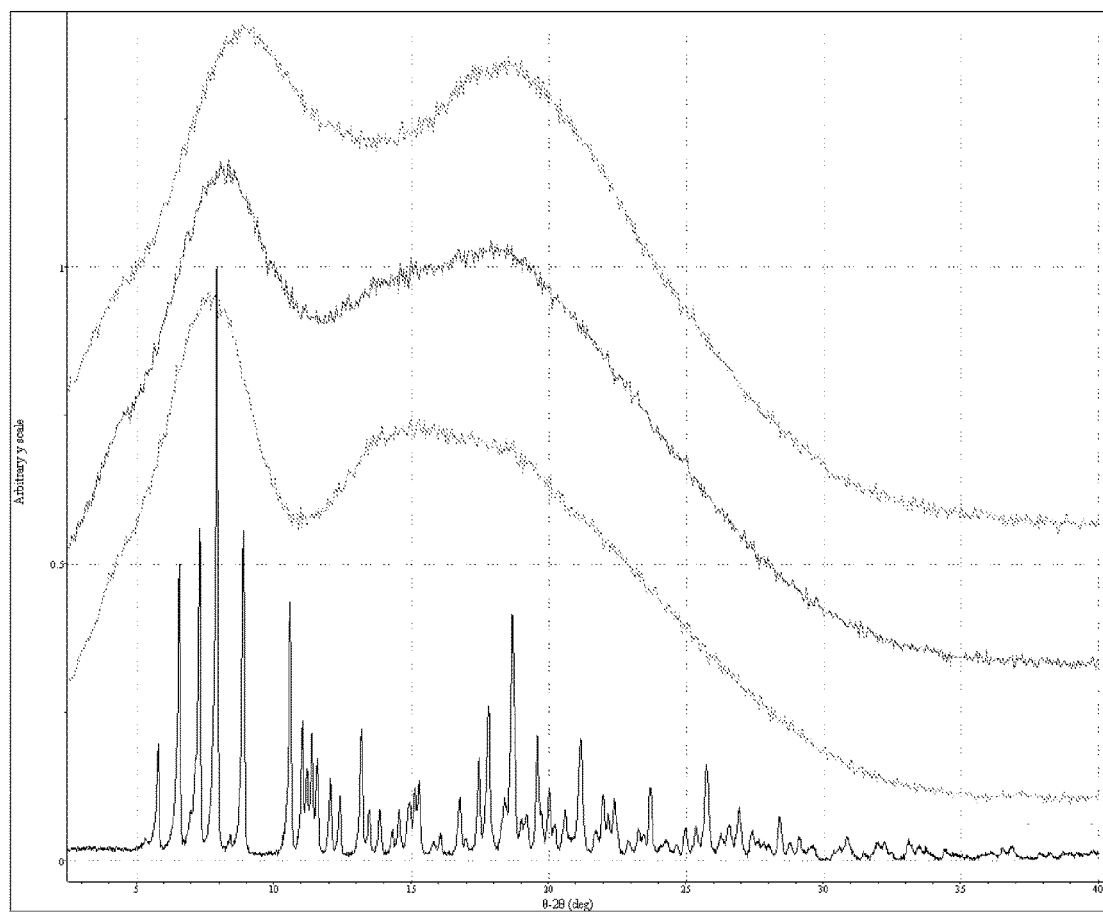
FIG. 12. Overlay of XRPD patterns for Rifaximin/HPMC-AS HG dispersions obtained from methanol by spray drying.
Figure 13:
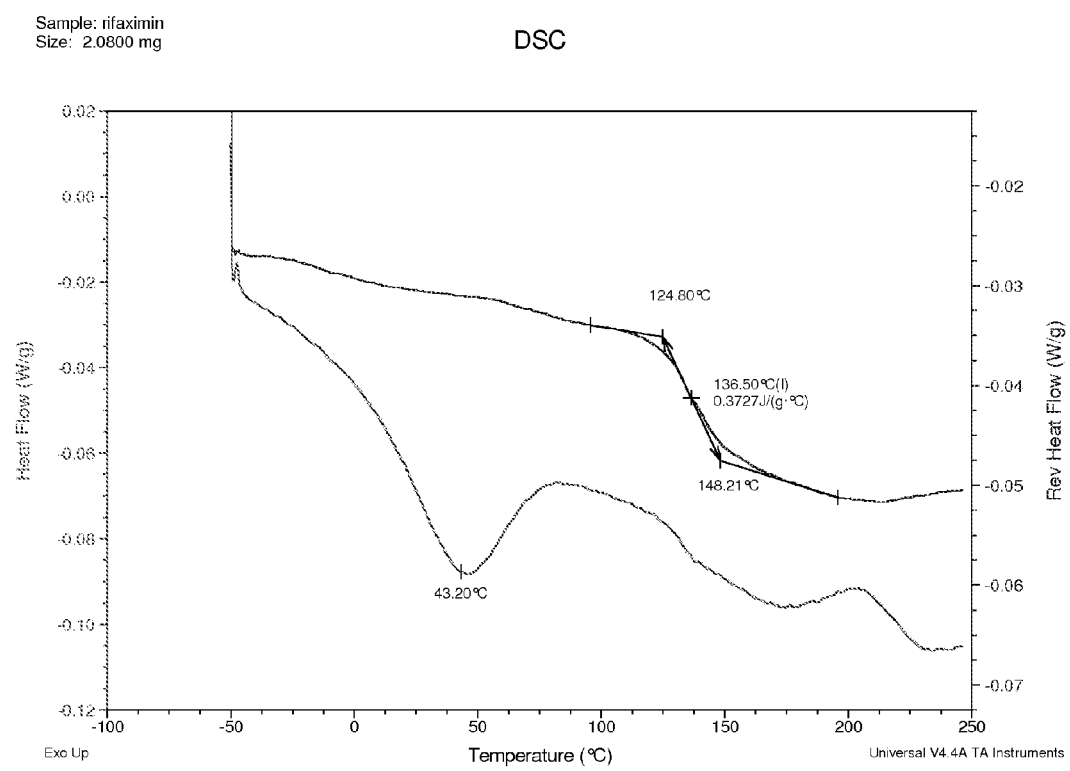
FIG. 13. mDSC thermogram for 25:75 (w/w) Rifaximin/HPMC-AS HG dispersion obtained from methanol by spray drying.
Figure 14:
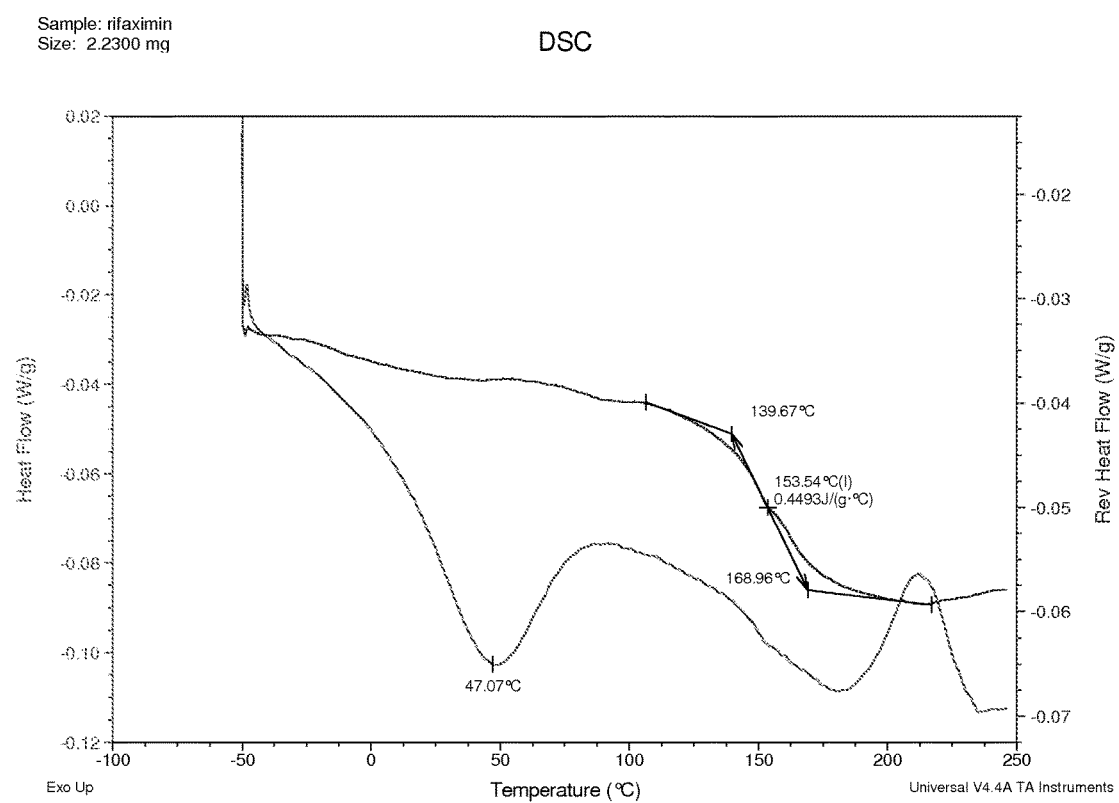
FIG. 14. mDSC thermogram for 50:50 (w/w) Rifaximin/HPMC-AS HG dispersion obtained from methanol by spray drying.
Figure 15:
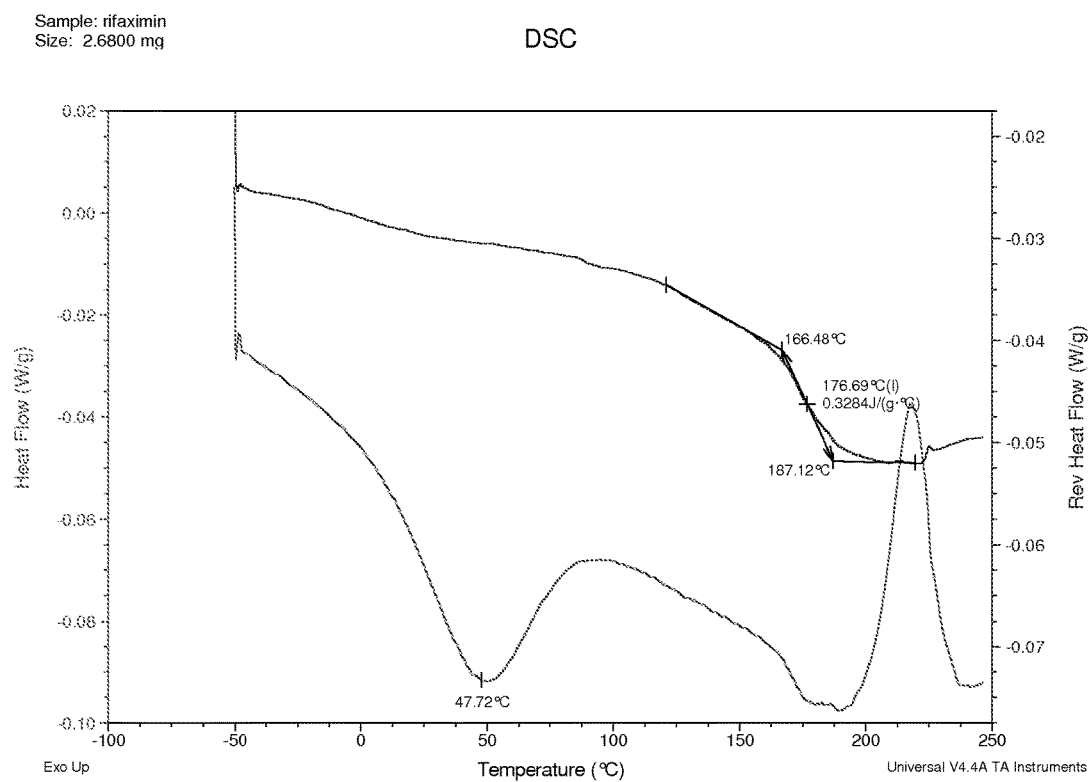
FIG. 15. mDSC thermogram for 75:25 (w/w) Rifaximin/HPMC-AS HG dispersion obtained from methanol by spray drying.
Figure 16:
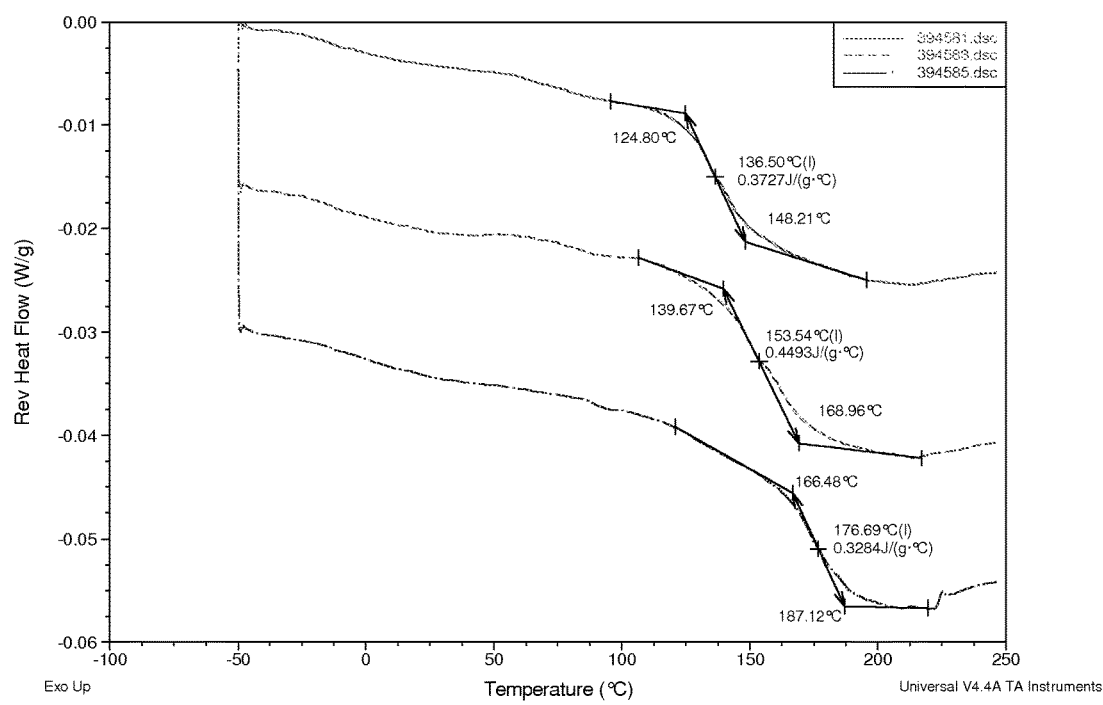
FIG. 16. Overlay of mDSC thermogram for Rifaximin/HPMC-AS HG dispersions obtained from methanol by spray drying.
Figure 17:
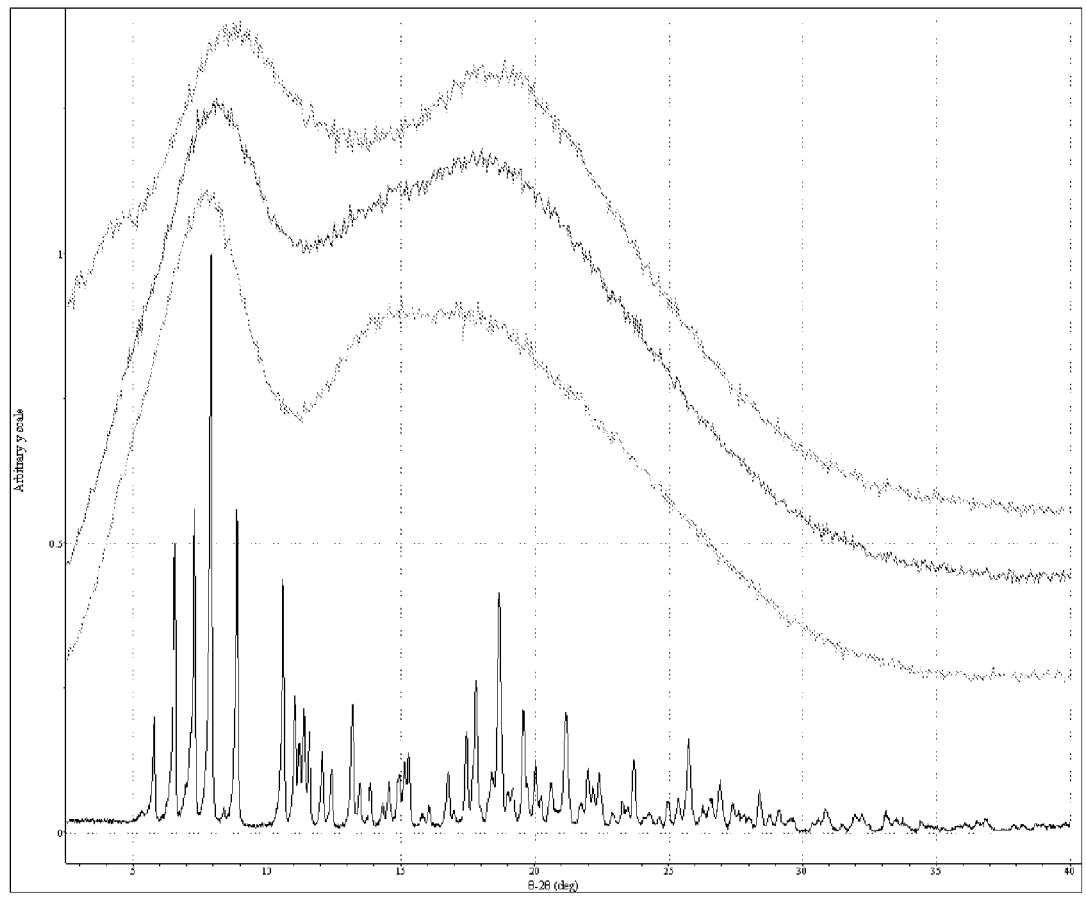
FIG. 17. Overlay of XRPD patterns for Rifaximin/HPMC-AS MG dispersions obtained from methanol by spray drying.
Figure 18:
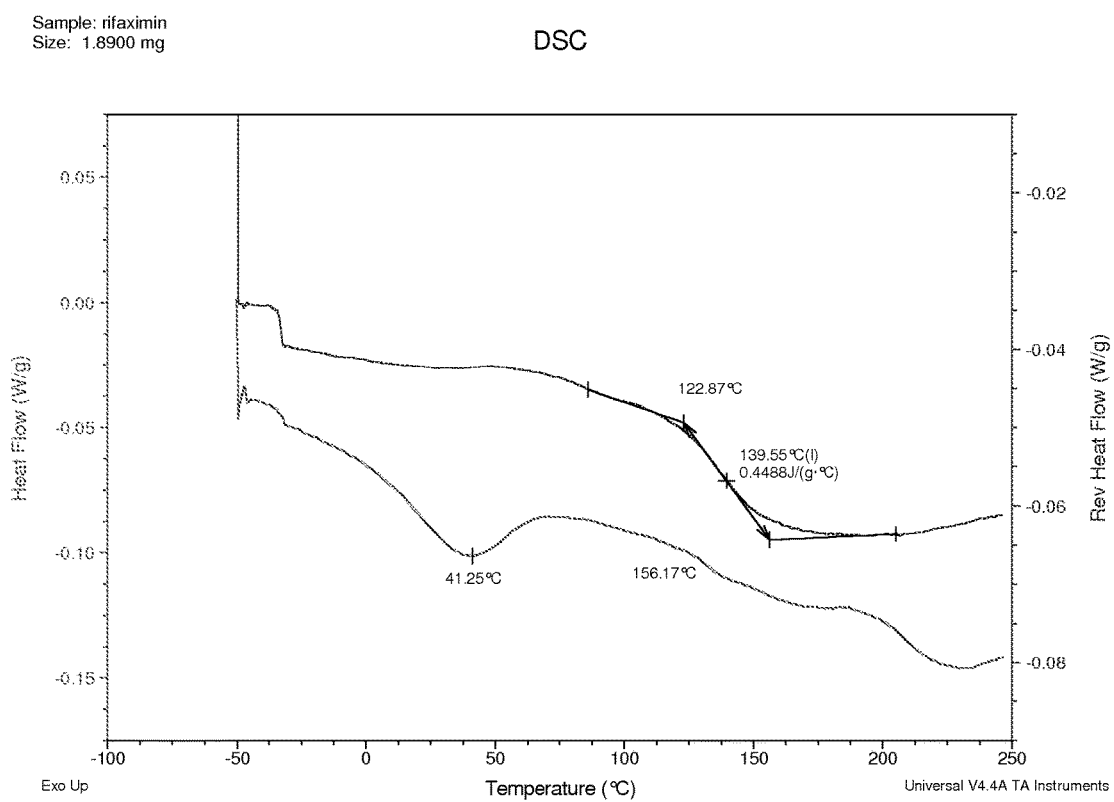
FIG. 18. mDSC thermogram for 25:75 (w/w) Rifaximin/HPMC-AS MG dispersion obtained from methanol by spray drying.
Figure 19:
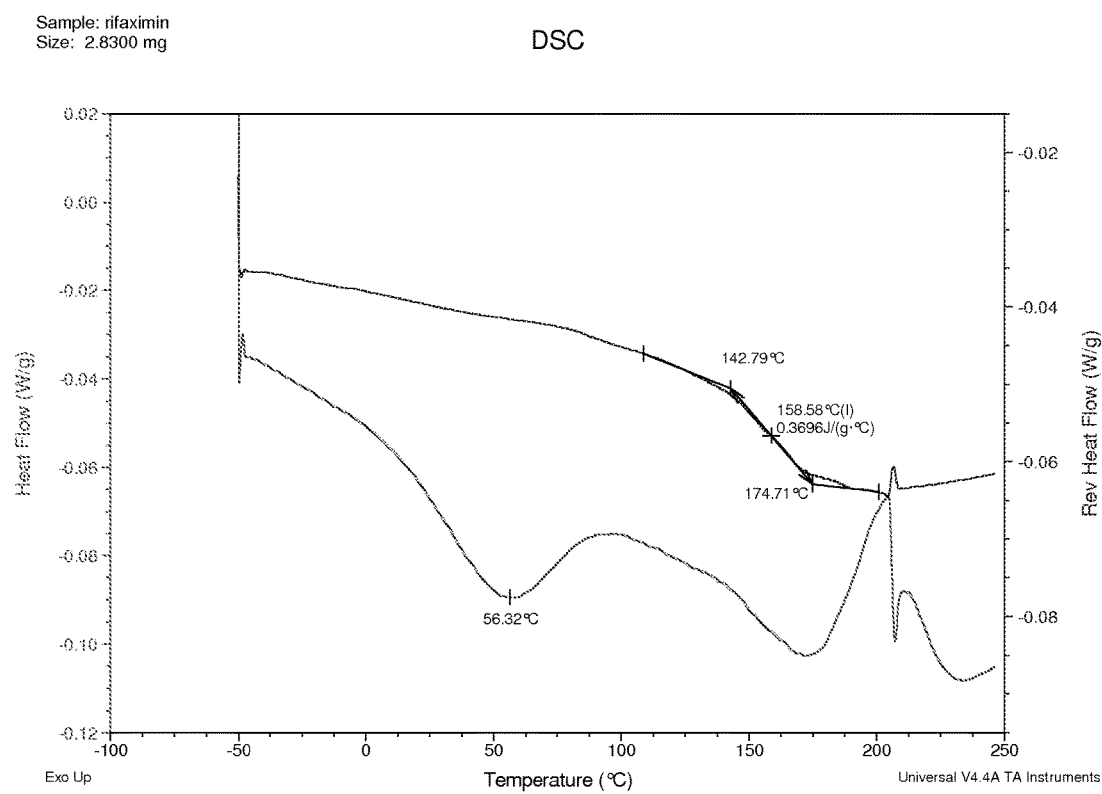
FIG. 19. mDSC thermogram for 50:50 (w/w) Rifaximin/HPMC-AS MG dispersion obtained from methanol by spray drying.
Figure 20:
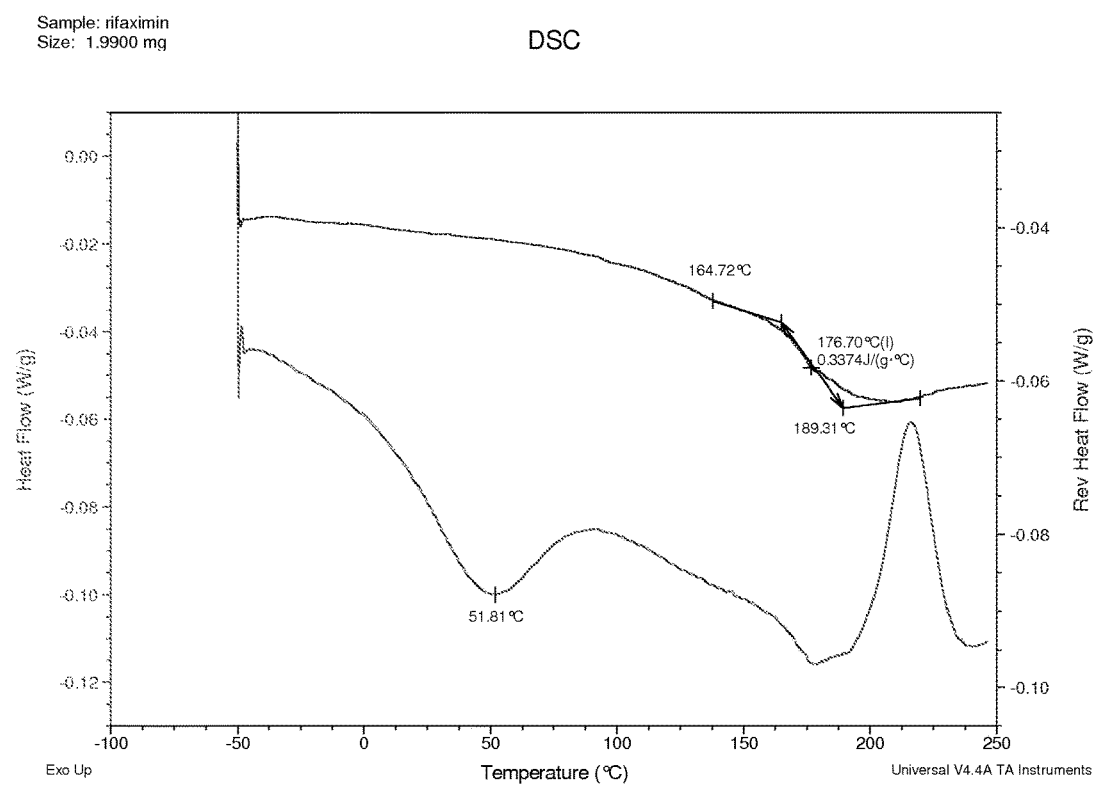
FIG. 20. mDSC thermogram for 75:25 (w/w) Rifaximin/HPMC-AS MG dispersion obtained from methanol by spray drying.
Figure 21:
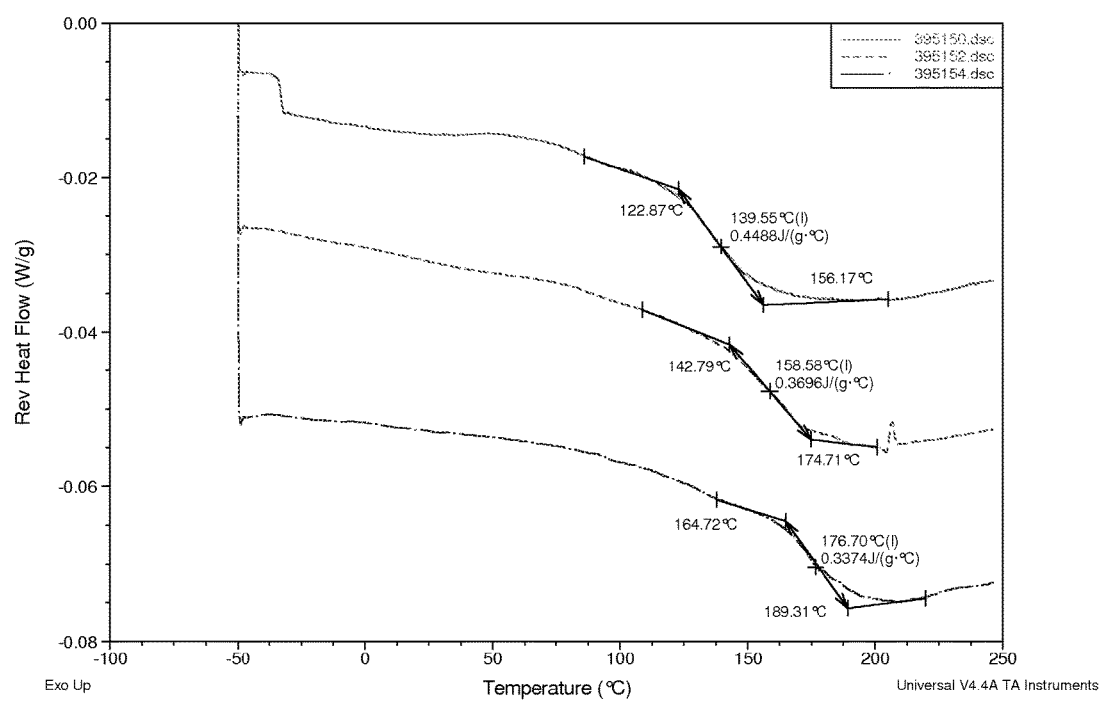
FIG. 21. Overlay of mDSC thermogram for Rifaximin/HPMC-AS MG dispersions obtained from methanol by spray drying.
Figure 22:
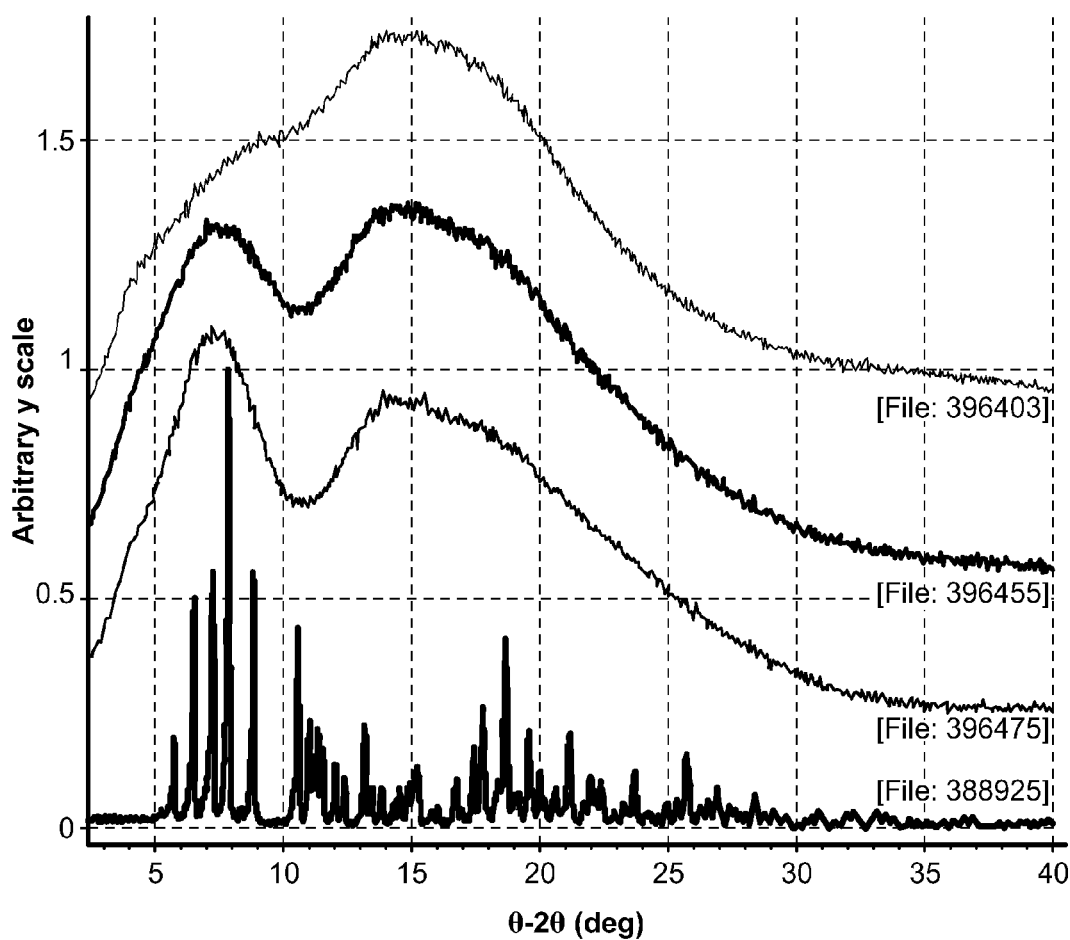
FIG. 22. Overlay of XRPD patterns for Rifaximin/Eudragit L100-55 dispersions obtained from methanol by spray drying.
Figure 23:
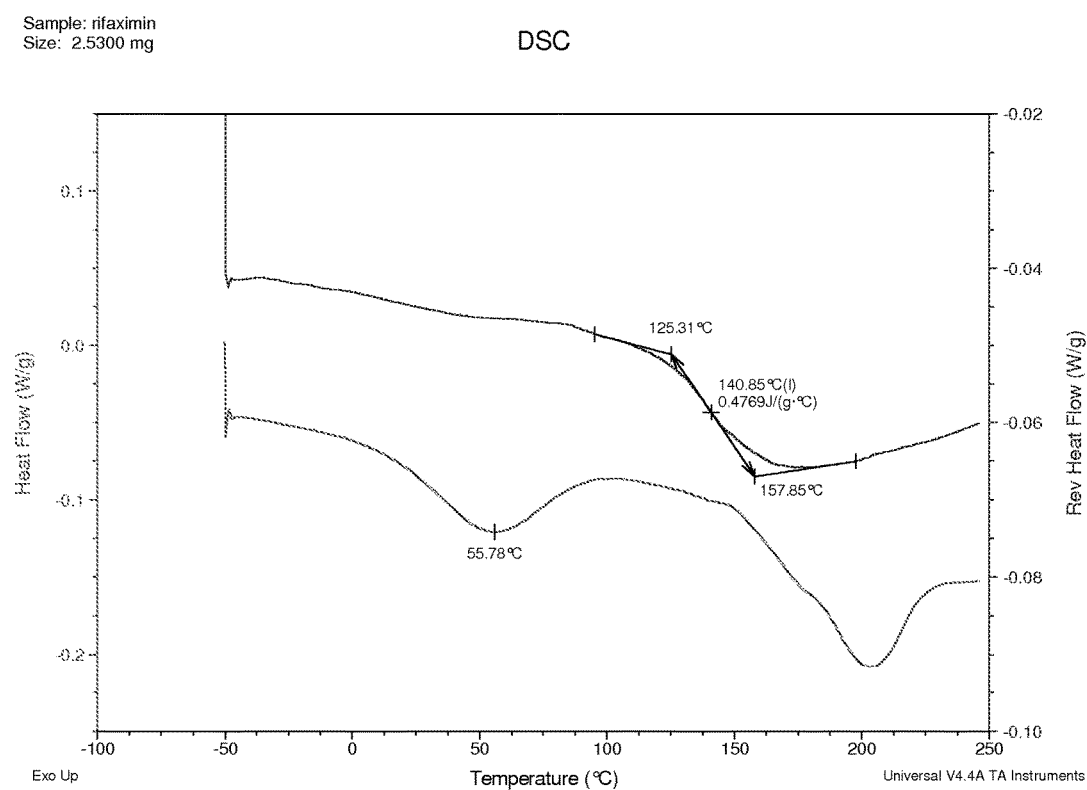
FIG. 23. mDSC thermogram for 25:75 (w/w) Rifaximin/Eudragit L100-55 dispersion obtained from methanol by spray drying.
Figure 24:
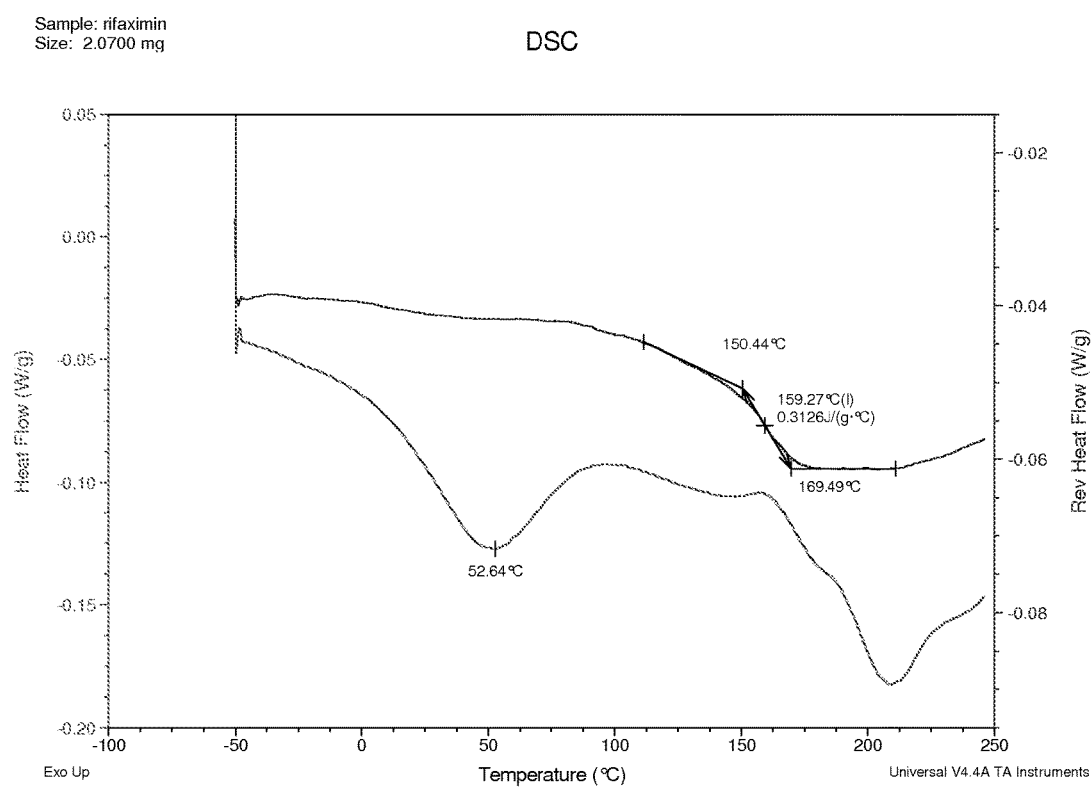
FIG. 24. mDSC thermogram for 50:50 (w/w) Rifaximin/Eudragit L100-55 dispersion obtained from methanol by spray drying.
Figure 26:
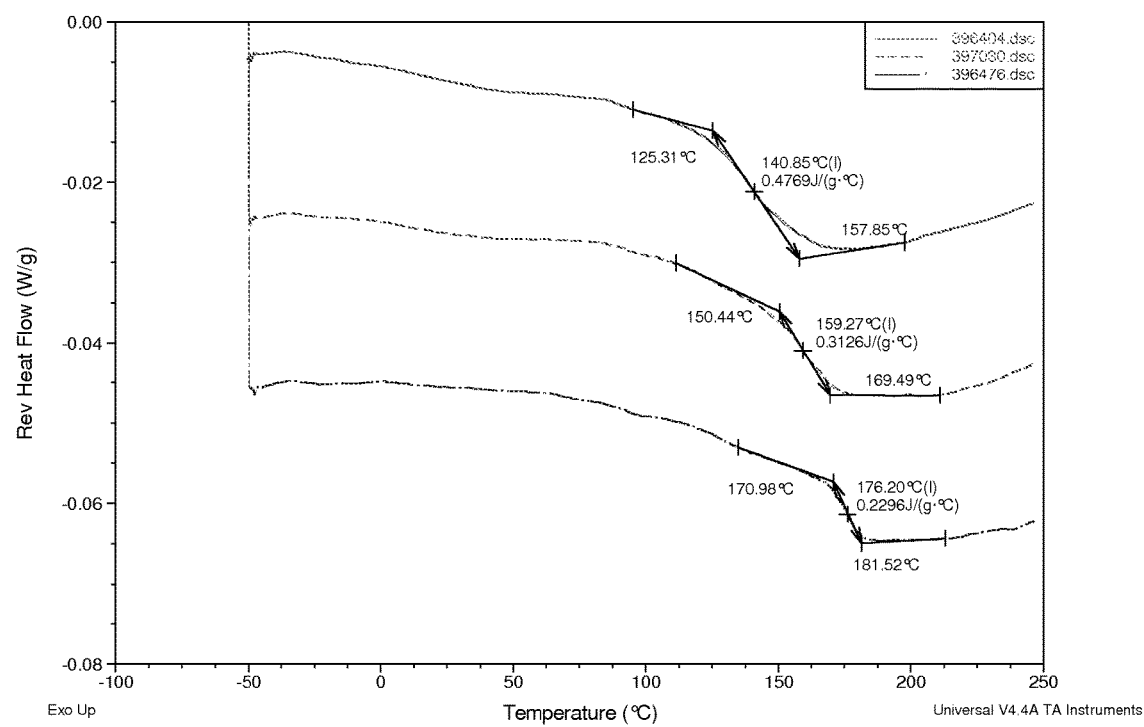
FIG. 26. Overlay of mDSC thermogram for Rifaximin/Eudragit L100-55 dispersions obtained from methanol by spray drying.

Similarly, as shown in FIG. 11 (with HPMC-P), FIG. 16 (with HPMC-AS HG), FIG. 21 (with HPMC-AS MG, and FIG. 26 (with Eudragit L100-55), Tg of material in each set of Rifaximin/polymer dispersions increases with the increased Rifaximin concentration due to the higher Tg of Rifaximin.

Physical Stability Assessment

An assessment of physical stability for rifaximin/polymer dispersions was conducted under stress conditions of aqueous solutions at different biologically relevant conditions, including 0.1N HCl solution at 37° C. and pH 6.5 FASSIF buffer at 37° C., elevated temperature/relative humidity (40° C./75% RH), and elevated temperature/dry (60° C.). The x-ray amorphous rifaximin—only sample prepared from methanol by spray drying was also stressed under the same conditions for comparison.

Stress in 0.1N HCl Solution at 37° C.

For the assessment of physical stability for samples in a 0.1N HCl solution maintained at 37° C., observations were made and microscopy images were acquired using polarized light at different time points including 0, 6 and 24 hrs, as summarized in Table 6. Based on the absence of birefringent particles when samples were observed by PLM, dispersions prepared with HPMC-AS HG and HPMC-AS MG display the highest physical stability under this particular stress condition. The results of this study for each of samples are discussed below.

X-ray amorphous Rifaximin stressed in 0.1N HCl solution at 37° C. at 0, 6, and 24 hrs showed evidence of birefringence/extinctions was observed at 6 hrs, indicating the occurrence of devitrification of the material.

Samples at compositions of 25:75 and 50:50 (w/w) crystallized at 6 hrs; sample at 75:25 (w/w) composition crystallized within 24 hrs while no evidence of crystallization was observed at 6 hrs or earlier. The decreased stability of Rifaximin/PVP K-90 dispersions in 0.1N HCl solution with increased PVP K-90 concentration may due to the high solubility of PVP K-90 in the solution.

Irregular aggregates without birefringence/extinctions were observed for dispersion prepared with HPMC-P at t=0 hr, the initial time point when 0.1N HCl solution was just added into solids. After 24 hrs, samples at compositions of 25:75 and 50:50 (w/w) remained as non-birefringent aggregates, indicating no occurrence of devitrification under the conditions examined. Evidence of crystallization was observed for sample of 75:25 (w/w) composition at 6 hrs. No birefringence/extinctions were observed for all of dispersions prepared with HPMC-AS HG and HPMC-AS MG after 24 hrs, suggesting these samples are resistant to devitrification upon exposure to 0.1N HCl solution for 24 hrs.

For dispersions prepared with Eudragit L100-55, upon exposure to 0.1N HCl solution for 24 hrs, birefringent particles with extinctions were observed only in the sample at 50:50 (w/w) composition. Considered that no evidence of crystallization was observed for dispersions of compositions at 25:75 and 75:25 (w/w), it is unknown whether such birefringence was caused by some foreign materials or by crystalline solids indicating the occurrence of devitrification.

Stress in pH 6.5 FASSIF Buffer at 37° C.

An assessment of physical stability of dispersions prepared was also performed in pH 6.5 FASSIF buffer maintained at 37° C. X-ray amorphous Rifaximin material was also stressed under same condition for comparison. PLM observations indicated that dispersions prepared from HPMC-AS HG and HPMC-AS MG display the highest physical stability under this stress condition. X-ray amorphous rifaximin-only material crystallized within 6 hrs, so did all rifaximin/PVP K-90 dispersions. For dispersions prepared with HPMC-P, birefringent particles with extinctions were observed in samples at 50:50 and 75:25 (w/w) compositions within 6 hrs, indicating the occurrence of devitrification in materials. No evidence of any birefringence/extinctions was observed in 25:75 (w/w) rifaximin/HPMC-P dispersion material after 24 hrs. No birefringence/extinctions were observed for all of dispersions prepared with HPMC-AS HG and HPMC-AS MG after 24 hrs, suggesting these samples are resistant to denitrification upon exposure to pH 6.5 FASSIF buffer for 24 hrs. Rifaximin/Eudragit L100-55 dispersions at 50:50 and 75:25 (w/w) compositions crystallized with 6 hrs while no evidence of crystallization was observed in the sample at 25:75 (w/w) composition after 24 hrs.

Stress at 40° C./75% RH Condition

The samples including all the dispersions and x-ray amorphous rifaximin-only material were assessed for evidence of crystallization based on observations by microscopy using polarized light. Each of the samples remained as irregular aggregates without birefringence/extinctions after stressed at 40° C./75% RH condition for 7 days.

Figure 27:
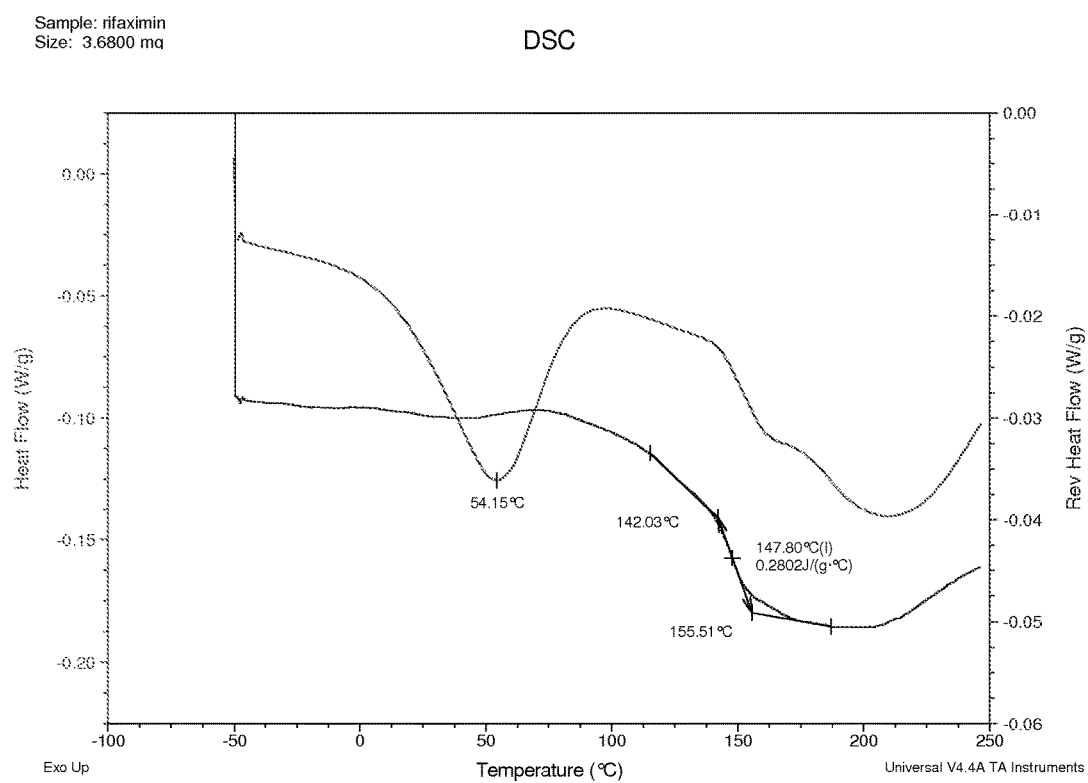
FIG. 27. mDSC thergram for 25:75 (w/w) Rifaximin/HPMC-P dispersion stressed at 40° C./75% RH for 7 d.
Figure 28:
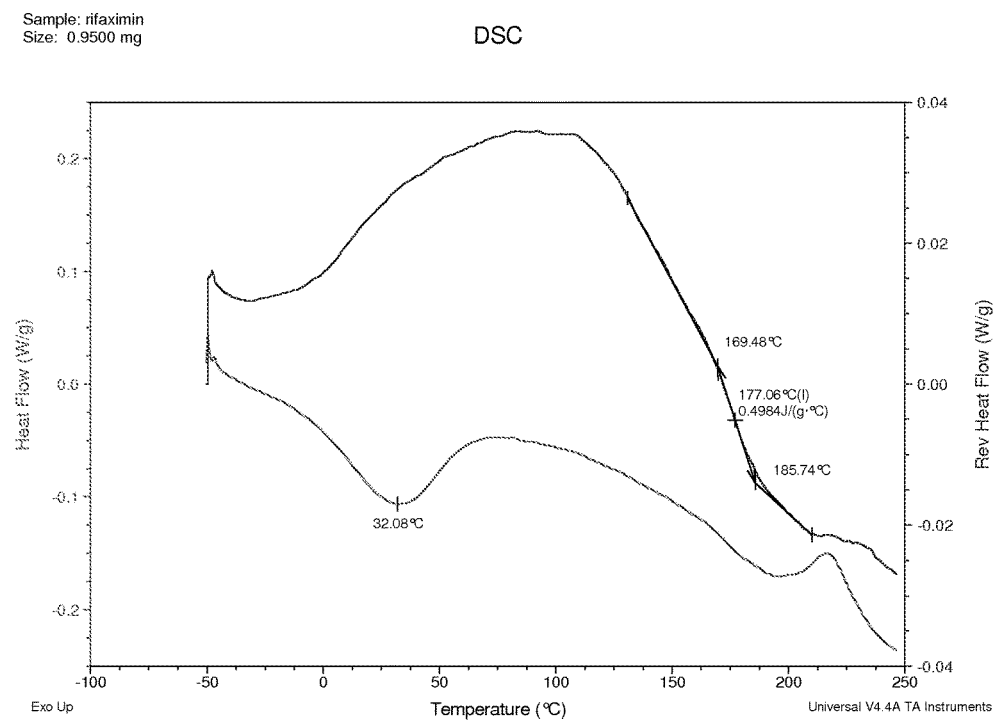
FIG. 28. mDSC thergram for 75:25 (w/w) Rifaximin/HPMC-AS HG dispersion stressed at 40° C./75% RH for 7 d.
Figure 29:
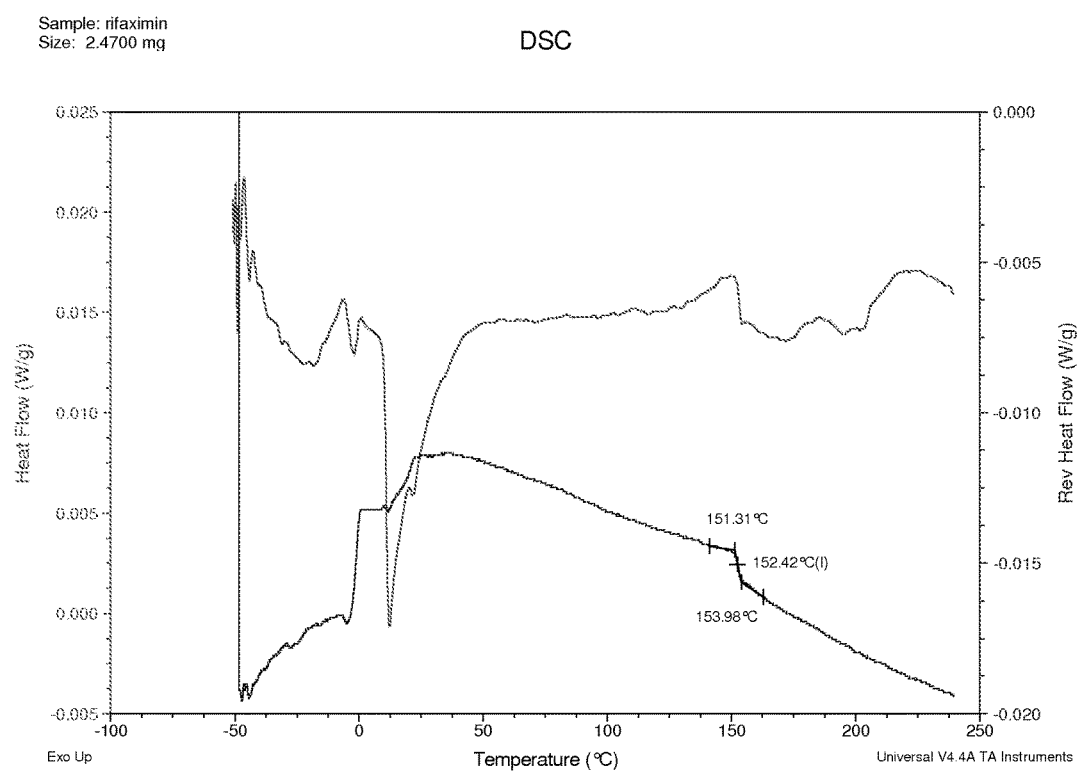
FIG. 29. mDSC thergram for 75:25 (w/w) Rifaximin/HPMC-AS MG dispersion stressed at 40° C./75% RH for 7 d.
Figure 30:
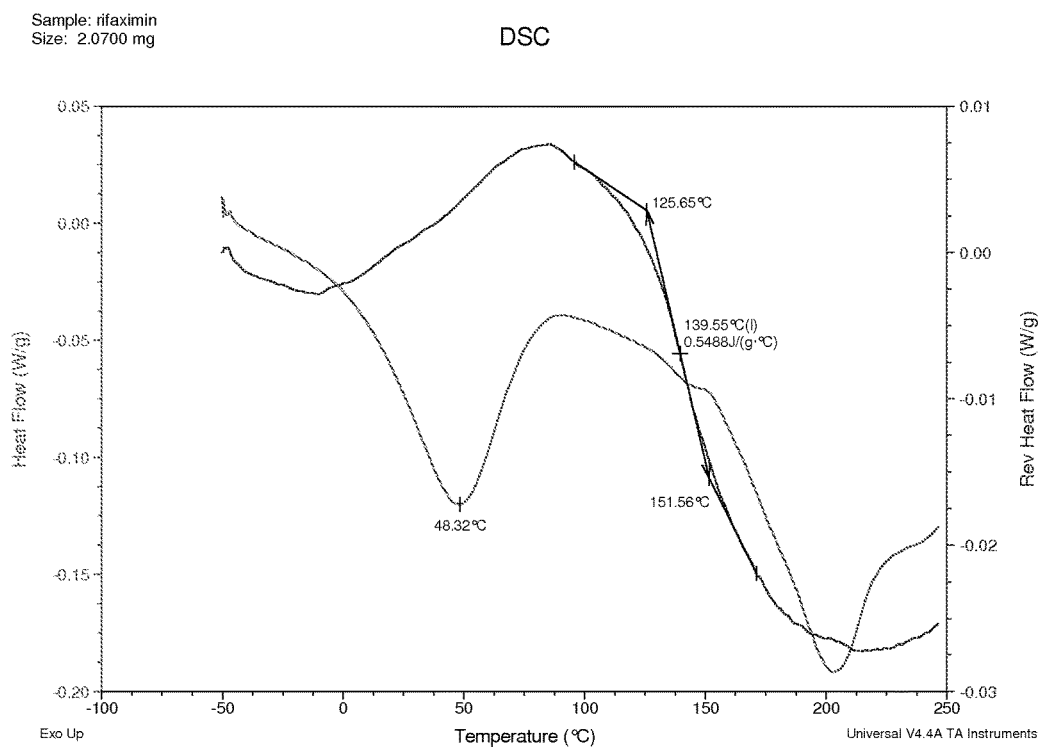
FIG. 30. mDSC thergram for 25:75 (w/w) Rifaximin/Eudragit L100-55 dispersion stressed at 40° C./75% RH for 7 d.

Modulated DSC analyses were carried out on selected samples including 25:75 (w/w) rifaximin/HPMC-P, 75:25 (w/w) rifaximin/HPMC-AS HG, 75:25 (w/w) rifaximin/HPMC-AS MG, and 25:75 (w/w) Rifaximin/Eudragit L100-55 to inspect for evidence of phase separation after exposure to 40° C./75% RH for 7 days. All of samples display a single apparent Tg at approximately 148° C. (FIG. 27, 25:75 (w/w) HPMC-P), 177° C. (FIG. 28, 75:25 (w/w) HPMC-AS HG) 152° C. (FIG. 29, 75:25 (w/w) HPMC-AS MG) and 140° C. (FIG. 30, 25:75 (w/w) Eudragit L100-55) respectively, indicating the components of each dispersion remained intimately miscible after stress. Although crimped with manual pin-hole DSC pan was used, the release of moisture from sample upon heating can still be observed from non-reversible heat flow signals.

Stress at 60° C./Dry Condition

All the dispersions and x-ray amorphous rifaximin-only material were also stressed at 60° C./dry condition for 7 days and were assessed for evidence of crystallization based on observations by microscopy using polarized light. Each of the samples remained as irregular aggregates without birefringence/extinctions after stressed at this condition for 7 days.

Rifaximin Solid Dispersions by Spray Drying

Figure 31:
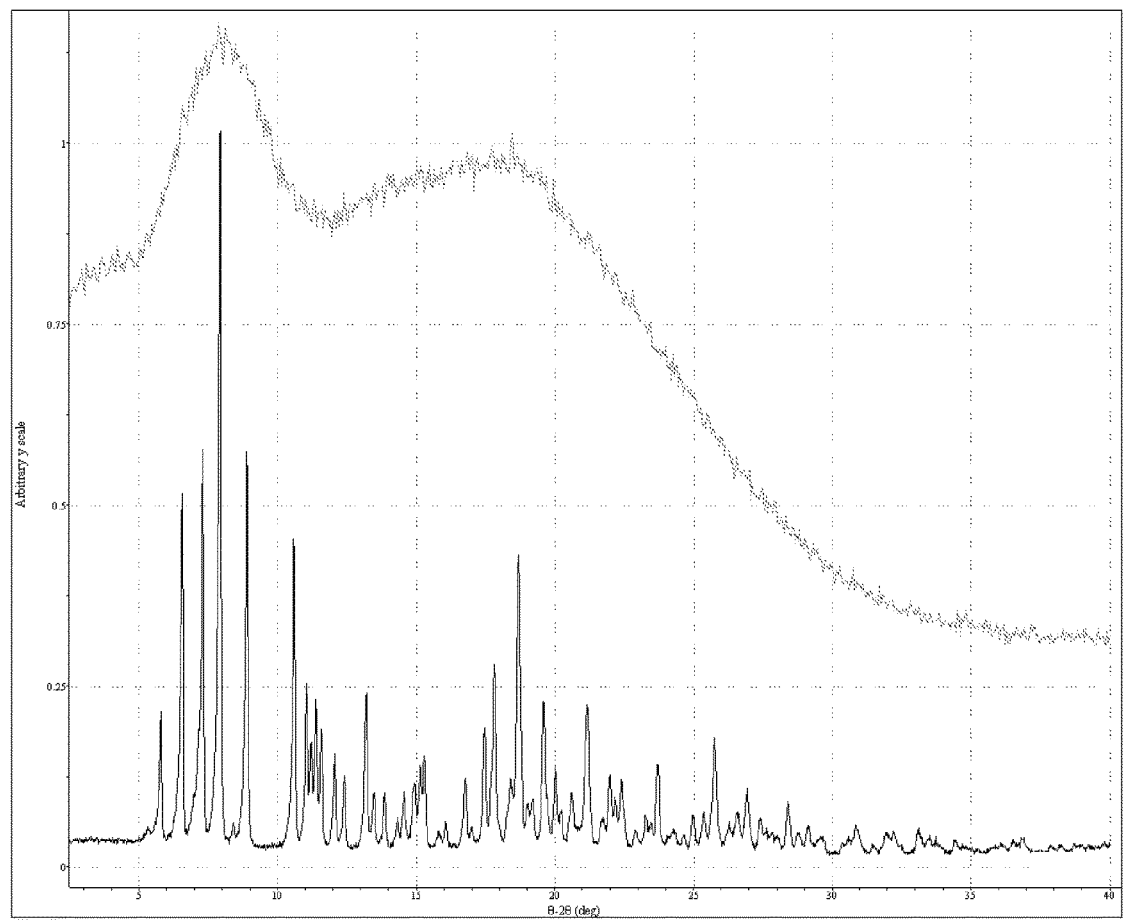
FIG. 31. XRPD pattern for 50:50 (w/w) Rifaximin/HPMC-AS MG dispersion.
Figure 36:
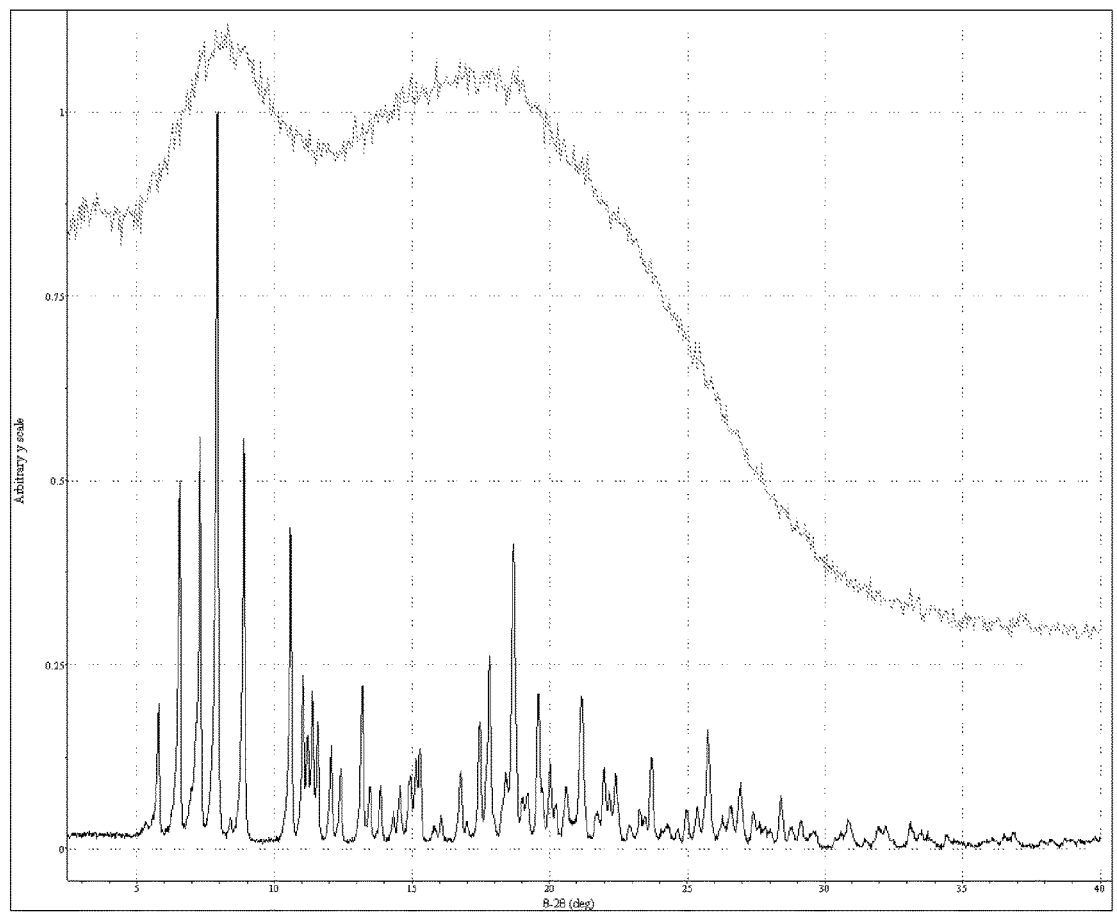
FIG. 36. XRPD pattern for 25:75 (w/w) Rifaximin/HPMC-P dispersion.

Based on the experimental results from screen, HPMC-AS MG and HPMC-P were used to prepare additional quantities of solid dispersions at gram-scale by spray drying. The operating parameters used for processing are presented in Table 9. Based on visual inspection, both dispersions were x-ray amorphous by XRPD (FIG. 31 and FIG. 36).

Characterization of 50:50 (w/w) Rifaximin/HPMC-AS MG Dispersion

Figure 32:
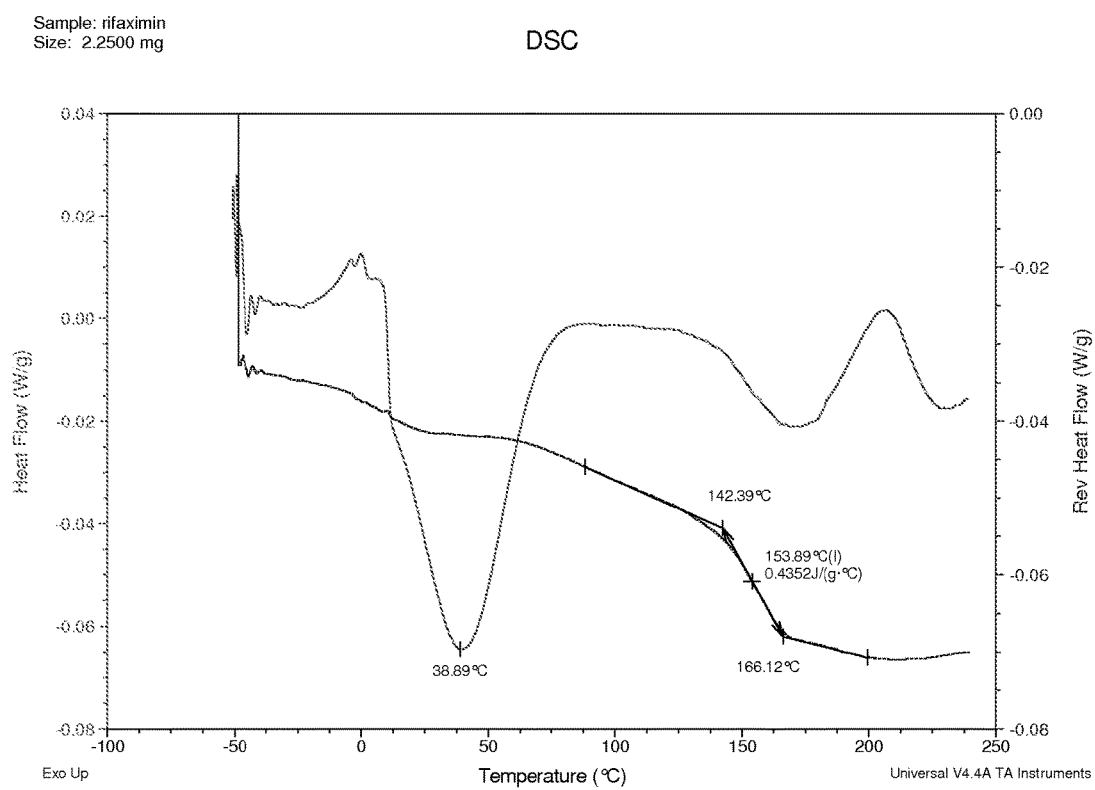
FIG. 32. Modulate DSC thermograms for 50:50 (w/w) Rifaximin/HPMC-AS MG dispersion.
Figure 33:
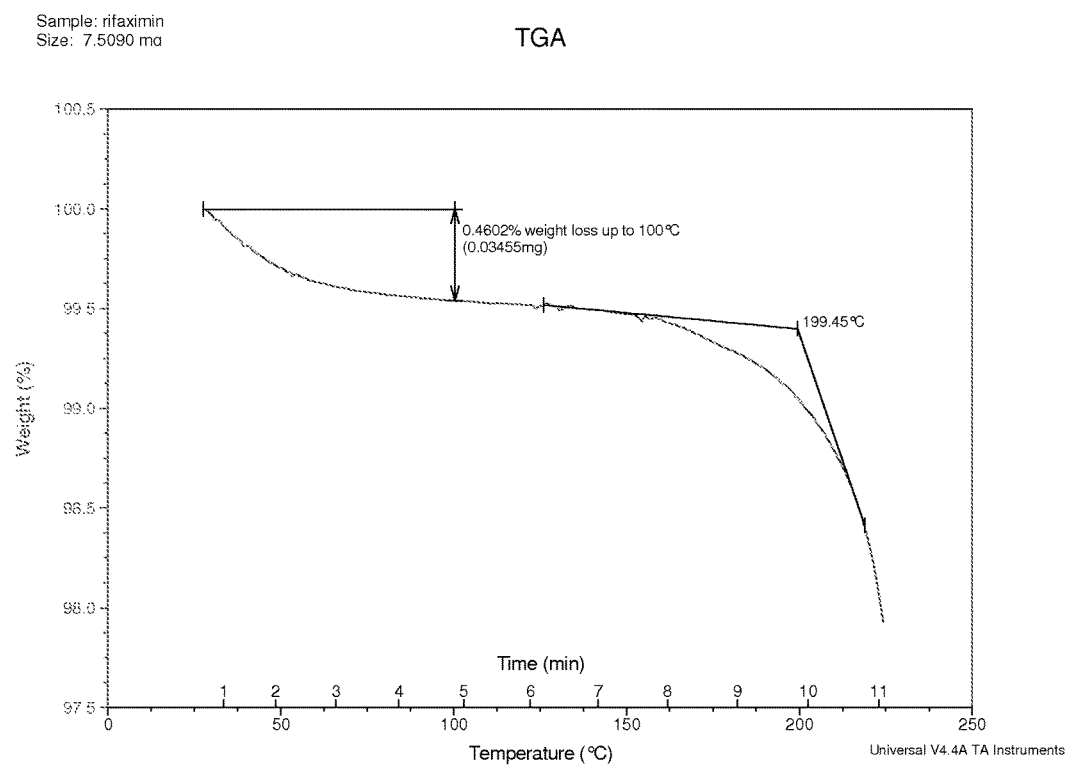
FIG. 33. TG-IR analysis for 50:50 (w/w) Rifaximin/HPMC-AS MG dispersion-TGA data.
Figure 34:
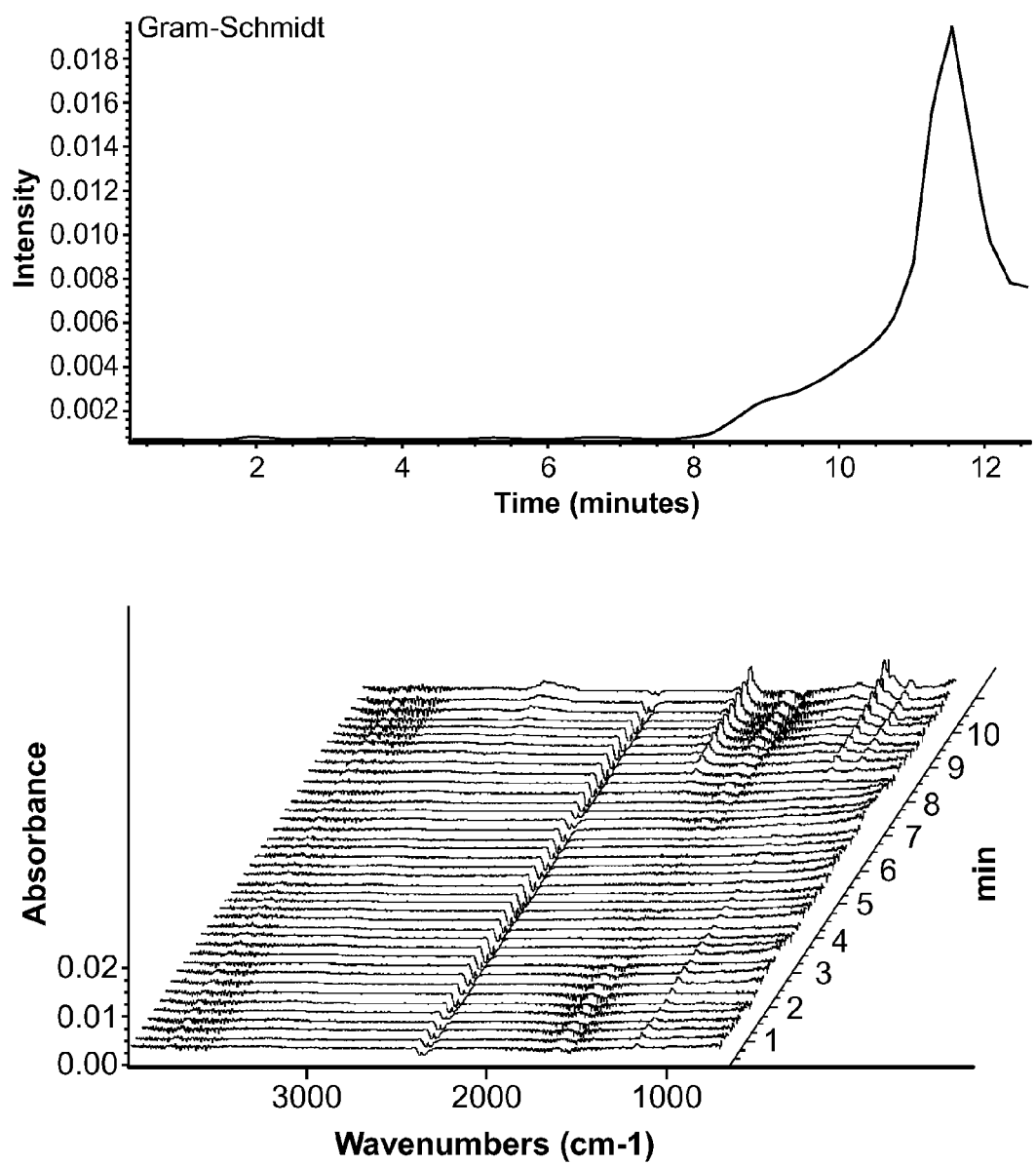
FIG. 34. TG-IR analysis for 50:50 (w/w) Rifaximin/HPMC-AS MG dispersion-Gram-Schmidt plot and waterfall plot.
Figure 35:
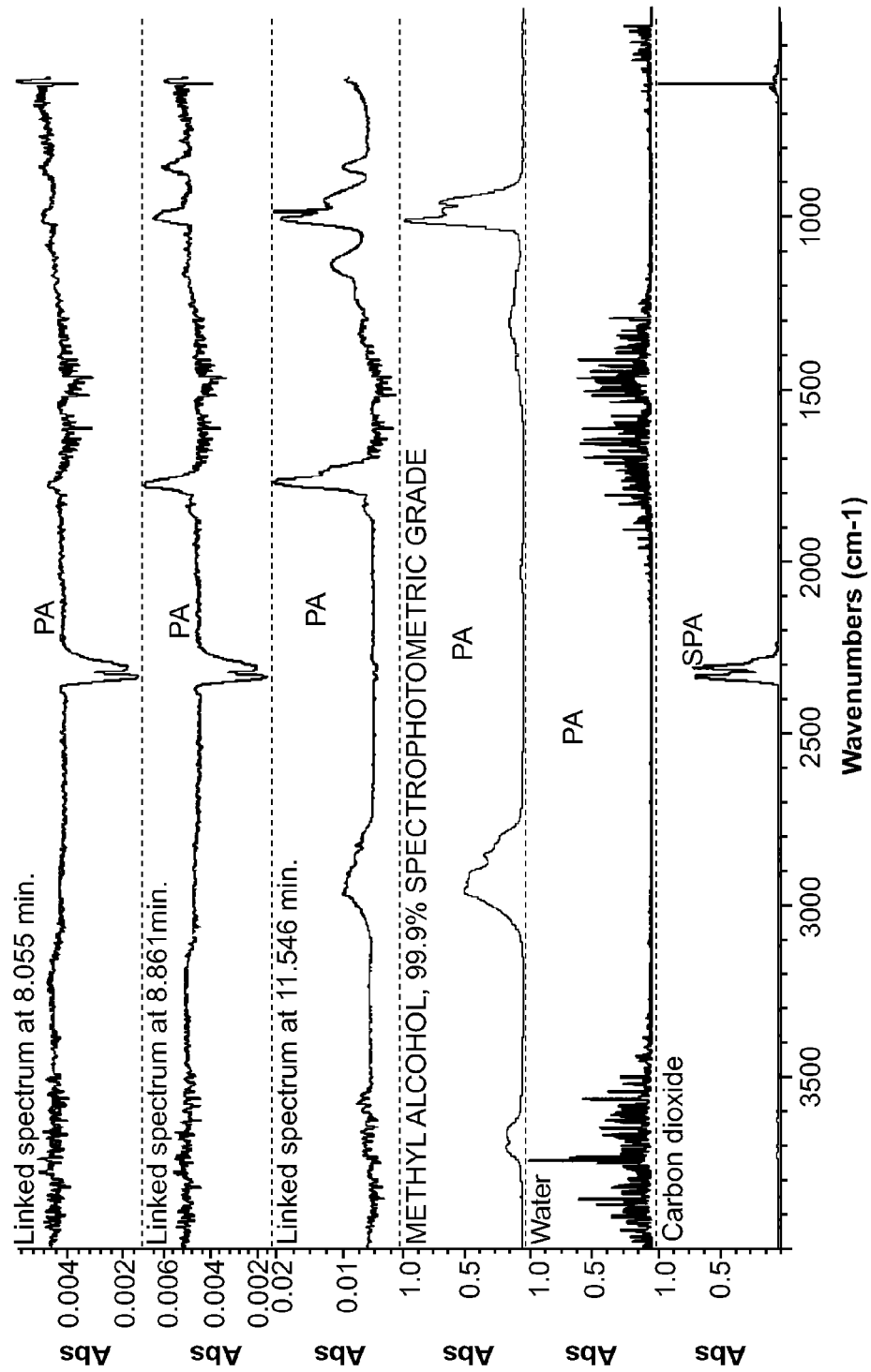
FIG. 35. TG-IR analysis for 50:50 (w/w) Rifaximin/HPMC-AS MG dispersion.

Characterization and results for the 50% API loading HPMC-AS MG are summarized in Table 10. The sample was x-ray amorphous based on high resolution XRPD. A single Tg at approximately 154° C. was observed from the apparent step change in the reversing heat flow signal in mDSC with the change of heat capacity 0.4 J/g ° C. A non-reversible endotherm was observed at approximately 39° C. which is likely due to the residual solvent in the materials (FIG. 32). TG-IR analysis was carried out in order to determine volatile content on heating. TGA data for this material is shown in FIG. 34. There was a 0.5% weight loss up to ~100° C. A Gram-Schmidt plot corresponding to the overall IR intensity associated with volatiles released by solids upon heating at 20° C./min is shown in FIG. 33. There was a dramatic increase of intensity of released volatiles after ~8 minutes, with a maximum at ~11.5 minutes. The waterfall plot (FIG. 34) and the linked IR spectrum (FIG. 35) are indicative of the loss of water loss up to ~8 minutes then methanol and some unknown volatiles thereafter. This is consistent with the dramatic change in the slope in the TGA and may indicate decomposition of material.

Characterization of 25:75 (w/w) Rifaximin/HPMC-P Dispersion

Figure 37:
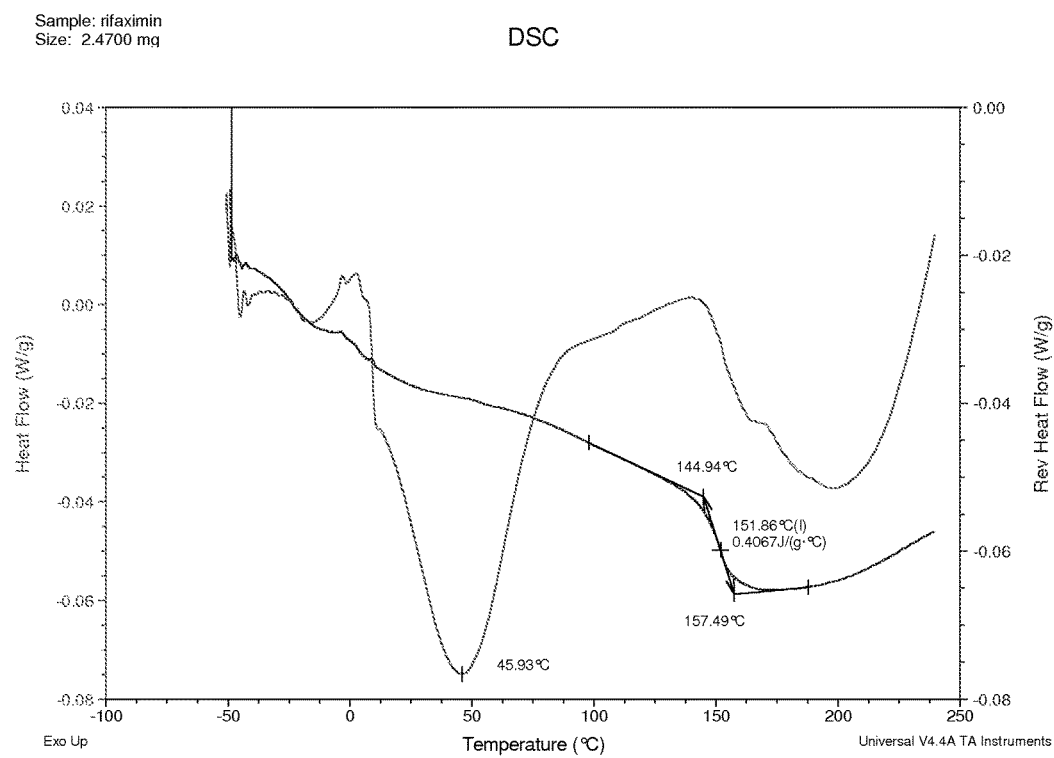
FIG. 37. Modulate DSC thermograms for 25:75 (w/w) Rifaximin/HPMC-P dispersion.
Figure 38:
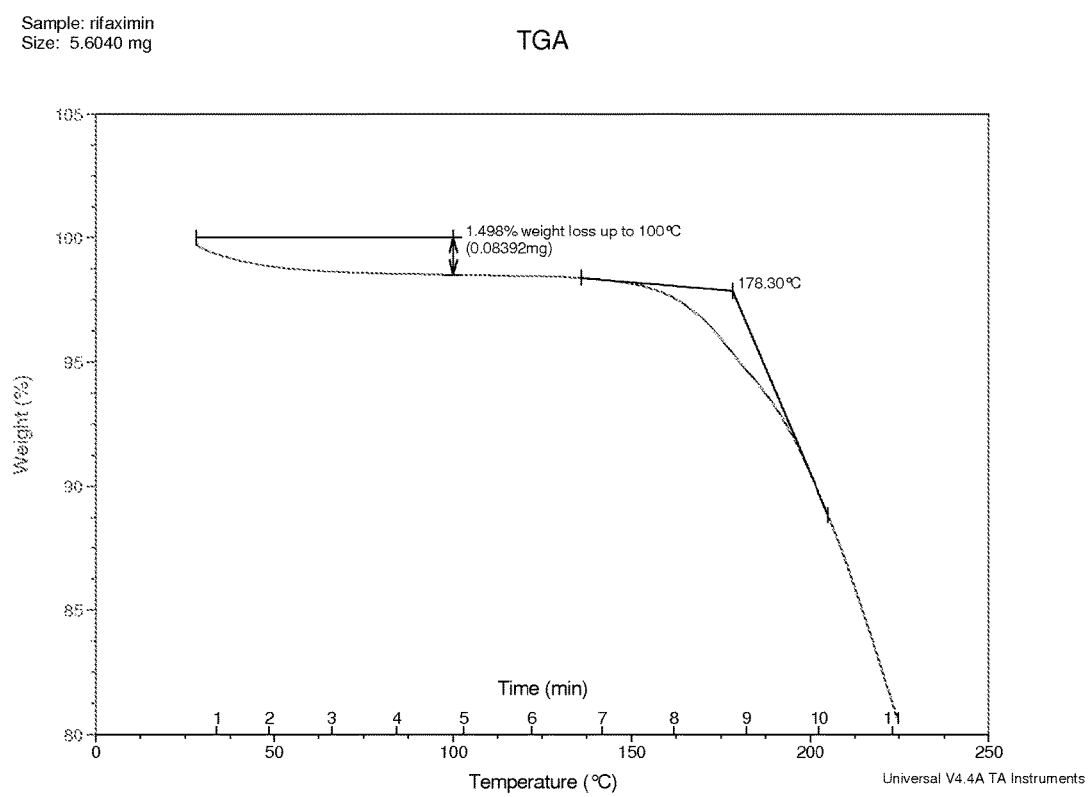
FIG. 38. TG-IR analysis for 25:75 (w/w) Rifaximin/HPMC-P dispersion-TGA data.
Figure 39:
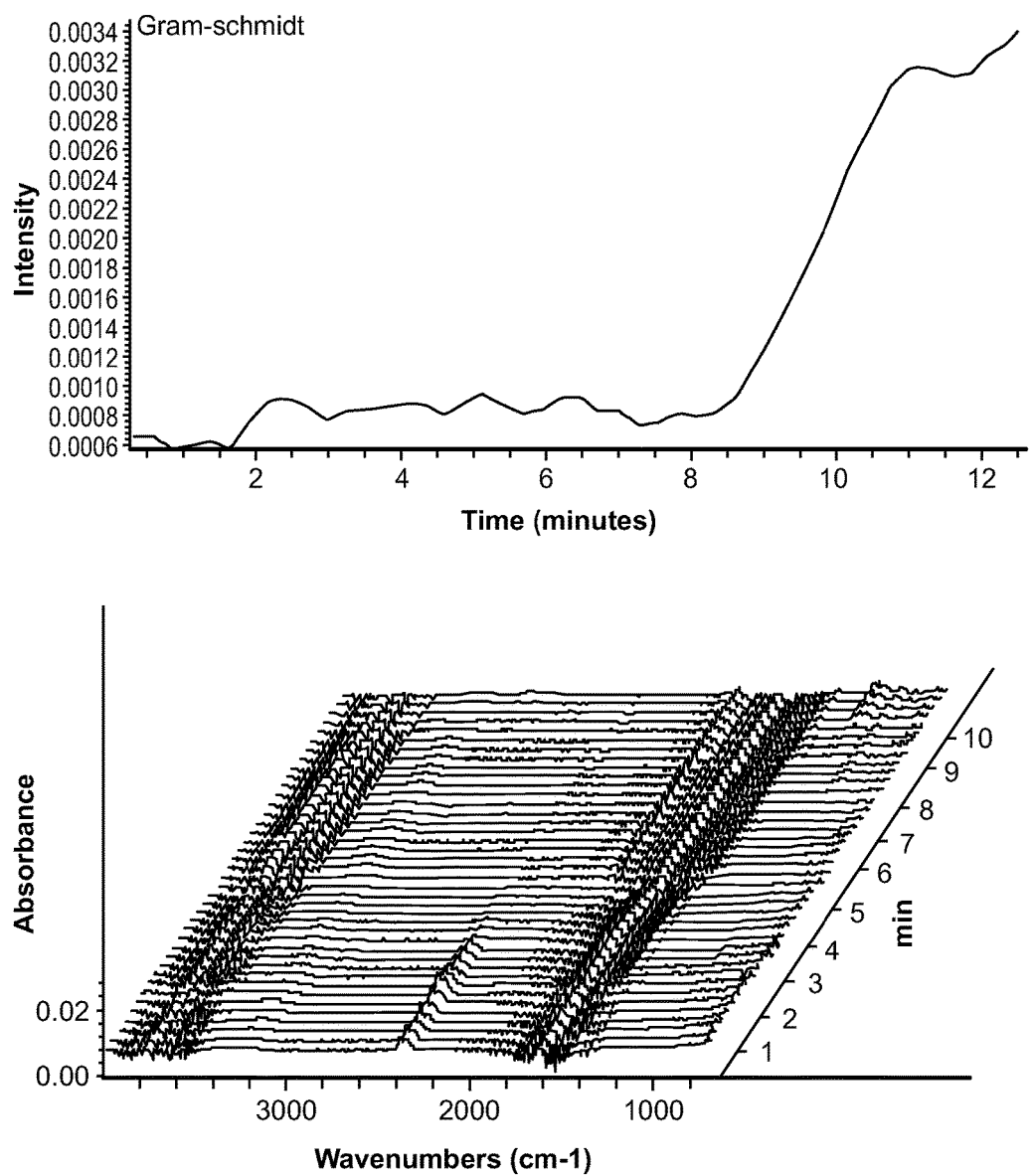
FIG. 39. TG-IR analysis for 25:75 (w/w) Rifaximin/HPMC-P dispersion-Gram-Schmidt plot and waterfall plot.
Figure 40:
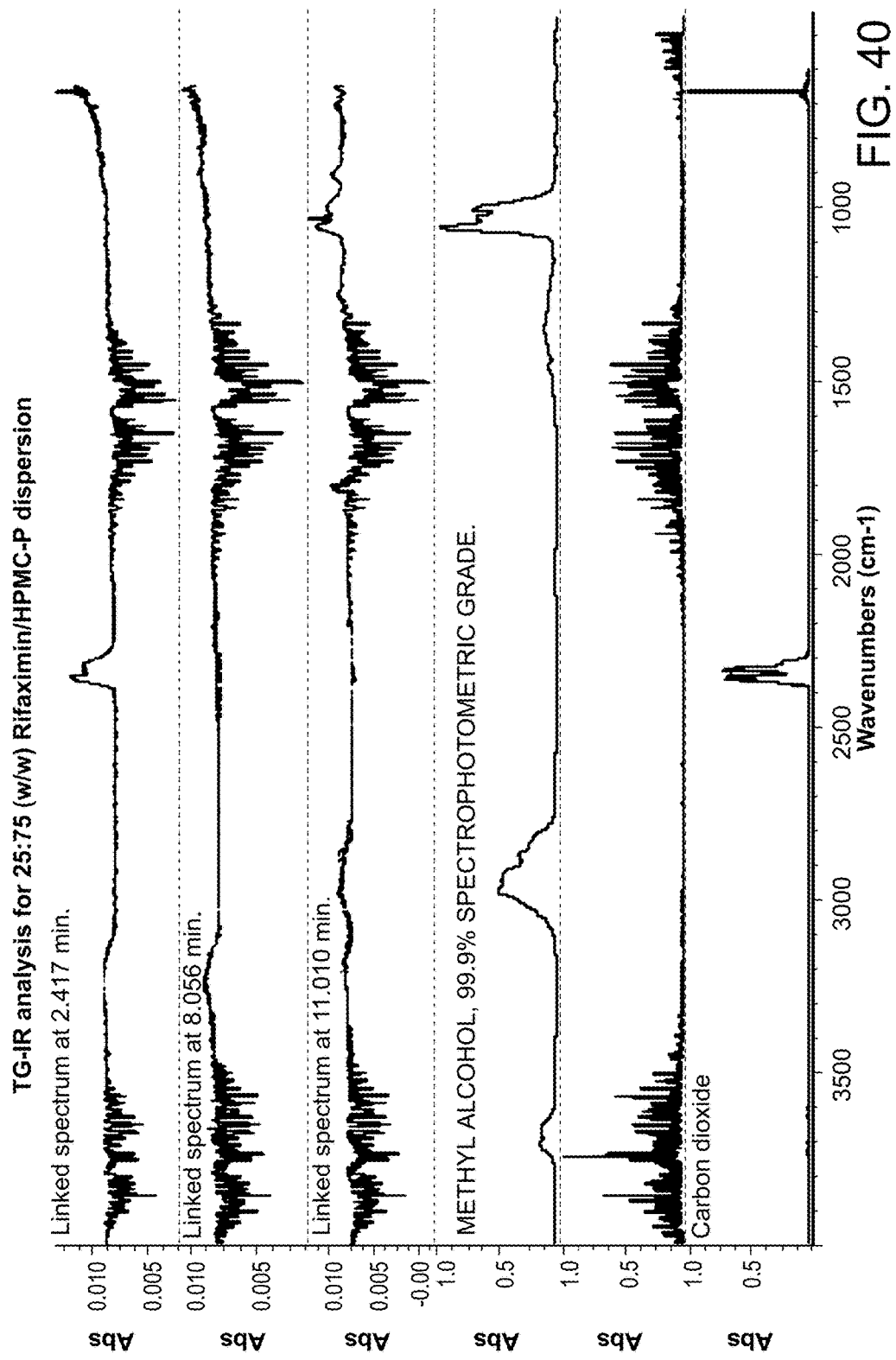
FIG. 40. TG-IR analysis for 25:75 (w/w) Rifaximin/HPMC-P dispersion.

Characterization and results for the 25% API loading dispersion of HPMC-P are summarized in Table 11. Solids were x-ray amorphous based on high resolution XRPD (FIG. 36). By mDSC, there is a single Tg at approximately 152° C. from the apparent step change in the reversing heat flow signal. The change of heat capacity is 0.4 J/g ° C. (FIG. 37). A non-reversible endotherm, which is likely due to the residual solvent in the materials, was observed at approximately 46° C. Volatiles generated on heating were analyzed by TG-IR. The total weight loss of sample was approximately 1.5 wt % to 100° C. and the dramatic change in the slope occurs at approximately 178° C. (FIG. 38). The Gram-Schmidt plot (FIG. 39) shows a small increase of intensity upon heating after ~2 minutes, followed by negligible change of intensity until ~9 minutes. Then dramatic change of intensity can be observed with a maximum at ~11 minutes, followed by a final increase of intensity above ~12 minutes. As seen in the waterfall plot (FIG. 39), some volatiles were released during entire heating period (data is shown in FIG. 40 using the linked IR spectrum at different time points as an example). The sample released water during entire heating period and methanol after ~9 minutes.

Dispersions Miscibility Study by Multivariate Mixture Analysis

Figure 41:
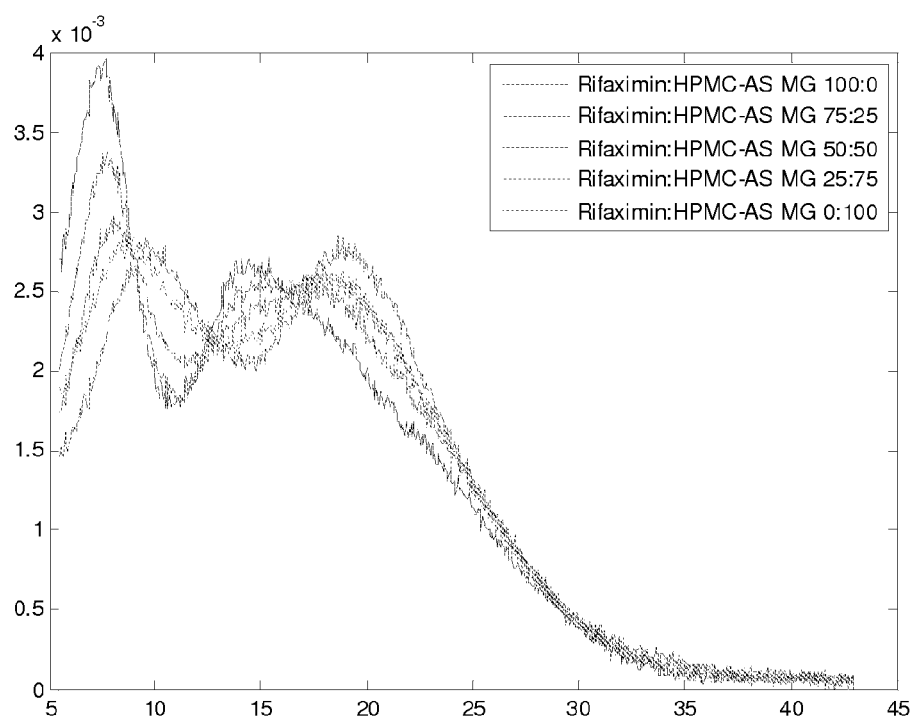
FIG. 41. Overlay of pre-processed XRPD patterns in multivariate mixture analysis.

For Rifaximin/HPMC-AS MG dispersions prepared by spray drying, a multivariate mixture analysis was performed using the XRPD data to examine the physical state of the components and inspect for evidence of miscibility. The analysis was done with MATLAB (v7.6.0) and Unscrambler (v 9.8) and it was not performed under cGMP guidelines. XRPD patterns of all the samples were truncated with their baseline corrected, and unit area normalized before analysis. The pre-possessed XRPD patterns are shown in FIG. 41.

Figure 42:
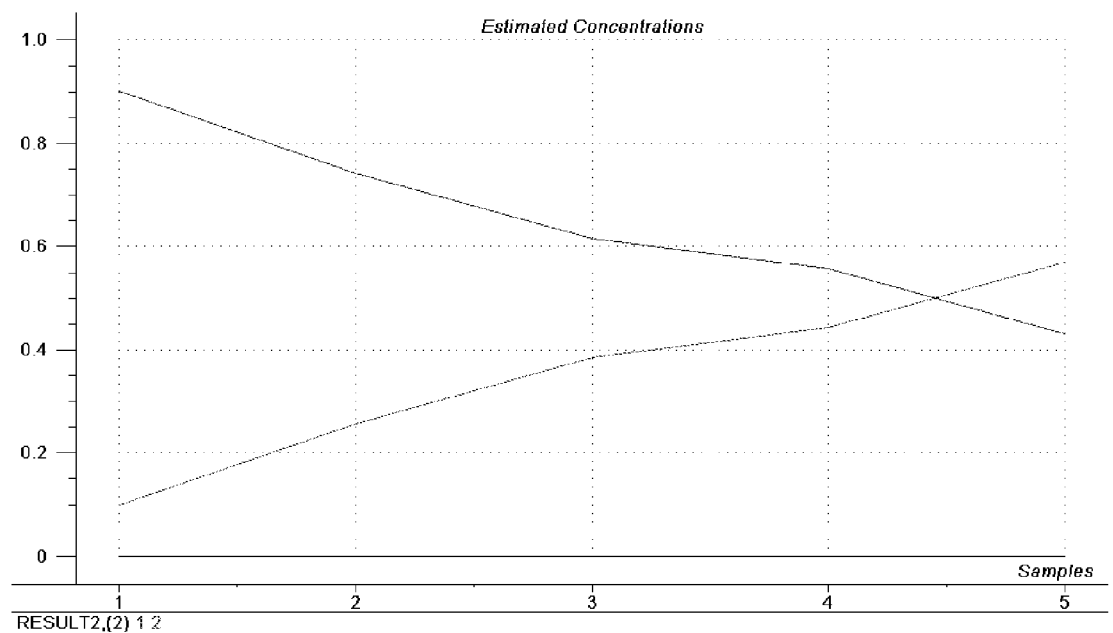
FIG. 42. Estimated Concentrations of Rifaximin (blue) and HPMC-AS MG (red) using Unscrambler MCR analysis.
Figure 43:
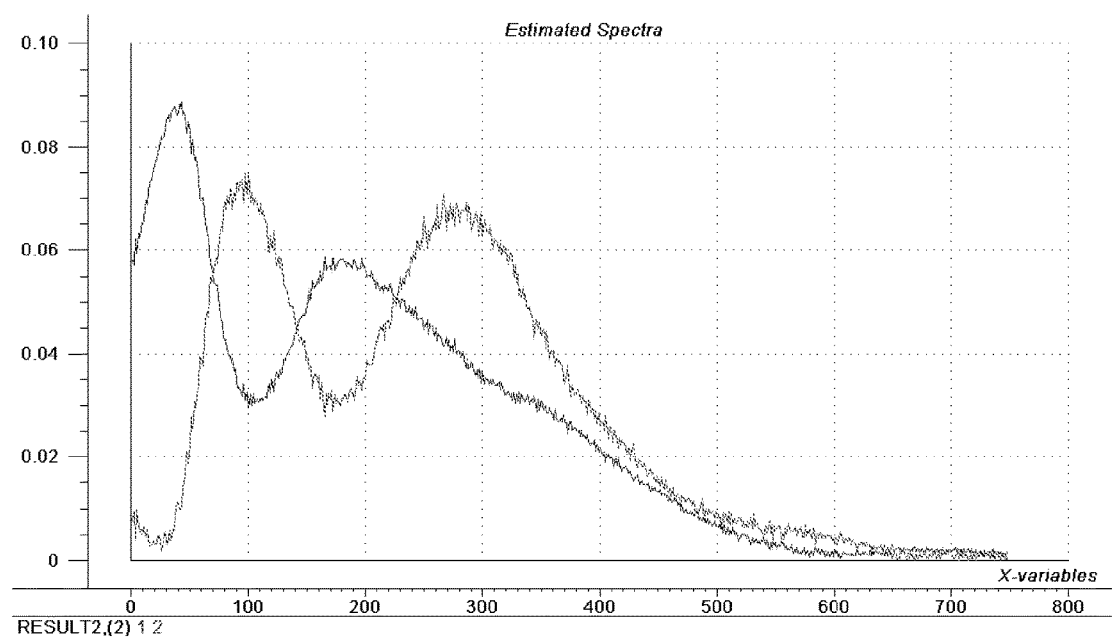
FIG. 43. Estimated XRPD patterns of Rifaximin (blue) and HPMC-AS MG (red) using Unscrambler MCR analysis.
Figure 44:
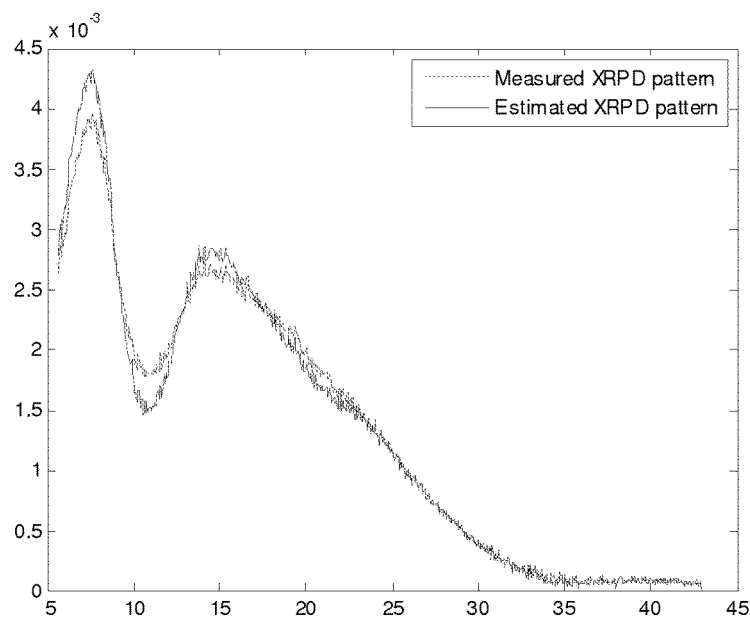
FIG. 44. Overlay of estimated XRPD pattern of pure rifaximin using MCR and measured XRPD pattern of 100% rifaximin.
Figure 45:
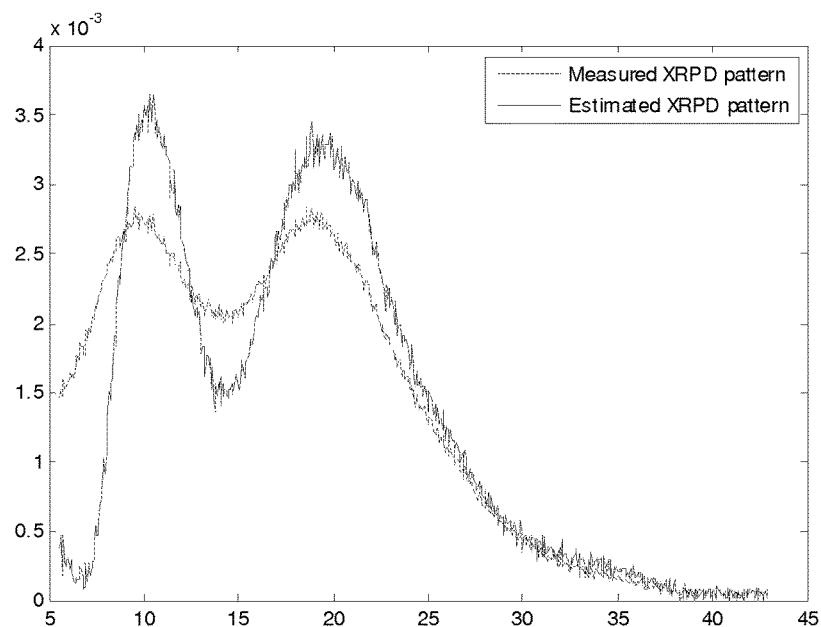
FIG. 45. Overlay of estimated XRPD pattern of pure HPMC-AS MG using MCR and measured XRPD pattern of 100% HPMC-AS MG.

In the analysis, Rifaximin and HPMC-AS MG were assumed to be separated phases (no miscibility) and the compositions of Rifaximin and HPMC-AS MG in each sample were estimated based on this assumption. As shown in FIG. 42, the estimated ratios of Rifaximin to HPMC-AS MG based on pure separated phases did not agree with samples actual compositions, especially for the samples with high compositions of HPMC-AS MG (low Rifaximin loading). Also, the calculated XRPD patterns for Rifaximin and HMPC-AS MG based on the assumption of separated phases (FIG. 43) compared to actual experimental XRPD patterns for Rifaximin (FIG. 44) and HPMC-AS MG (FIG. 45) were generated. Although the calculated Rifaximin pattern is similar to its experimental pattern, the calculated HMPC-AS MG pattern is quite different from its experimental pattern. Both results suggest that Rifaximin and HPMC-AS MG are not separated phases but miscible in the dispersions. The differences in the estimated and actual compositions are likely due to the interaction between Rifaximin and HPMC-AS MG.

TABLE 1

Solid Dispersion Attempts for Rifaximin/PVP K-90 by Spray Drying

| Description (a, b) | Habit/Description | Analysis | Result (c) |
|---|---|---|---|
| (25:75) PVP K-90 | solids orange; aggregates, irregular, no B/E | XRPD mDSC | x-ray amorph. 185° C. ($T_g$, midpoint); 0.3 J/g.° C. ($\Delta C_p$) |
| (50:50) PVP K-90 | solids orange; aggregates, irregular, no B/E | XRPD mDSC | x-ray amorph. 193° C. ($T_g$, midpoint); 0.3 J/g.° C. ($\Delta C_p$) |
| (75:25) PVP K-90 | solids orange; aggregates, irregular, no B/E | XRPD mDSC | x-ray amorph. 197° C. ($T_g$, midpoint); 0.3 J/g.° C. ($\Delta C_p$) |

(a): approximate ratio of Rifaximin to polymer, by weight;
(b): samples stored in freezer over desiccant after prepared.

TABLE 2

Solid Dispersion Attempts for Rifaximin/HPMC-P by Spray Drying

| Description (a, b) | Habit/Description | Analysis | Result (c) |
|---|---|---|---|
| (25:75) HPMC-P | solids light orange; aggregates, irregular, no B/E | XRPD mDSC | x-ray amorph. 153° C. ($T_g$, midpoint); 0.4 J/g.° C. ($\Delta C_p$) |
| (50:50) HPMC-P | solids orange; aggregates, irregular, no B/E | XRPD mDSC | x-ray amorph. 161° C. ($T_g$, midpoint); 0.4 J/g.° C. ($\Delta C_p$) |
| (75:25) HPMC-P | solids orange; aggregates, irregular, no B/E | XRPD mDSC | x-ray amorph. 174° C. ($T_g$, midpoint); 0.4 J/g.° C. ($\Delta C_p$) |

(a): approximate ratio of Rifaximin to polymer, by weight;
(b): samples stored in freezer over desiccant after prepared.

TABLE 3

Solid Dispersion Attempts for Rifaximin/HPMC-AS HG by Spray Drying

| Description (a, b) | Habit/Description | Analysis | Result (c) |
|---|---|---|---|
| (25:75) HPMC-AS HG | solids light orange; aggregates, irregular, no B/E | XRPD mDSC | x-ray amorph. 137° C. ($T_g$, midpoint); 0.4 J/g.° C. ($\Delta C_p$) |
| (50:50) HPMC-AS HG | solids orange; aggregates, irregular, no B/E | XRPD mDSC | x-ray amorph. 154° C. ($T_g$, midpoint); 0.4 J/g.° C. ($\Delta C_p$) |
| (75:25) HPMC-AS HG | solids orange; aggregates, irregular, no B/E | XRPD mDSC | x-ray amorph. 177° C. ($T_g$, midpoint); 0.3 J/g.° C. ($\Delta C_p$) |

(a): approximate ratio of Rifaximin to polymer, by weight;
(b): samples stored in freezer over desiccant after prepared.

TABLE 4

Solid Dispersion Attempts for Rifaximin/HPMC-AS MG by Spray Drying

| Description (a, b) | Habit/Description | Analysis | Result (c) |
|---|---|---|---|
| (25:75) HPMC-AS MG | solids light orange; aggregates, irregular, no B/E | XRPD mDSC | x-ray amorph. 140° C. ($T_g$, midpoint); 0.4 J/g.° C. ($\Delta C_p$) |
| (50:50) | solids orange; | XRPD | x-ray amorph. |

TABLE 4-continued

Solid Dispersion Attempts for Rifaximin/HPMC-AS MG by Spray Drying

| Description (a, b) | Habit/Description | Analysis | Result (c) |
|---|---|---|---|
| HPMC-AS MG (75:25) | aggregates, irregular, no B/E solids orange; | mDSC XRPD | 159° C. ($T_g$, midpoint); 0.4 J/g.° C. ($\Delta C_p$) x-ray amorph. |
| HPMC-AS MG | aggregates, irregular, no B/E | mDSC | 177° C. ($T_g$, midpoint); 0.3 J/g.° C. ($\Delta C_p$) |

(a): approximate ratio of Rifaximin to polymer, by weight;
(b): samples stored in freezer over desiccant after prepared.

TABLE 5

Solid Dispersion Attempts for Rifaximin/Eudragit L100-55 by Spray Drying

| Description (a, b) | Habit/Description | Analysis | Result (c) |
|---|---|---|---|
| (25:75) Eudragit L100-55 | solids light orange; aggregates, irregular, no B/E | XRPD mDSC | x-ray amorph. 141° C. ($T_g$, midpoint); 0.5 J/g.° C. ($\Delta C_p$) |
| (50:50) Eudragit L100-55 | solids orange; aggregates, irregular, no B/E | XRPD mDSC | x-ray amorph. 159° C. ($T_g$, midpoint); 0.3 J/g.° C. ($\Delta C_p$) |
| (75:25) Eudragit L100-55 | solids orange; aggregates, irregular, no B/E | XRPD mDSC | x-ray amorph. 176° C. ($T_g$, midpoint); 0.2 J/g.° C. ($\Delta C_p$) |

(a): approximate ratio of Rifaximin to polymer, by weight;
(b): samples stored in freezer over desiccant after prepared.

TABLE 6

Physical Stability Assessment in 0.1N HCl at 37° C. for Rifaximin and Rifaximin Dispersions Prepared in Methanol by Spray Drying

| Description (a) | Time (b) | Habit/Description | Analysis | Results |
|---|---|---|---|---|
| (100:0) Rifaximin-only | 0 | — | PLM | agg., irr., no B/E agg., irr., no B/E |
| | 6 hrs | orange solids, no liquid left | PLM | agg., no B/E + a few B/E particles clear view of B/E particles |
| | 24 hrs | orange solids, solution cloudy | PLM | agg., no B/E + a few B/E particles |
| (25:75) PVP K-90 | 0 | — | PLM | agg., irr., no B/E agg., irr., no B/E |
| | 6 hrs | orange solids, solution slightly yellow | PLM | agg., no B/E + B/E particles clear view of B/E particles |
| | 24 hrs | orange solids, solution slightly yellow | PLM | agg., no B/E + B/E particles |
| (50:50) PVP K-90 | 0 | — | PLM | agg., irr., no B/E agg., irr., no B/E |
| | 6 hrs | orange solids, solution slightly yellow | PLM | agg., no B/E + a few B/E particles clear view of B/E particles |
| | 24 hrs | orange solids, small amount of liquid left | PLM | majority agg., no B/E + a few B/E particles clear view of B/E particles |
| (75:25) PVP K-90 | 0 | — | PLM | agg., irr., no B/E agg., irr., no B/E |
| | 6 hrs | orange solids, solution slightly yellow | PLM | agg., no B/E agg., no B/E |
| | 24 hrs | orange solids, small amount of liquid left | PLM | agg., no B/E a few B/E particles in view field |
| (25:75) HPMC-P | 0 | — | PLM | agg., irr., no B/E agg., irr., no B/E |
| | 6 hrs | light orange solids, liquid turbid | PLM | agg., no B/E agg., no B/E |
| | 24 hrs | orange solids, liquid turbid | PLM | agg., no B/E agg., no B/E |
| (50:50) HPMC-P | 0 | — | PLM | agg., irr., no B/E agg., irr., no B/E |
| | 6 hrs | orange solids, liquid turbid | PLM | agg., no B/E agg., no B/E |
| | 24 hrs | orange solids, solution cloudy | PLM | agg., no B/E agg., no B/E |
| (75:25) HPMC-P | 0 | — | PLM | agg., irr., no B/E agg., irr., no B/E |
| | 6 hrs | orange solids, liquid turbid | PLM | agg., no B/E + some B/E particles clear view of B/E particles |
| | 24 hrs | orange solids, small amount of liquid left | PLM | B/E particles observed clear view of B/E particles |

TABLE 6-continued

Physical Stability Assessment in 0.1N HCl at 37° C. for Rifaximin and
Rifaximin Dispersions Prepared in Methanol by Spray Drying

| Description (a) | Time (b) | Habit/Description | Analysis | Results |
|---|---|---|---|---|
| (25:75) HPMC-AS HG | 0 | — | PLM | agg., irr., no B/E<br>agg., irr., no B/E |
| | 6 hrs | light orange solids in cloudy liquid | PLM | no B/E observed<br>no B/E observed |
| | 24 hrs | orange solids in cloudy solution | PLM | no B/E observed<br>no B/E observed |
| (50:50) HPMC-AS HG | 0 | — | PLM | agg., irr., no B/E<br>agg., irr., no B/E |
| | 6 hrs | orange solids, liquid cloudy | PLM | no B/E observed<br>no B/E observed |
| | 24 hrs | orange solids in cloudy solution | PLM | no B/E observed<br>no B/E observed |
| (75:25) HPMC-AS HG | 0 | — | PLM | agg., irr., no B/E<br>agg., irr., no B/E |
| | 6 hrs | orange solids, liquid turbid | PLM | no B/E observed<br>no B/E observed |
| | 24 hrs | orange solids + cloudy solution | PLM | agg., no B/E<br>agg., no B/E |
| (25:75) HPMC-AS MG | 0 | — | PLM | agg., irr., no B/E<br>agg., irr., no B/E |
| | 6 hrs | light orange solids in cloudy liquid | PLM | no B/E observed<br>majority no B/E, a few B/E particles |
| | 24 hrs | orange solids in cloudy liquid | PLM | B/E particles seems fiber-like, may due to foreign materials |
| (50:50) HPMC-AS MG | 0 | — | PLM | agg., irr., no B/E<br>agg., irr., no B/E |
| | 6 hrs | orange solids, liquid turbid | PLM | agg., no B/E + a few B/E particles seems due to foreign material<br>clear view of B/E particles |
| | 24 hrs | orange solids in cloudy solution | PLM | no B/E observed<br>no B/E observed |
| (75:25) HPMC-AS MG | 0 | — | PLM | agg., irr., no B/E<br>agg., irr., no B/E |
| | 6 hrs | orange solids, liquid turbid | PLM | no B/E observed<br>no B/E observed |
| | 24 hrs | orange solids in cloudy liquid | PLM | no B/E observed<br>agg., no B/E |
| (25:75) Eudragit L100-55 | 0 | — | PLM | agg., irr., no B/E<br>agg., irr., no B/E |
| | 6 hrs | light orange solids in cloudy liquid | PLM | no B/E observed |
| | 24 hrs | orange solids in cloudy solution | PLM | no B/E observed |
| (50:50) Eudragit L100-55 | 0 | — | PLM | agg., irr., no B/E<br>agg., irr., no B/E |
| | 6 hrs | orange solids in cloudy liquid | PLM | no B/E observed except 2 particles |
| | 24 hrs | orange solids in cloudy solution | PLM | majority no B/E, a few B/E particles in center<br>clear view of B/E particles |
| (75:25) Eudragit L100-55 | 0 | — | PLM | agg., irr., no B/E<br>agg., irr., no B/E |
| | 6 hrs | orange solids, liquid turbid | PLM | agg., no B/E<br>agg., no B/E |
| | 24 hrs | orange solids in cloudy liquid | PLM | agg., no B/E |

(a): approximate ratio of Rifaximin to polymer, by weight.
(b): time is cumulative and approximate; 100 μL of 0.1N HCl solution added into samples at t = 0.
(c): 100 μL of 0.1N HCl solution added into the sample after PLM analysis at 6 hrs.

TABLE 7

Physical Stability Assessment at 40° C./75% RH/7 d Condition for Rifaximin and Rifaximin Dispersions Prepared in Methanol by Spray Drying

| Description (a) | Habit/Description | Analysis | Results |
|---|---|---|---|
| (100:0) Rifaximin-only | orange solids, dry | PLM | agg., irr., no B/E |
| (25:75) PVP K-90 | dark yellow solids, dry | PLM | agg., irr., no B/E |
| (50:50) PVP K-90 | orange solids, dry | PLM | agg., irr., no B/E |
| (75:25) PVP K-90 | orange solids, dry | PLM | agg., irr., no B/E |
| (25:75) HPMC-P | light orange solids, dry | PLM mDSC | agg., irr., no B/E 148° C. ($T_g$, midpoint); 0.3 J/g.° C. ($\Delta C_p$) |
| (50:50) HPMC-P | orange solids, dry | PLM | agg., irr., no B/E |
| (75:25) HPMC-P | orange solids, dry | PLM | agg., irr., no B/E |
| (25:75) HPMC-AS HG | light orange solids, dry | PLM | agg., irr., no B/E |
| (50:50) HPMC-AS HG | orange solids, dry | PLM | agg., irr., no B/E |
| (75:25) HPMC-AS HG | orange solids, dry | PLM mDSC | agg., irr., no B/E 177° C. ($T_g$, midpoint); 0.5 J/g.° C. ($\Delta C_p$) |
| (25:75) HPMC-AS MG | light orange solids, dry | PLM | agg., irr., no B/E |
| (50:50) HPMC-AS MG | orange solids, dry | PLM | agg., irr., no B/E |
| (75:25) HPMC-AS MG | orange solids, dry | PLM mDSC | agg., irr., no B/E 152° C. ($T_g$, midpoint) |
| (25:75) Eudragit L100-55 | light orange solids, dry | PLM mDSC | agg., irr., no B/E 140° C. ($T_g$, midpoint); 0.5 J/g.° C. ($\Delta C_p$) |
| (50:50) Eudragit L100-55 | orange solids, dry | PLM | agg., irr., no B/E |
| (75:25) Eudragit L100-55 | orange solids, dry | PLM | agg., irr., no B/E |

(a): approximate ratio of Rifaximin to polymer, by weight.
(b): analysis treated as non-cGMP.

TABLE 8

Physical Stability Assessment at 60° C./Dry/7 d Condition for Rifaximin and Rifaximin Dispersions Prepared in Methanol by Spray Drying

| Description (a) | Habit/Description | Analysis | Results |
|---|---|---|---|
| (100:0) Rifaximin-only | orange solids | PLM | agg., irr., no B/E |
| (25:75) PVP K-90 | orange solids | PLM | agg., irr., no B/E |
| (50:50) PVP K-90 | orange solids | PLM | agg., irr., no B/E |
| (75:25) PVP K-90 | orange solids | PLM | agg., irr., no B/E |
| (25:75) HPMC-P | light orange solids | PLM | agg., irr., no B/E |
| (50:50) HPMC-P | orange solids | PLM | agg., irr., no B/E |
| (75:25) HPMC-P | orange solids | PLM | agg., irr., no B/E |
| (25:75) HPMC-AS HG | light orange solids | PLM | agg., irr., no B/E |
| (50:50) HPMC-AS HG | orange solids | PLM | agg., irr., no B/E |
| (75:25) HPMC-AS HG | orange solids | PLM | agg., irr., no B/E |
| (25:75) HPMC-AS MG | light orange solids | PLM | agg., irr., no B/E |
| (50:50) HPMC-AS MG | orange solids | PLM | agg., irr., no B/E |
| (75:25) HPMC-AS MG | orange solids | PLM | agg., irr., no B/E |
| (25:75) Eudragit L100-55 | light orange solids | PLM | agg., irr., no B/E |
| (50:50) Eudragit L100-55 | orange solids | PLM | agg., irr., no B/E |
| (75:25) Eudragit L100-55 | orange solids | PLM | agg., irr., no B/E |

(a): approximate ratio of Rifaximin to polymer, by weight.

TABLE 9

Parameters for Rifaximin Solid Dispersions by Spray Drying

| Description (a) | Inlet temp. (set, ° C.) | Aspirator % | Pump % | Inlet temp. (measured, ° C.) | Outlet temp. (measured, ° C.) | Spray rate (b) mL/min |
|---|---|---|---|---|---|---|
| (50:50) HPMC-AS MG, ~10 g scale | 120 | 95 | 40-30 | 120-119 | 60-45 | 9.6 |
| (25:75) HPMC-P, ~10 g scale | 120 | 95 | 45-30 | 120-119 | 55-43 | 9.7 |

(a): approximate ratio of Rifaximin to polymer, by weight.
(b): flow rates are estimated at 30% pump.

TABLE 10

Characterizations of 50:50 (w/w) Rifaximin/HPMC-AS MG Dispersion by Spray Drying

| Analysis | Results |
|---|---|
| XRPD | x-ray amorphous |
| mDSC | 154° C. (midpoint, $T_g$) 0.4 J/g.° C. ($\Delta C_p$) |
| TG-IR | 0.5 wt % (loss up to 100° C.) 199° C. (onset, apparent decomp.) water, methanol and unknown volatiles |

TABLE 11

Characterizations of 25:75 (w/w) Rifaximin/HPMC-P Dispersion by Spray Drying

| Analysis | Results |
|---|---|
| XRPD | x-ray amorphous |
| mDSC | 152° C. (midpoint, $T_g$) 0.4 J/g.° C. ($\Delta C_p$) |
| TG-IR | 1.5 wt % (loss up to 100° C.) 178° C. (onset, apparent decomp.) water and methanol |

TABLE 12

Sample Information of Rifaximin Dispersions for Dissolution Test in pH 6.52 FASSIF Buffer at 37° C.

| Description (a) | Sample ID | Dissolution Vessel No | Solids Weight (mg) | Volume of Buffer (mL) |
|---|---|---|---|---|
| (50:50) HPMC-AS MG | 4042-97-01 | 1 | 122.1 | 300 |
| | | 2 | 120.5 | |
| | | 3 | 121.4 | |
| (25:75) HPMC-P | 4103-01-01 | 4 | 242.5 | 300 |
| | | 5 | 239.2 | |
| | | 6 | 242.4 | |

(a): approximate ratio of Rifaximin to polymer, by weight.

TABLE 13

Rifaximin Concentrations of 50:50 (w/w) Rifaximin/HPMC-AS MG Dispersion in pH 6.52 FASSIF Buffer at 37° C.

| Dissolution Vessel No | Time (min.) | Dilution (c) | Absorbance (d) | Concentration (µg/mL) |
|---|---|---|---|---|
| 1 | 5 | — | 0.0159 | 0.34 |
| | 10 | — | 0.0346 | 2.53 |
| | 15 | — | 0.0569 | 5.13 |
| | 30 | — | 0.09655 | 9.75 |
| | 60 | — | 0.1626 | 17.46 |
| | 90 | — | 0.2216 | 24.35 |
| | 120 | — | 0.25625 | 28.39 |
| | 1440 | 4 | 0.4093 | 184.99 |
| 2 | 5 | 2 | 0.02895 | 3.73 |
| | 10 | — | 0.0304 | 2.04 |
| | 15 | — | 0.04655 | 3.92 |
| | 30 | — | 0.104 | 10.62 |
| | 60 | — | 0.17755 | 19.21 |
| | 90 | — | 0.248 | 27.43 |
| | 120 | — | 0.3065 | 34.25 |
| | 1440 | 4 | 0.3944 | 178.04 |
| 3 | 5 | — | 0.0107 | −0.26 |
| | 10 | — | 0.02555 | 1.47 |
| | 15 | — | 0.03975 | 3.13 |
| | 30 | — | 0.08735 | 8.68 |
| | 60 | — | 0.1766 | 19.10 |
| | 90 | — | 0.25815 | 28.61 |
| | 120 | — | 0.32055 | 35.89 |
| | 1440 | 4 | 0.4202 | 190.08 |

(c): certain samples were diluted before analyzed to avoid the possibility of falling outside the linearity range of the instrument.
(d): absorbance data less than 0.05 is below instrument detection limit and therefore concentration calculated from such absorbance is an approximate value.

TABLE 14

Rifaximin Concentrations of 25:75 (w/w) Rifaximin/HPMC-P Dispersion in pH 6.52 FASSIF Buffer at 37° C.

| Dissolution Vessel No | Time (min.) | Dilution (c) | Absorbance (d) | Concentration (µg/mL) |
|---|---|---|---|---|
| 4 | 5 | — | 0.01555 | 0.30 |
| | 10 | — | 0.03395 | 2.45 |
| | 15 | — | 0.0528 | 4.65 |
| | 30 | — | 0.12235 | 12.77 |
| | 60 | — | 0.2643 | 29.33 |
| | 90 | — | 0.37355 | 42.08 |
| | 120 | — | 0.455 | 51.58 |
| | 1440 | 4 | 0.39465 | 178.16 |
| 5 | 5 | — | 0.0329 | 2.33 |
| | 10 | — | 0.06805 | 6.43 |
| | 15 | — | 0.07905 | 7.71 |
| | 30 | — | 0.13745 | 14.53 |
| | 60 | — | 0.242 | 26.73 |
| | 90 | — | 0.32595 | 36.52 |
| | 120 | — | 0.40555 | 45.81 |
| | 1440 | 4 | 0.38525 | 173.77 |
| 6 | 5 | — | 0.0155 | 0.30 |
| | 10 | — | 0.057 | 5.14 |
| | 15 | — | 0.09415 | 9.47 |
| | 30 | — | 0.17145 | 18.49 |
| | 60 | — | 0.2724 | 30.27 |
| | 90 | — | 0.36815 | 41.45 |
| | 120 | — | 0.43155 | 48.84 |
| | 1440 | 4 | 0.3838 | 173.09 |

(d): certain samples were diluted before analyzed to avoid the possibility of falling outside the linearity range of the instrument.
(e): absorbance data less than 0.05 is below instrument detection limit and therefore concentration calculated from such absorbance is an approximate value.

TABLE 15

Averaged Concentrations of 50:50 (w/w) Rifaximin/HPMC-AS MG Dispersions in pH 6.52 FASSIF Buffer at 37° C.

| Description (a) | Dissolution Vessel No | Time (min.) | Concentration (µg/mL) | Average Concentration (µg/mL) | Standard Deviation |
|---|---|---|---|---|---|
| (50:50) HPMC-AS MG | 1 | 5 | 0.34 | 1.27[b] | 2.154 |
| | 2 | | 3.73 | | |
| | 3 | | −0.26 | | |
| | 1 | 10 | 2.53 | 2.01[b] | 0.5284 |
| | 2 | | 2.04 | | |
| | 3 | | 1.47 | | |
| | 1 | 15 | 5.13 | 4.06[b] | 1.008 |
| | 2 | | 3.92 | | |
| | 3 | | 3.13 | | |
| | 1 | 30 | 9.75 | 9.69 | 0.970 |
| | 2 | | 10.62 | | |
| | 3 | | 8.68 | | |
| | 1 | 60 | 17.46 | 18.59 | 0.977 |
| | 2 | | 19.21 | | |
| | 3 | | 19.10 | | |
| | 1 | 90 | 24.35 | 26.80 | 2.202 |
| | 2 | | 27.43 | | |
| | 3 | | 28.61 | | |
| | 1 | 120 | 28.39 | 32.85 | 3.945 |
| | 2 | | 34.25 | | |
| | 3 | | 35.89 | | |
| | 1 | 1440 | 184.99 | 184.37 | 6.0455 |
| | 2 | | 178.04 | | |
| | 3 | | 190.08 | | |

(a): approximate ratio of Rifaximin to polymer, by weight.
(b): absorbance data less than 0.05 is below instrument detection limit and therefore concentration calculated from such absorbance is an approximate value.

TABLE 16

Averaged Concentrations of 25:75 (w/w) Rifaximin/HPMC-P Dispersions in pH 6.52 FASSIF Buffer at 37° C.

| Description (a) | Dissolution Vessel No | Time (min.) | Concentration (µg/mL) | Average Concentration (µg/mL) | Standard Deviation |
|---|---|---|---|---|---|
| (25:75) HPMC-P | 4 | 5 | 0.30 | 0.98 (b) | 1.171 |
| | 5 | | 2.33 | | |
| | 6 | | 0.30 | | |
| | 4 | 10 | 2.45 | 4.67 (b) | 2.030 |
| | 5 | | 6.43 | | |
| | 6 | | 5.14 | | |
| | 4 | 15 | 4.65 | 7.28 | 2.442 |
| | 5 | | 7.71 | | |
| | 6 | | 9.47 | | |

TABLE 16-continued

Averaged Concentrations of 25:75 (w/w) Rifaximin/HPMC-P
Dispersions in pH 6.52 FASSIF Buffer at 37° C.

| Description (a) | Dissolution Vessel No | Time (min.) | Concentration (µg/mL) | Average Concentration (µg/mL) | Standard Deviation |
|---|---|---|---|---|---|
|  | 4 | 30 | 12.77 | 15.26 | 2.935 |
|  | 5 |  | 14.53 |  |  |
|  | 6 |  | 18.49 |  |  |
|  | 4 | 60 | 29.33 | 28.78 | 1.840 |
|  | 5 |  | 26.73 |  |  |
|  | 6 |  | 30.27 |  |  |
|  | 4 | 90 | 42.08 | 40.02 | 3.041 |
|  | 5 |  | 36.52 |  |  |
|  | 6 |  | 41.45 |  |  |
|  | 4 | 120 | 51.58 | 48.75 | 2.886 |
|  | 5 |  | 45.81 |  |  |
|  | 6 |  | 48.84 |  |  |
|  | 4 | 1440 | 178.16 | 175.01 | 2.749 |
|  | 5 |  | 173.77 |  |  |
|  | 6 |  | 173.09 |  |  |

(a): approximate ratio of Rifaximin to polymer, by weight.
(b): absorbance data less than 0.05 is below instrument detection limit and therefore concentration calculated from such absorbance is an approximate value.

TABLE 17

Analysis of Rifaximin Dispersions after Dissolution
Test in pH 6.52 FASSIF Buffer at 37° C.

| Description (a) | Dissolution Vessel No | Analysis | Results |
|---|---|---|---|
| (50:50) HPMC-AS MG | 1 | PLM | no B/E observed change view field, no B/E |
|  | 2 | PLM | no B/E observed change view field, no B/E |
|  | 3 | PLM | no B/E observed majority no B/E, only 1 B/E particle in view field |
| (25:75) HPMC-P | 4 | PLM | B/E flakes and blades |
|  | 5 | PLM | no B/E material + B/E flakes |
|  | 6 | PLM | no B/E material + B/E flakes & blades |

(a): approximate ratio of Rifaximin to polymer, by weight.

Abbreviations

| Type | Abbreviation | Full Name / Description |
|---|---|---|
| INSTRUMENTAL | XRPD | x-ray powder diffractometry |
|  | mDSC | modulated differential scanning calorimetry |
|  | TG-IR | thermogravimetric infrared |
|  | PLM | polarized light microscopy |
|  | UV | ultraviolet spectroscopy |
| POLYMER | HPMC-AS | hydroxypropylmethyl cellulose acetate succinate |
|  | HPMC-P | hydroxypropylmethyl cellulose phthalate |
|  | Eudragit L100 | anionic polymers with methacrylic acid as a functional group, dissolution at pH > 6.0 |
|  | PVP K-90 | polyvinylpyrrolidone, grade K-90 |
| RESULTS | $T_g$ | glass transition temperature |
|  | $\Delta C_P$ | heat of capacity change |
|  | amorph. | amorphous |
|  | agg. | aggregates |
|  | irr. | irregular |
|  | decomp. | decomposition |
|  | B | birefringence |
|  | E | extinction |

Example 2

Ternary Dispersion of 50:50 (w/w) Rifaximin:HPMC-AS MG

A ternary dispersion of 50:50 (w/w) Rifaximin:HPMC-AS MG with 5.9 wt % Pluronic F-127 was prepared in large quantity (containing approximately 110 g of Rifaximin) by spray drying. Disclosed herein are the analytical characterizations for Rifaximin ternary dispersion as-prepared and post-stress samples at 70° C./75% RH for 1 week and 3 week, and post-stress sample at 40° C./75% RH for 6 weeks and 12 weeks.

Characterization of Rifaximin Ternary Dispersion

Characterizations of the spray dried Rifaximin ternary dispersion (50:50 (w/w) rifaximin:HPMC-AS MG with 5.9 wt % Pluronic F-127) are described in Table 18.

TABLE 18

Characterizations of Combined Rifaximin Ternary
Dispersion Solids - Spray Drying

| Sample ID | Analysis | Results (b) |
|---|---|---|
| 4103-74-01a | XRPD | x-ray amorphous |
|  | mDSC | 136° C. (midpoint, $T_g$) |
|  |  | 0.4 J/g·° C. ($\Delta$Cp) |
|  | TG-IR | 0.7 wt % |
|  |  | (loss up to 100° C.) |
|  |  | 202° C. |
|  |  | (onset, volatilization and apparent decomp.) |
|  |  | methanol and possible acetic acid |
|  | IR-ATR | consistent with structure |
|  | Raman | consistent with structure |
|  | SEM | agglomerates of collapsed spheres |
|  | PLM | irregularly-shaped equant particles |
|  | PSA | d10 (µm): 3.627, d50 (µm): 8.233, d90 (µm): 17.530 |
|  | DVS | 0.13 wt % (loss at 5% RH) |
|  |  | 11.14 wt % (gain, 5-95% RH) |
|  |  | 10.80 wt % (loss, 95-5% RH) |
| 4074-89-01 (c) | XRPD | x-ray amorphous |

(b): temperatures are round to the nearest degree; ΔCp is rounded to one decimal places and wt % is rounded to one decimal place.

Figure 46:
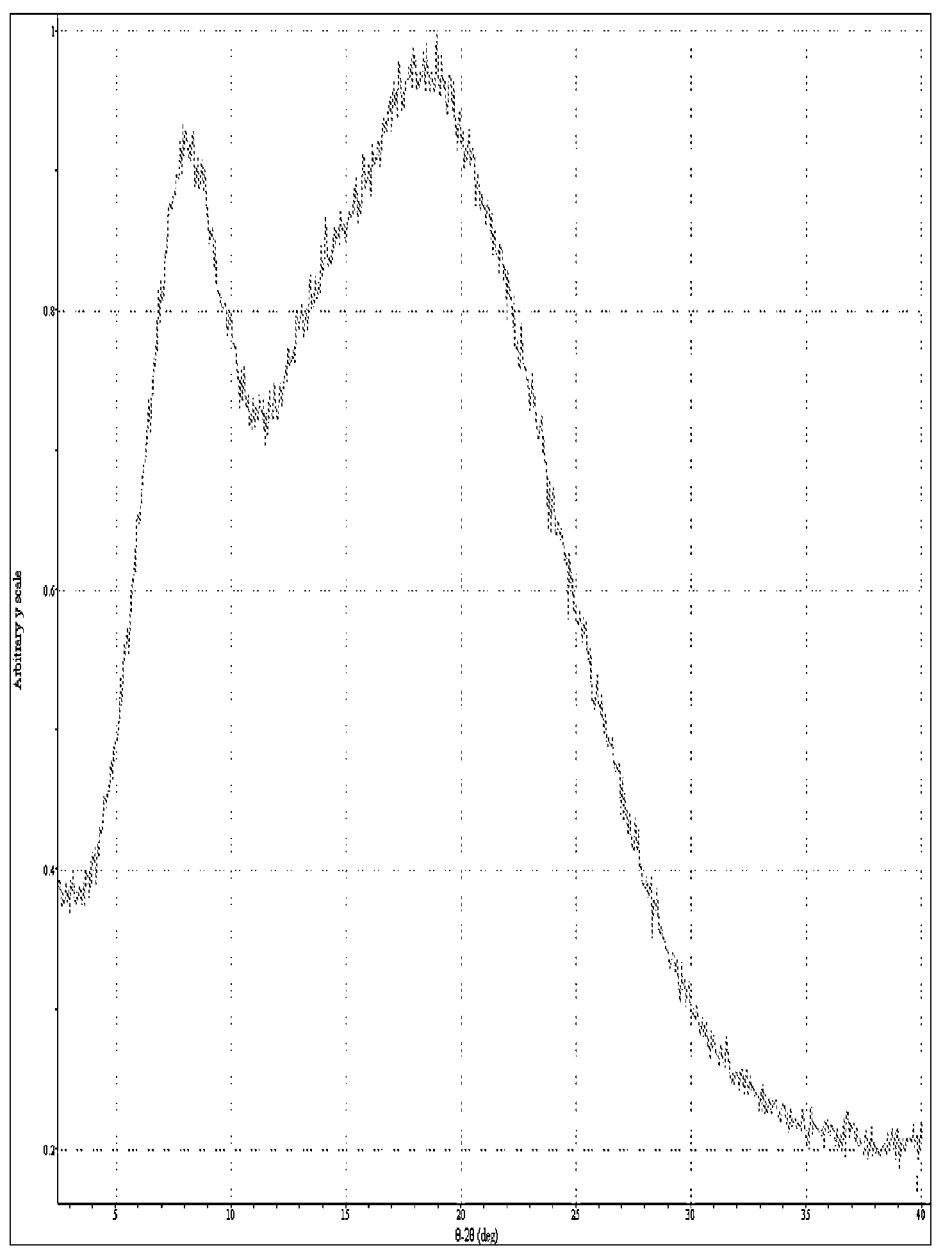
FIG. 46. An exemplary XRPD pattern for combined solids of Rifaximin/HPMC-AS MG/Pluronic ternary dispersion.
Figure 47:
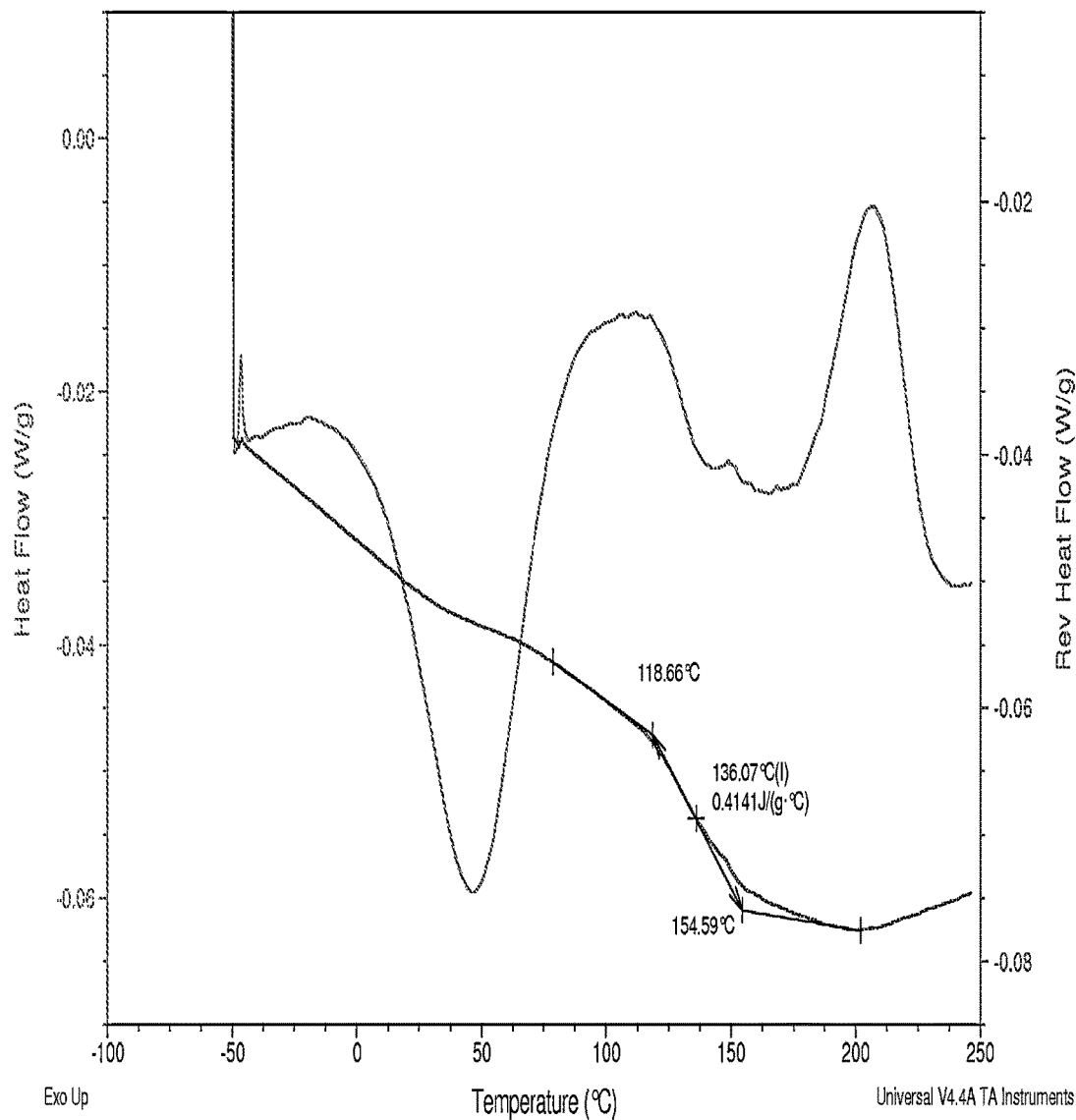
FIG. 47. A modulate DSC thermogram for combined solids of Rifaximin/HPMC-AS MG/Pluronic ternary dispersion.

A high resolution XRPD pattern was acquired and material is x-ray amorphous (FIG. 46). By mDSC (FIG. 47), a single apparent $T_g$ is observed from the step change in the reversing heat flow signal at approximately 136° C. with a heat capacity change at $T_g$ of approximately 0.4 J/g·° C.

Figure 48:
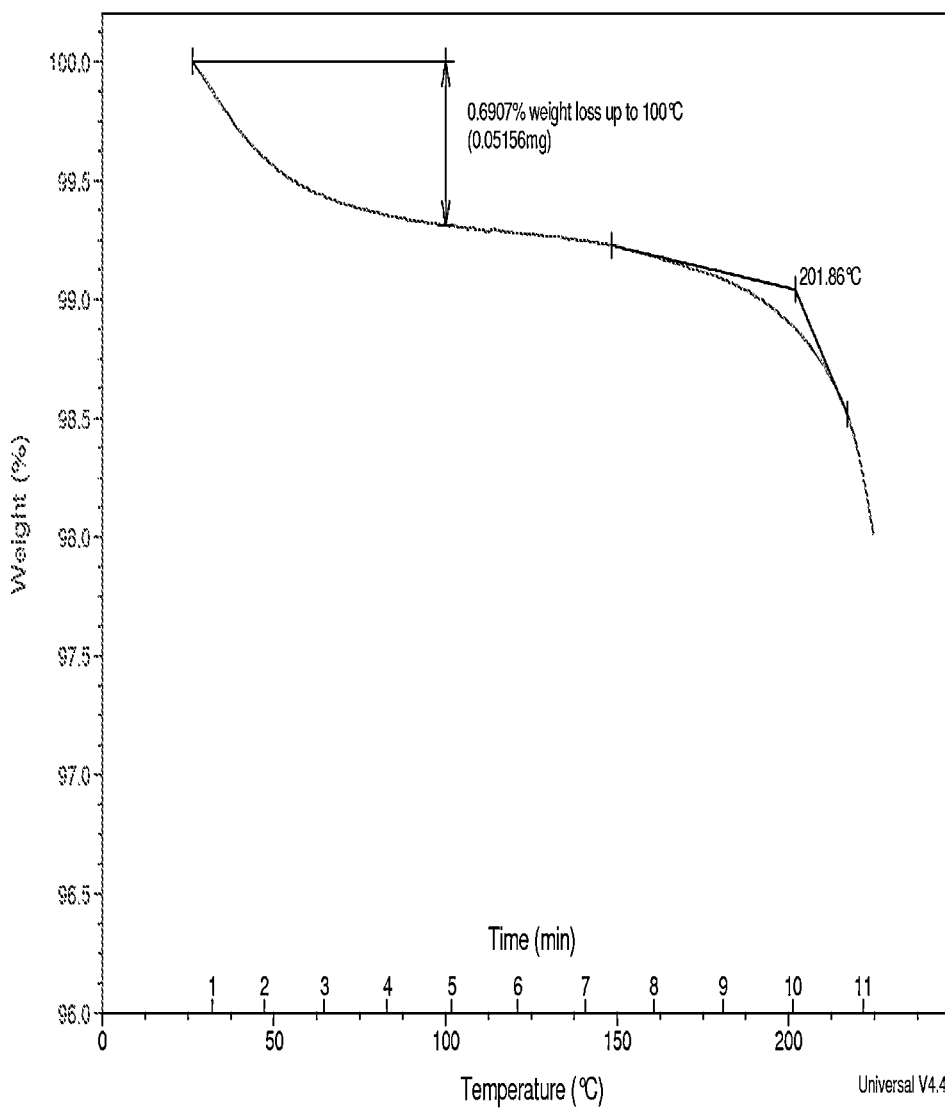
FIG. 48. A TG-IR analysis for combined solids of Rifaximin/HPMC-AS MG/Pluronic ternary dispersion-TGA thermogram.
Figure 49:
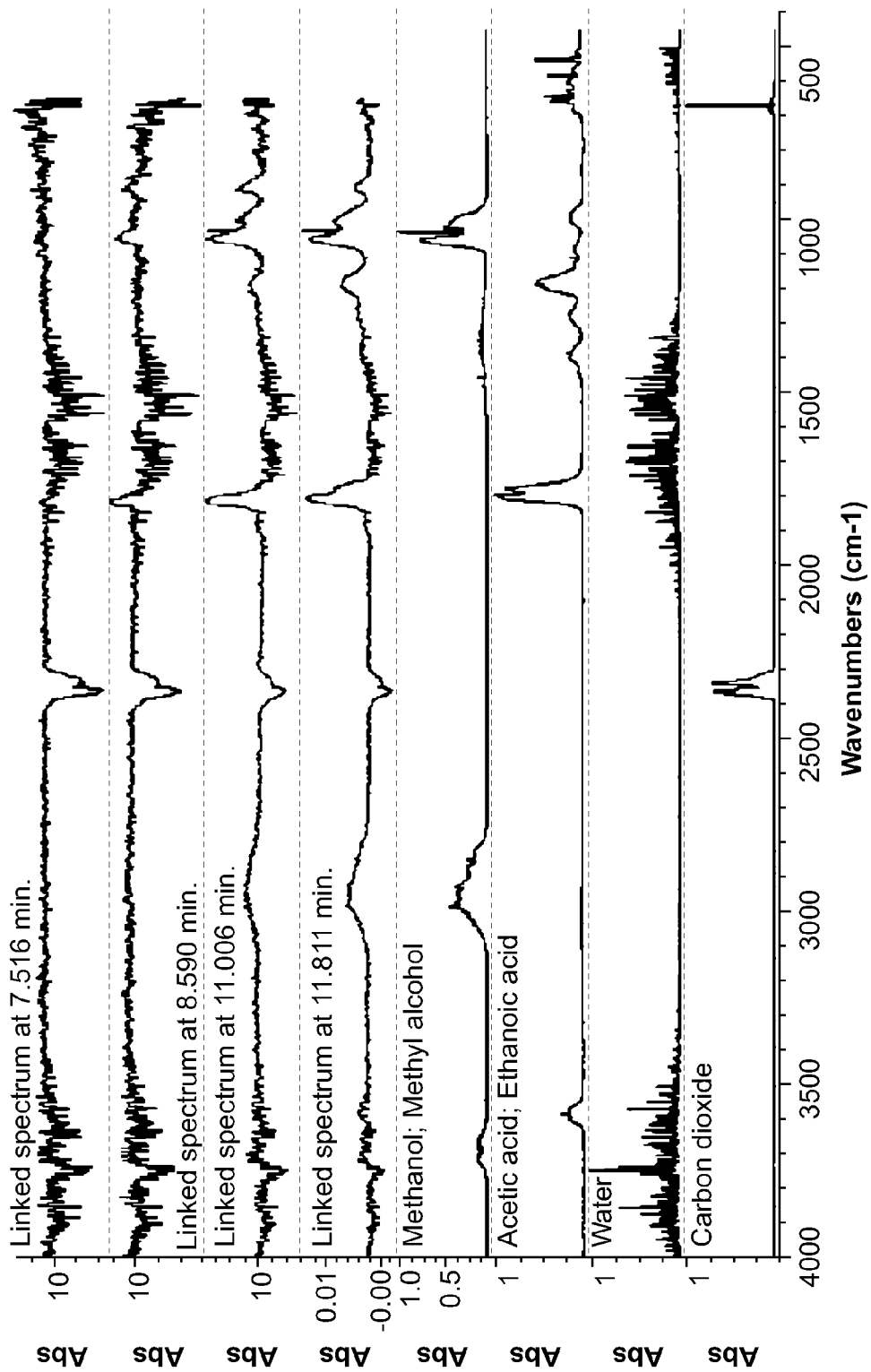
FIG. 49. An exemplary TG-IR analysis for combined solids of Rifaximin/HPMC-AS MG/Pluronic ternary dispersion.

Thermogravimetric analysis coupled with infra-red spectroscopy (TG-IR) was performed to analyze volatiles generated upon heating. The total weight loss of sample was approximately 0.7 wt % to 100° C. and the dramatic change in the slope occurs at approximately 202° C. (FIG. 48). The Gram-Schmidt plot corresponds to the overall IR intensity associated with volatiles released by a sample upon heating at 20° C./min. By Gram-Schmidt, a negligible increase of intensity upon heating is observed before ~7 minutes followed by a dramatic increase of intensity with the maximum at ~11.8 min. The waterfall plot (data not shown) of this sample indicates volatile are released upon heating after ~7 min (data is shown in FIG. 49 using the linked IR spectrum at different time points as an example) and volatiles were identified as residual methanol from the processing solvent in spray drying and possible acetic acid from HPMC-AS MG.

Figure 50:
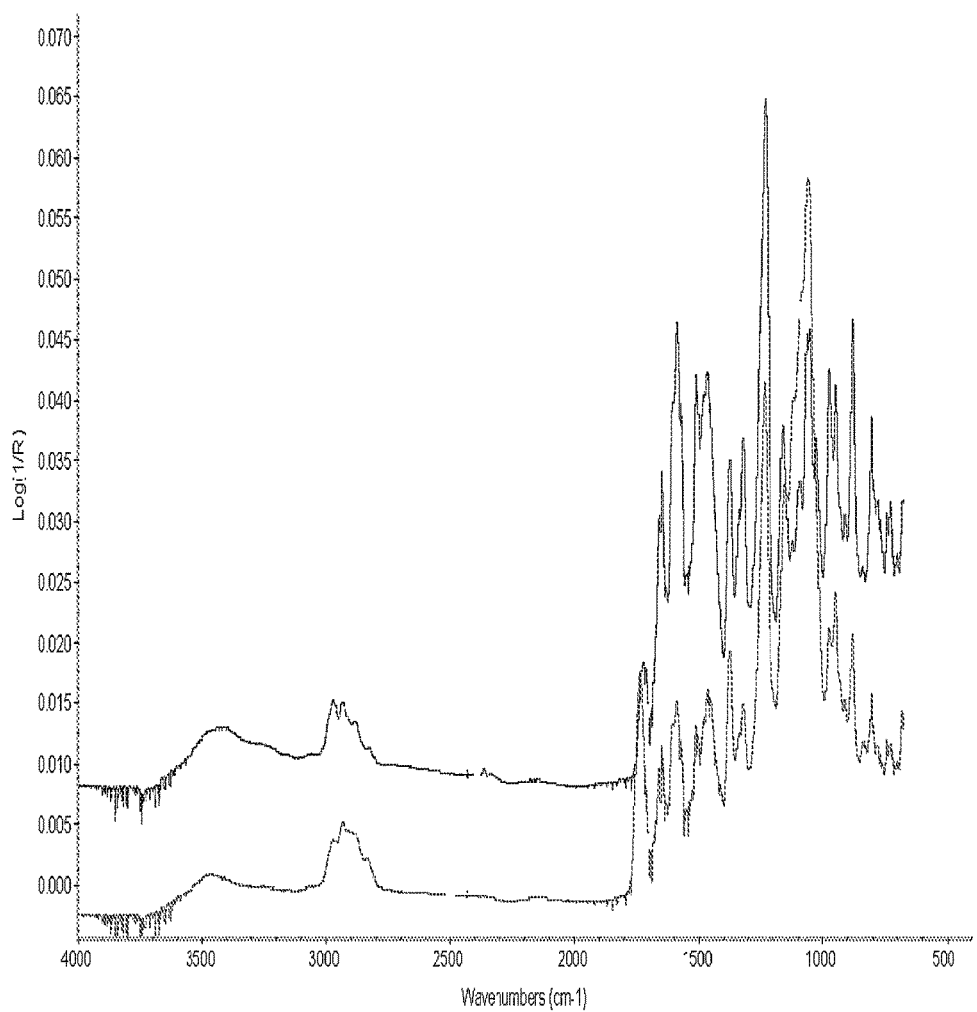
FIG. 50. An exemplary overlay of IR spectra for X-ray amorphous Rifaximin and combined solids of Rifaximin/HPMC-AS MG/Pluronic ternary dispersion.
Figure 51:
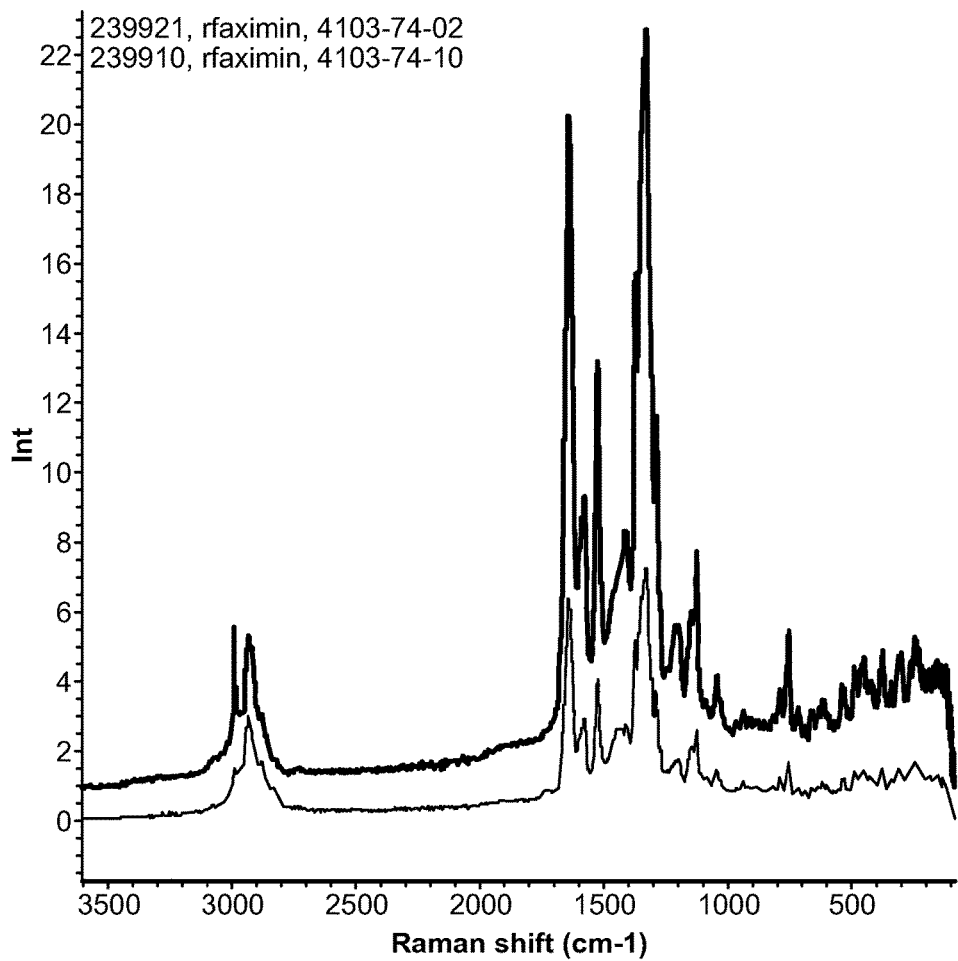
FIG. 51. An exemplary overlay of Raman spectra for X-ray amorphous Rifaximin and combined solids of Rifaximin/HPMC-AS MG/Pluronic ternary dispersion.

Vibrational spectroscopy techniques, including IR and Raman were employed to further characterize this ternary dispersion. The overlay of IR spectra for the dispersion and X-ray amorphous Rifaximin is shown in FIG. 50. Based on visual inspection, two spectra are very similar. Similar observations can be drawn from the comparison of Raman analysis (FIG. 51). The sample is composed of agglomerates of collapsed spheres. Particles sizes of spheres are not uniform, ranging from slightly larger to much less than 10 μm.

Figure 52:
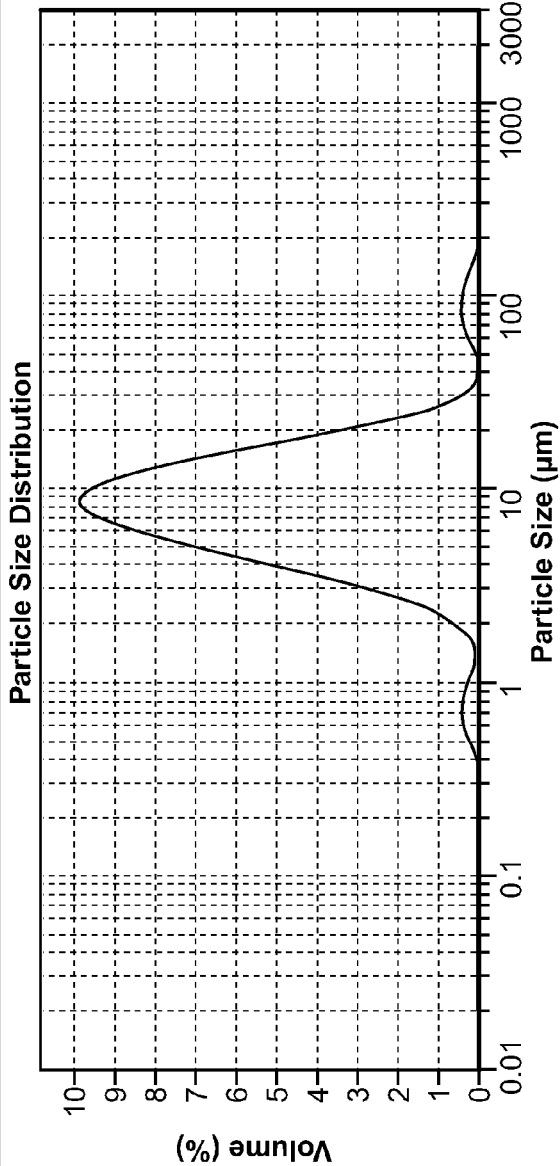
FIG. 52. A particle size analysis report for combined solids of Rifaximin/HPMC-AS MG/Pluronic ternary dispersion.

PLM images (data not shown) of solids dispersed in mineral oil were collected, which indicate sample primarily is composed of irregularly-shaped equant particles approximately 5-15 μm in length with some agglomerates 20-50 μm in length. Particle size analysis (FIG. 52) indicates that 50% of particles have size less than 8.233 μm and 90% of particles have size less than 17.530 μm. Data was acquired in 2% (w/v) Lecithin in Isopar G.

Figure 53:
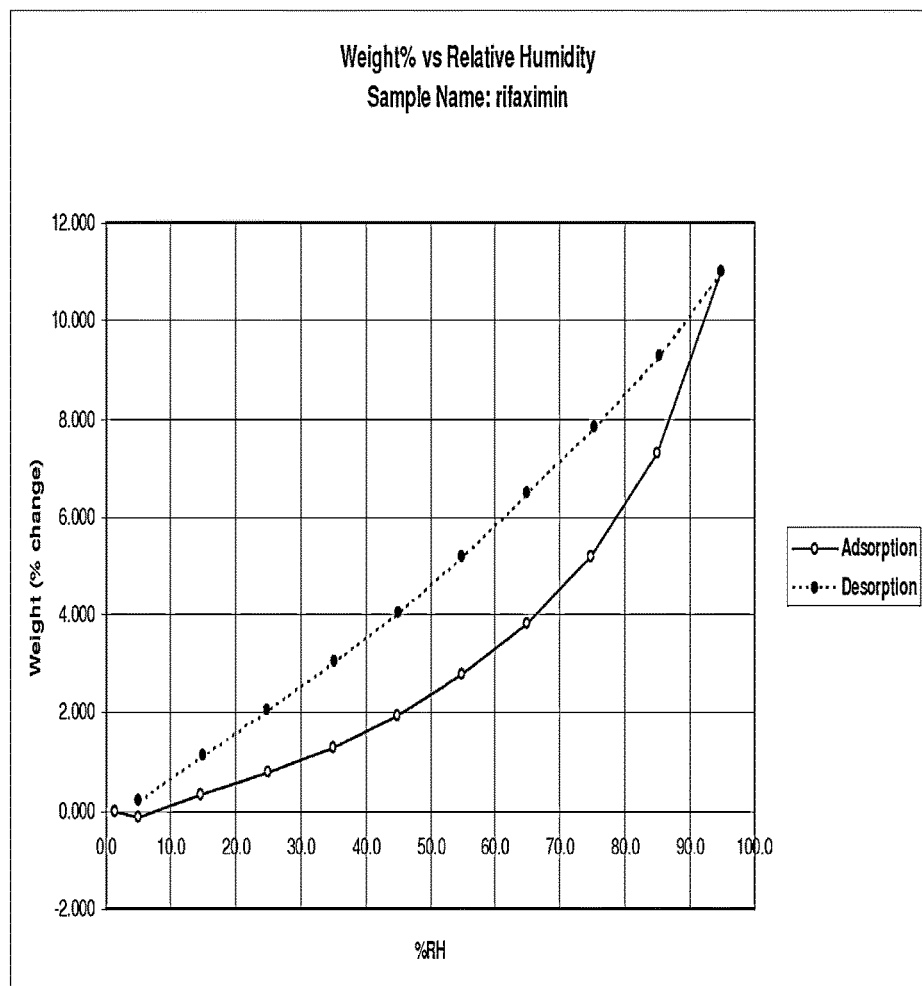
FIG. 53. An exemplary dynamic vapor sorption (DVS) analysis for combined solids of Rifaximin/HPMC-AS MG/Pluronic ternary dispersion.
Figure 54:
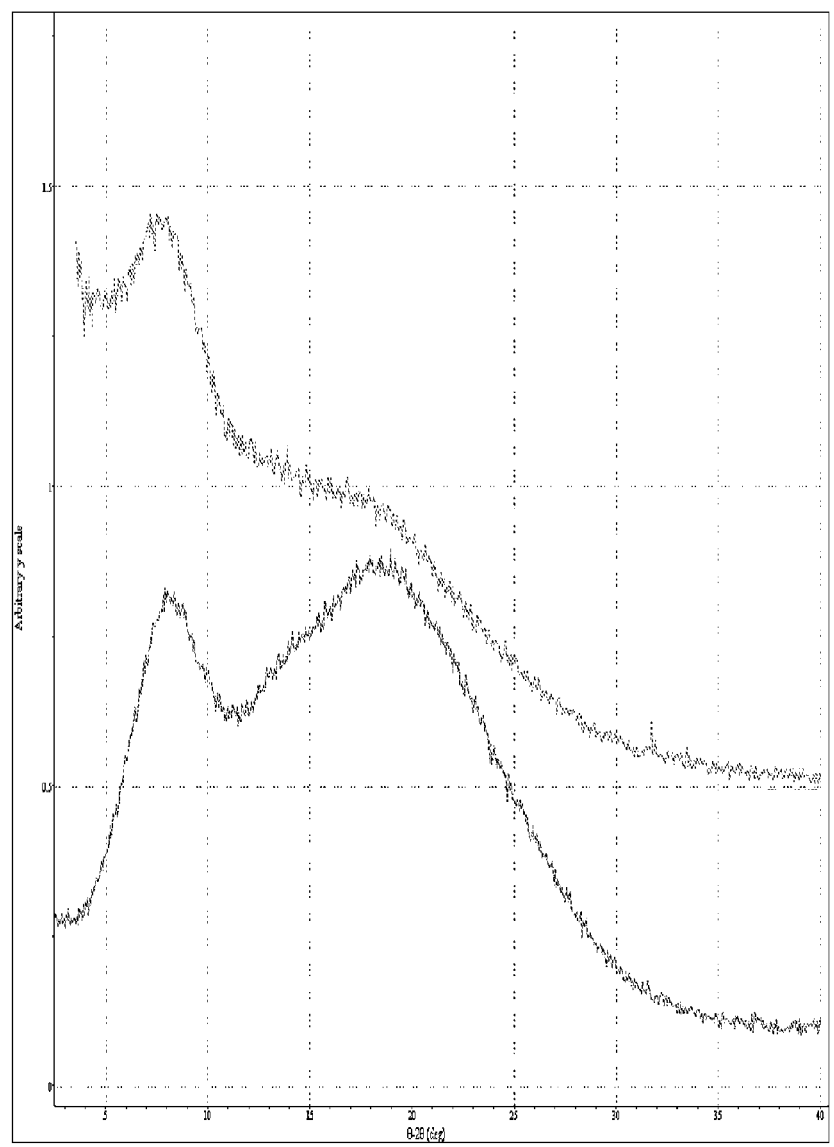
FIG. 54. An exemplary overlay of XRPD patterns for Rifaximin/HPMC-AS MG/Pluronic ternary dispersion post-DVS solids and solids as-prepared.

The DVS isotherm of solids is shown in FIG. 53. The material exhibits a 0.13 wt % loss upon equilibration at 5% RH. Solids then gain 11.14 wt % between 5% and 95% RH and exhibits some hysteresis with 10.80 wt % loss upon desorption from 95% to 5% RH. XRPD analysis of the solids recovered after completion of the desorption step showed no evidence of sharp peaks indicative of a crystalline solid (FIG. 54).

Physical Stability Assessment on Rifaximin Ternary Dispersion

An assessment of physical stability of this rifaximin ternary dispersion is currently in progress by exposing solids to varied elevated temperature/relative humidity conditions, including 25° C./60% RH, 40° C./75% RH and 70° C./75% RH for extended period of time. At designated time interval, such as at 1 week, 3 week, 6 week, and 12 weeks, selected samples were removed from stress conditions for characterization.

Table 19 summarized characterization results for the samples that stressed at 70° C./75% RH condition 1 week and 3 weeks, and the sample that stressed at 40° C./75% RH condition 6 weeks.

TABLE 19

Physical Stability Evaluation on Rifaximin Ternary Dispersion

| Condition | Time | Habit/Description | Analysis | Results (a) |
|---|---|---|---|---|
| 70° C./75% RH | 1 week | orange solids, aggregates, no B/E | XRPD | x-ray amorphous |
| | | | mDSC | 134° C. (midpoint, $T_g$) 0.4 J/g•° C. ($\Delta Cp$) |
| | | | SEM | agglomerates of collapsed spheres |
| | | | KF | 3.80% |
| 70° C./75% RH | 3 weeks | dark orange solids, aggregates, no B/E | XRPD | x-ray amorphous |
| | | | mDSC | 134° C. (midpoint, $T_g$) 0.4 J/g•° C. ($\Delta Cp$) |
| | | | SEM | agglomerates of collapsed spheres |
| | | | KF | 3.19% |
| 40° C./75% RH | 6 weeks | orange solids, aggregates, no B/E | XRPD | x-ray amorphous |
| | | | mDSC | 133° C. (midpoint, $T_g$) 0.4 J/g•° C. ($\Delta Cp$) |
| | | | SEM | agglomerates of collapsed spheres |
| | | | KF | 4.05% |
| 40° C./75% RH | 12 weeks | orange solids, aggregates, no B/E | XRPD | x-ray amorphous |
| | | | mDSC | 132° C. (midpoint, $T_g$) 0.5 J/g•° C. ($\Delta Cp$) |
| | | | SEM | agglomerates of collapsed spheres |
| | | | KF | 3.37% |

(a): temperatures are round to the nearest degree; ΔCp is rounded to one decimal places.

Figure 56:
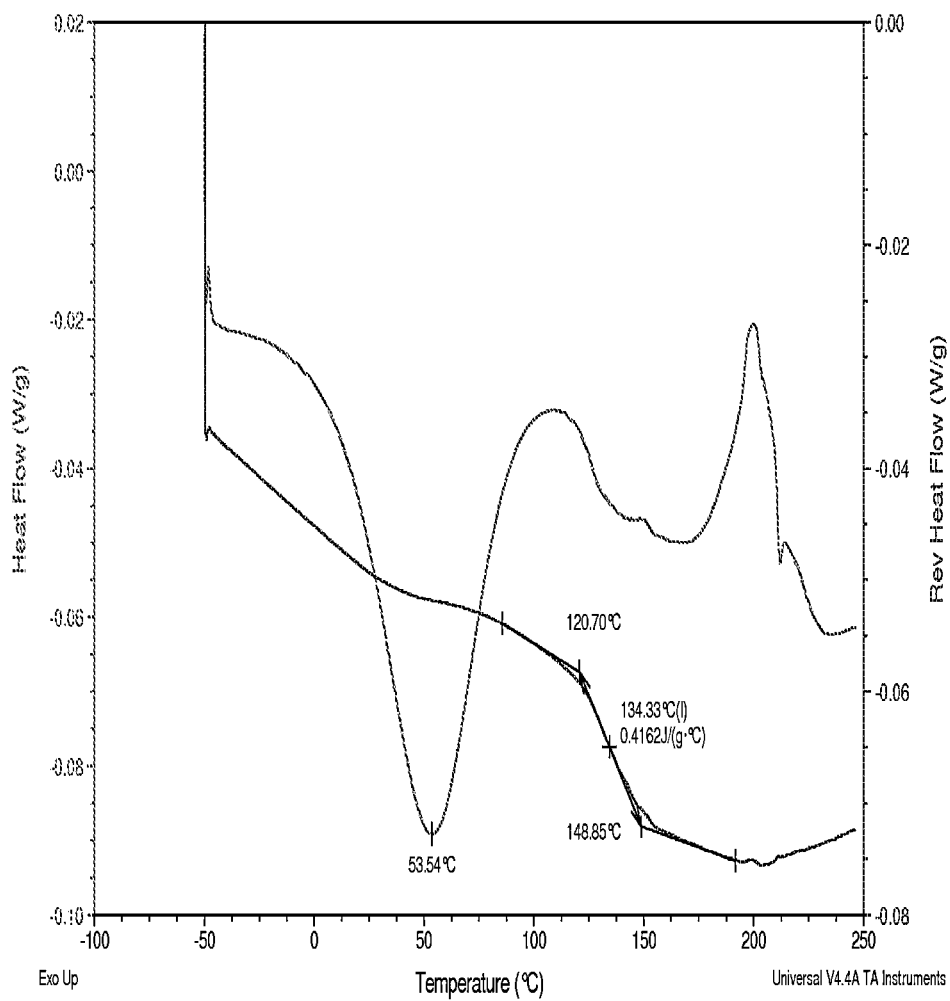
FIG. 56. An exemplary mDSC thermgram for Rifaximin ternary dispersion after 70° C./75% RH 1 week.

For a sample that was stressed at 70° C./75% RH for 1 week, solids are still x-ray amorphous according to XRPD (FIG. 55). A single $T_g$ at approximately 134° C. was observed from the apparent step change in the reversing heat flow signal in mDSC with the change of heat capacity 0.4 J/g ° C., indicating the components of each dispersion remained intimately miscible after stress (FIG. 56). A non-reversible endotherm was observed at approximately 54° C. which is likely due to the residual solvent from spray drying and moisture that materials absorbed during stress, which is confirmed by KF analysis that sample contains 3.80 wt % of water (KF analysis for Rifaximin ternary dispersion after 70° C./75% RH 1 week; 1.2855 g–R1=3.72 and 0.988 g–R1=3.87%). The sample is composed of agglomerates of collapsed spheres and particles sizes of spheres are not uniform, which is similar to the as-prepared material.

Figure 57:
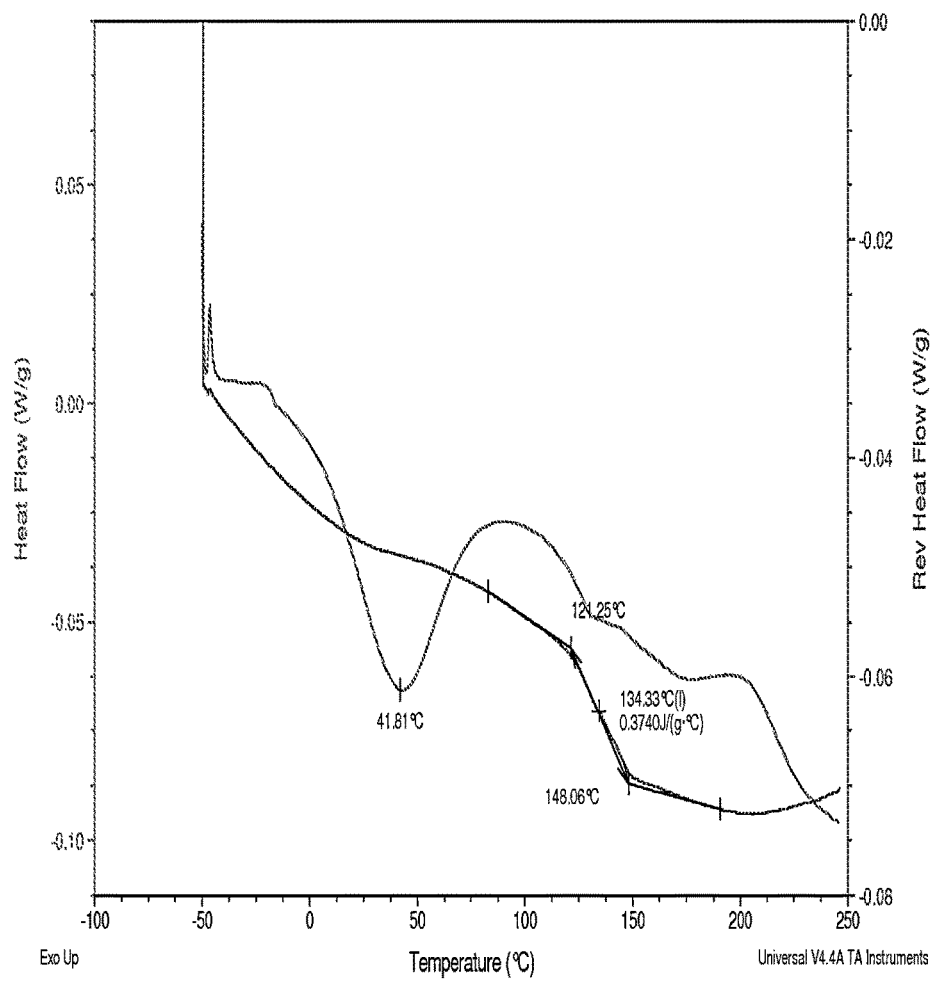
FIG. 57. An exemplary mDSC thermgram for Rifaximin ternary dispersion after 70° C./75% RH 3 weeks.

For the sample that was stressed at 70° C./75% RH for 3 weeks, although the color of the material appeared to be darker than the 1-week sample, characterization results for 3-week sample are similar to that for 1-week sample. Solids are also x-ray amorphous by XRPD (FIG. 55) and display a single $T_g$ at approximately 134° C. by mDSC (FIG. 57). KF analysis indicates it contains 3.19 wt % of water (KF analysis for rifaximin ternary dispersion after 70° C./75% RH 3 weeks; 1.2254 g–R1=3.45 and 1.1313 g–R1=2.93). By SEM (data not shown), the material has morphology similar to the as-prepared dispersion and 1-week stress sample, which is composed of agglomerates of collapsed spheres and particles sizes of spheres are not uniform.

Figure 58:
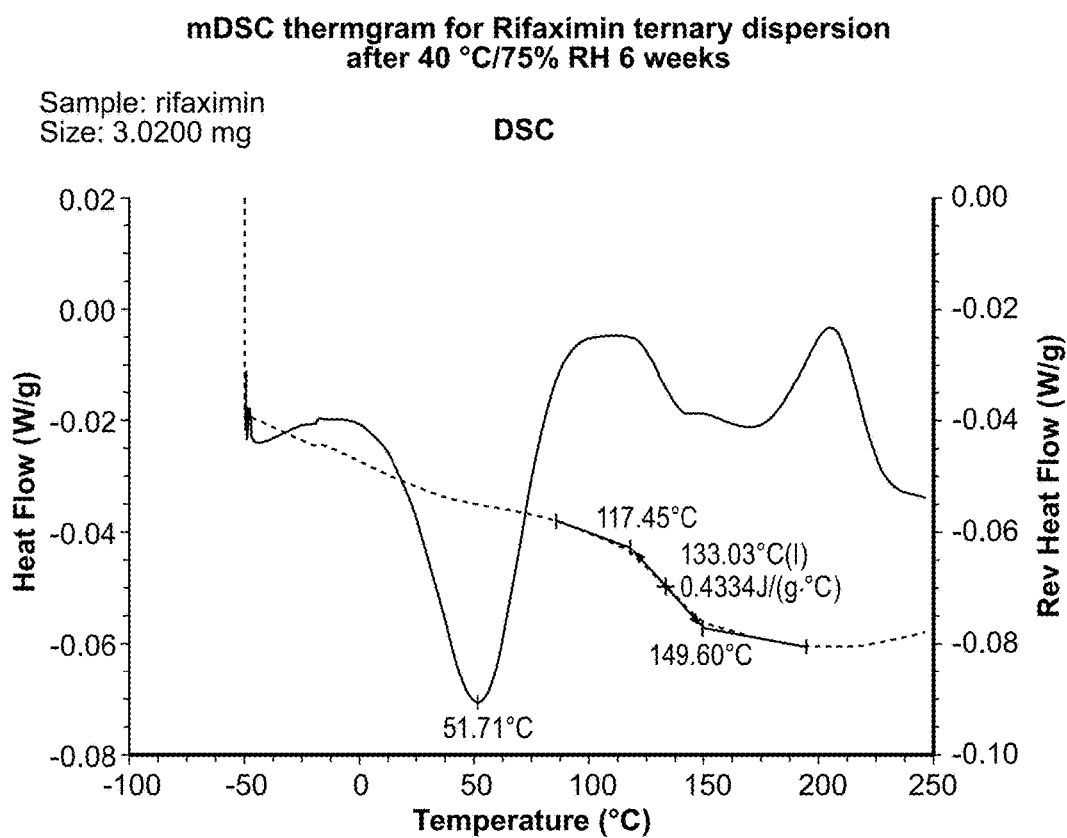
FIG. 58. An exemplary mDSC thermgram for Rifaximin ternary dispersion after 40° C./75% RH 6 weeks.

For the sample that was stressed at 40° C./75% RH for 6 weeks, solids are still x-ray amorphous according to XRPD (FIG. 55). It has a single $T_g$ at approximately 133° C. by mDSC with the change of heat capacity 0.4 J/g ° C. (FIG. 58). It contains 4.05 wt % of water by KF (KF analysis for rifaximin ternary dispersion after 40° C./75% RH 6 weeks; 1.0947 g–R1=3.47 and 1.2030–R1=4.63). By SEM (data not shown), the sample is composed of agglomerates of collapsed spheres and particles sizes of spheres are not uniform, which is similar to the as-prepared material.

Figure 59:
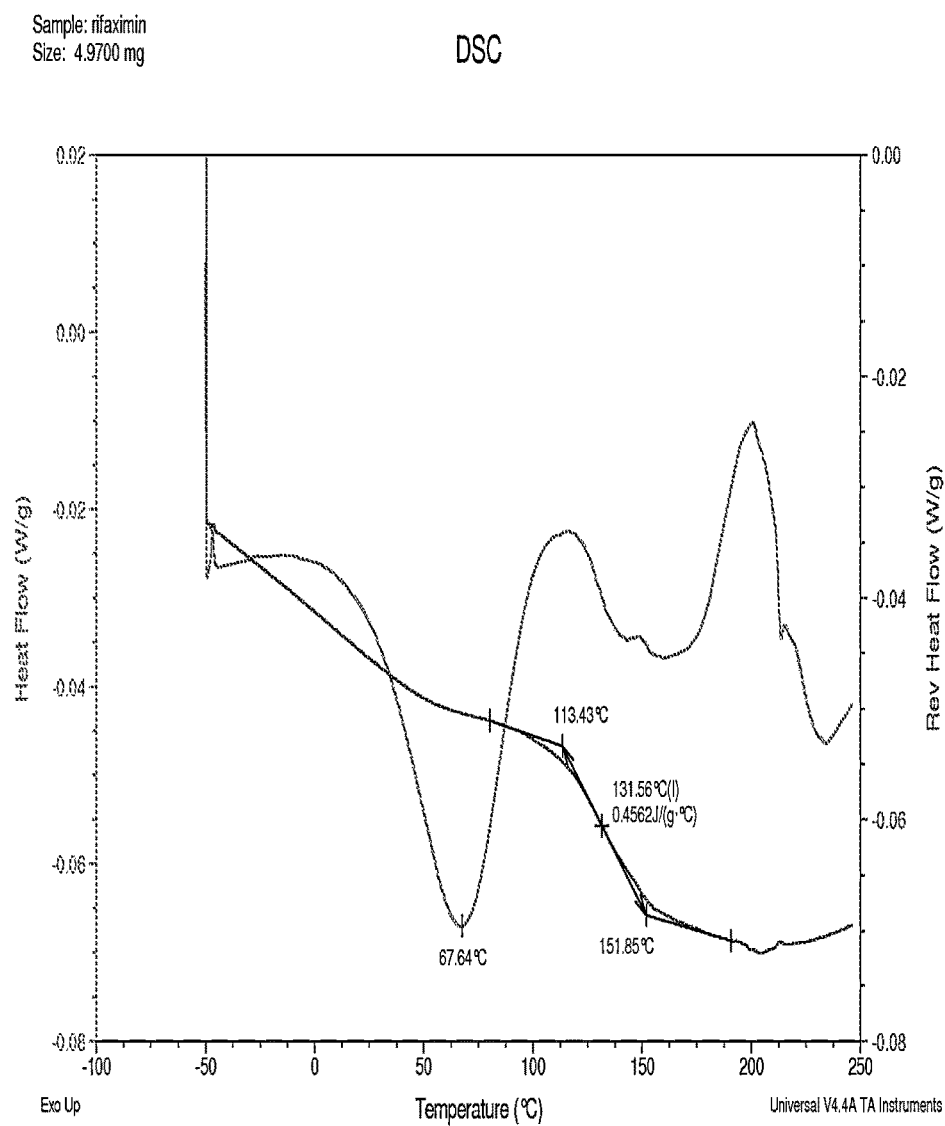
FIG. 59. An exemplary mDSC thermgram for Rifaximin ternary dispersion after 40° C./75% RH 12 weeks.

For the sample that was stressed at 40° C./75% RH for 12 weeks, solids are x-ray amorphous (FIG. 55) and display a single $T_g$ at approximately 132° C. with the change of heat capacity 0.5 J/g ° C. (FIG. 59). It contains 3.37 wt % of water by KF (KF analysis for Rifaximin ternary dispersion after 40° C./75% RH 12 weeks; 1.3687 g–R1=3.06 and 1.1630 g–R1=3.67). SEM analysis (data not shown) indicates that the sample is composed of agglomerates of collapsed spheres and particles sizes of spheres are not uniform, which is similar to the as-prepared material.

Example 3

Rifaximin Solid Dispersion Composition and Procedures

Rifaximin Ternary Dispersion Ingredients:

Rifaximin ternary dispersions (50:50 w/w Rifaximin: HPMC-AS MG with 5.9 wt % Pluronic F-127) were prepared from methanol using spray drying in closed mode suitable for processing organic solvents. Ingredients are listed as below in Table 20:

TABLE 20

Components of Rifaximin Solid Dispersion

| Component | mg/g | Purpose |
| --- | --- | --- |
| Rifaximin | 472 | active pharmaceutical ingredient |
| Hydroxypropylmethyl cellulose acetate succinate (HPMC-AS), Type MG | 472 | stabilizing agent |
| Pluronic F-127 | 56 | wetting agent |
| Methanol | — | volatile; removed during process |

Spray Drying Procedures:

Rifaximin ternary dispersions were prepared by spray drying in both small scale (~1 g API) and large scale (≥34 g API in a single batch).

For the small-scale sample, rifaximin and then the methanol were added to a flask. The mixture was stirred at ambient temperature for ~5 min to give a clear solution. HPMC-AS MG and Pluronic F-127 were added in succession and the sample was stirred for ~1 hr. An orange solution was obtained.

For large-scale samples, a solution was prepared at ~40° C. Rifaximin and then methanol were added to a flask and the mixture was stirred at ~40° C. for ~5 min until clear. HPMC-AS MG, and then Pluronic F-127 were added into the rifaximin solution under stirring at ~40° C. The sample continued to stir for ~1.5 hr to 2 hr at this temperature. A dark red solution was obtained. The sample was removed from the hot plate and left at ambient to cool.

Experimental conditions to prepare Rifaximin ternary solutions are summarized in Table 21 below:

TABLE 21

Experimental Conditions to Prepare Rifaximin Ternary Solutions

| Solvent | | weight (API/HPMC AS MG/Pluronic F127, g) | Temperature | Concentration (g/L) |
| --- | --- | --- | --- | --- |
| methanol, | 100 mL | 1.0535/1.0529/0.1249 | ambient | 22.3 |
| methanol, | 1000 mL | 34.07/34.07/4.02 | ~40° C. | 72.2 |
| methanol, | 1250 mL | 50.34/50.32/5.94 | ~40° C. | 85.3 |
| methanol, | 1250 mL | 50.16/50.14/5.92 | ~40° C. | 85 |
| methanol, | 1250 mL | 50.05/50.06/5.91 | ~40° C. | 85 |

During the spray drying process, both the small and large scale rifaximin ternary solutions were kept at ambient temperature. The pump % was decreased during the process in an attempt to control outlet temperature above 40° C. The operating parameters used for processing are presented in Table 22 below.

TABLE 22

Operating Parameters Used For Processing Rifaximin SD

| Description (a) | Inlet temp. (set, ° C.) | Aspirator % | Pump % | Inlet temp. (measured, ° C.) | Outlet temp. (measured, ° C.) | Spray rate (b) mL/min |
| --- | --- | --- | --- | --- | --- | --- |
| 50:50 | 120 | 95 | 35 | 120 | 60-55 | 10.4 |
| Rifaximin: | 120 | 95 | 65-30 | 120-119 | 61-42 | 23 |
| HPMC-AS MG | 120 | 95 | 50-30 | 120-119 | 67-43 | 16 |
| 5.9 wt % | 120 | 95 | 50-30 | 120-119 | 65-43 | 16 |
| Pluronic F-127 | 120 | 95 | 50-30 | 120-119 | 67-43 | 16 |

(a): 50:50 is approximate ratio of Rifaximin to polymer, by weight; 5.9 wt % Pluronic is weight fraction to 50:50 rifaximin:HPMC-AS MG dispersion.
(b): Flow rates are estimated. Flow rate for 4103-41-01 was measured at pump 35%; for 4103-56-01 was measured at pump 65%, while for others were measured at pump 50%.

Solids recovered after spray drying were dried at 40° C. under vacuum for 24 hours and then stored at sub-ambient temperatures over desiccant.

Spray Drying Process Parameters:
  Spray Dryer—PSD 1
  Two Fluid Niro Nozzle
  Nozzle orifice—1 mm
  Inlet gas temperature—125±5 deg C.
  Process gas flow (mmH2O)—44
  Atomizing gas pressure—0.7-1 bar
  Feed rate—4.7 kg/Hr
  Outlet temperature—55±3 deg C.
  Solution temperature—36 deg C.
  Post spray drying vacuum dry at 40 deg C. for 48 hrs

Example 4

Exemplary formulations for micronized, API, amorphous, solid dispersion and micronized capsules are below in Table 23. These capsules were used in the dog study of Example 5.

TABLE 23

Capsule Formulation composition (Solid Dispersion (SD) Capsules)

| Ingredients | Micronized Capsules % | Micronized Capsules g/dose | API Capsules % | API Capsules g/dose | Amorphous Capsules % | Amorphous Capsules g/dose | SD Capsules % | SD Capsules g/dose | Micronized Tablets % | Micronized Tablets g/dose |
|---|---|---|---|---|---|---|---|---|---|---|
| Rifaximin | 95.5 | 2.2 | 47.2 | 2.2 | 51.7 | 2.2 | 42.47 | 2.2 | 50 | 2.2 |
| Ac-di-sol | 4.5 | 0.1 | 5 | 0.23 | 5 | 0.21 | 10.02 | 0.52 | 7.5 | 0.33 |
| Mannitol 160C | | | 47.8 | 2.23 | 43.3 | 1.84 | | | | |
| Pluronic 188 | | | | | | | 5.04 | 0.26 | | |
| HPMC AS | | | | | | | 42.47 | 2.2 | | |
| Avicel 113 | | | | | | | | | 26 | 1.14 |
| Avicel 112 | | | | | | | | | 15 | 0.66 |
| Magnesium Stearate | | | | | | | | | 1 | 0.04 |
| Cab-o-sil | | | | | | | | | 0.5 | 0.02 |
| Avicel CL-611 | | | | | | | | | | |
| Mannitol 160C | | | | | | | | | | |
| Total | 100 | 2.3 | 100 | 4.66 | 100 | 4.26 | 100 | 5.18 | 100 | 4.4 |

TABLE 24

Manufacture of rifaximin/HPMC-AS /Pluronic 275 mg Capsules

| Component | % Formula | mg/caps | Theo. Qty (g) | Actual Qty (g) |
|---|---|---|---|---|
| Rifaximin | 42.47 | 275 | 113.7 | 113.7 |
| HPMC-AS (type MG) | 42.47 | 275 | 113.7 | 113.7 |
| Pluronic F-127 | 5.04 | 32.63 | 13.49 | 13.49 |
| Sodium Croscarmellose | 10.02 | 64.87 | 26.82 | 26.82 |
| Hard Gelatin Capsule (size 000) Clear | 1 | N/A | 300 | 300 |
| Total | 100 | 647.5 | 267.7 g | |

Blending/Encapsulation Procedure:

To form the capsules sodium croscarmellose was added to the bag of SD rifaximin dispersion and bag blend for 1 minute, and then the material was added to the V-blender and blended for 10 minutes at 24 rpm.

The material was then discharged into a stainless steel pan and record the height of material in the pan. Empty capsules were tared using an analytical balance, then the capsules were filled by depressing into the bed of material. The weight is adjusted within + or −5% of target fill weight of 647.5 mg (acceptable fill range 615.13-679.88 mg).

Figure 61:
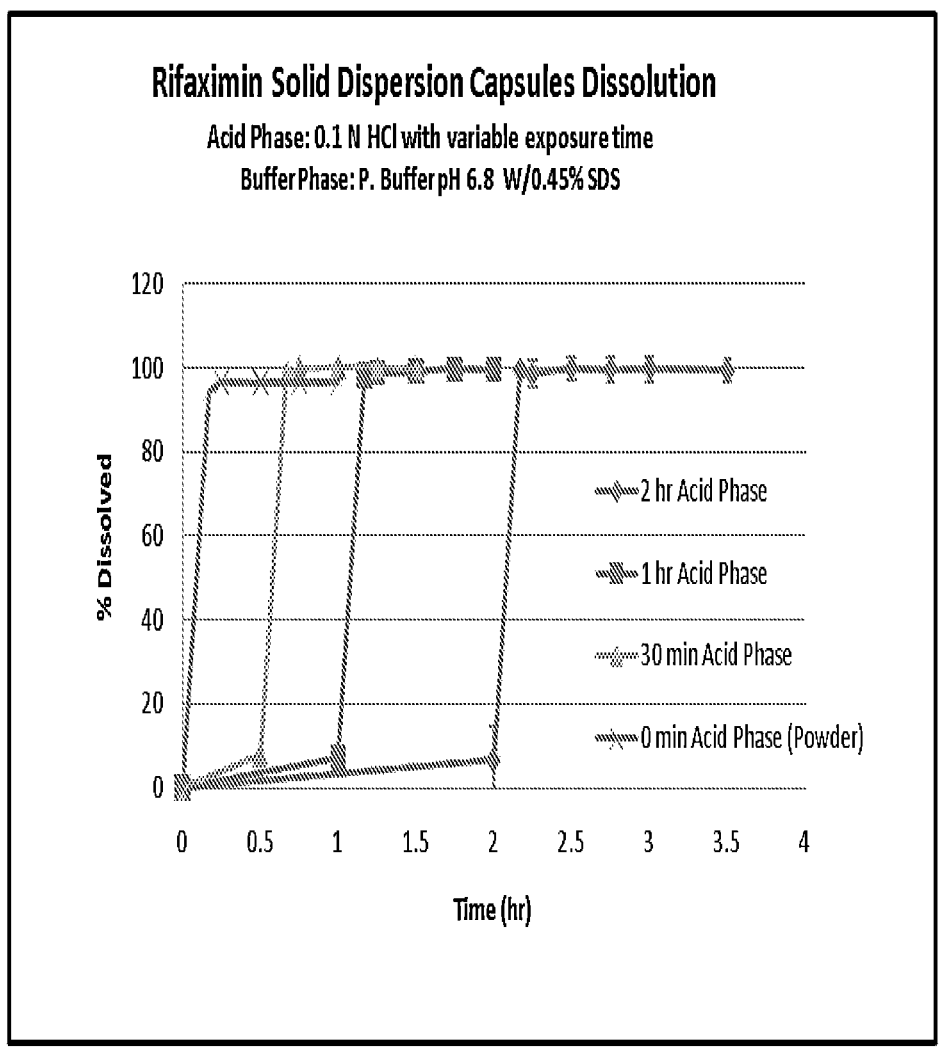
FIG. 61. Rifaximin SD capsules dissolution; acid phase: 0.1 N HCl with variable exposure time. Buffer phase: pH 6.8 with 0.45% SDS.
Figure 62:
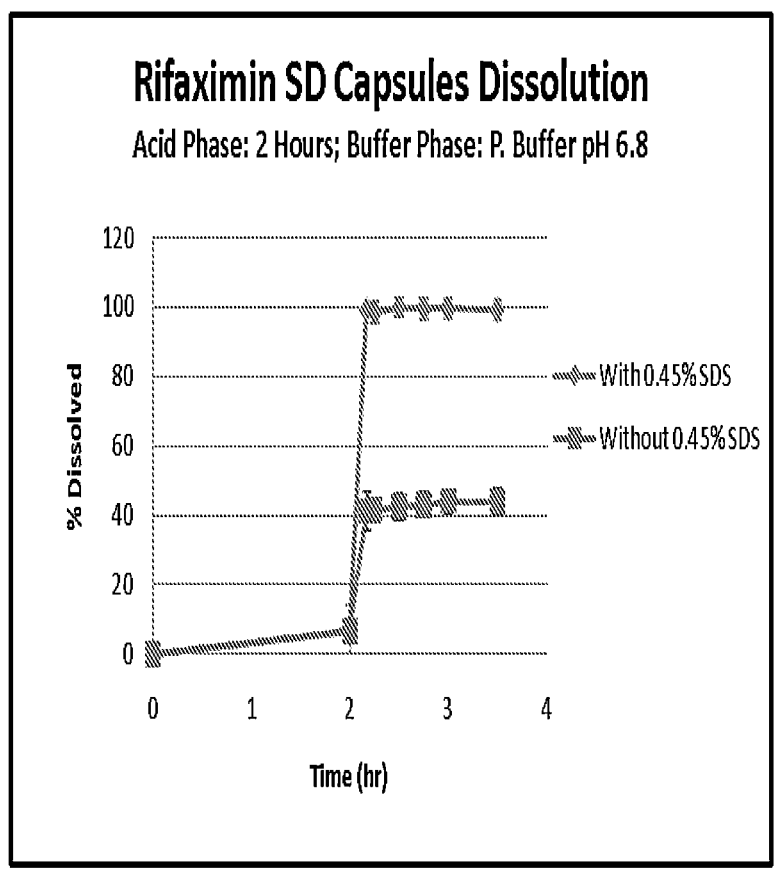
FIG. 62. Rifaximin SD capsules dissolution; acid phase: 2 hours; buffer phase: pH 6.8.
Figure 63:
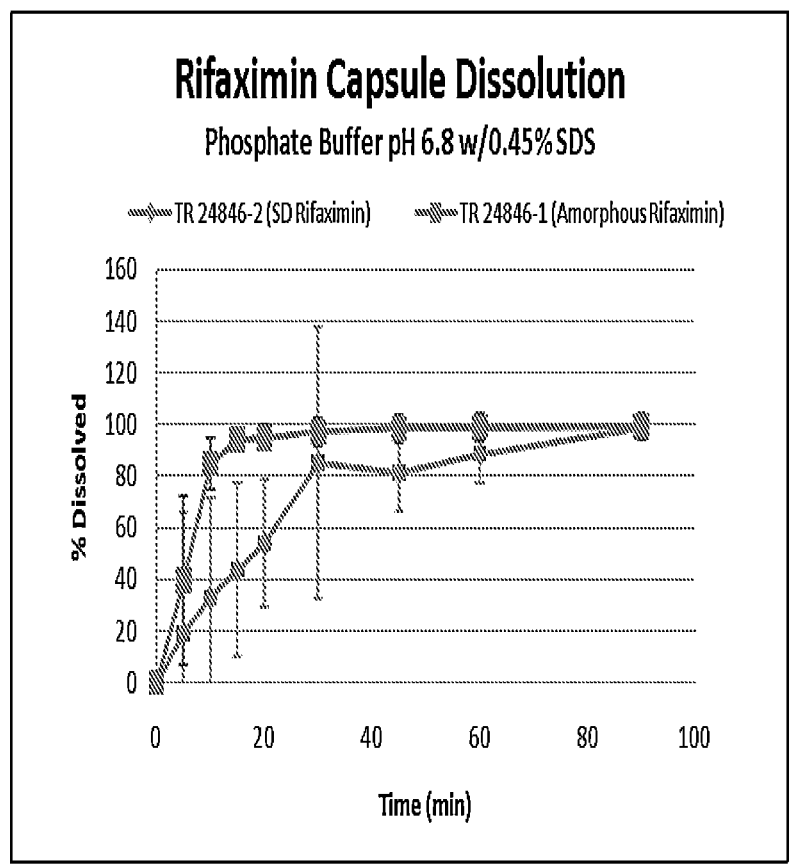
FIG. 63. Rifaximin capsule dissolution; phosphate buffer pH 6.8 with 0.45% SDS.
Figure 64A:
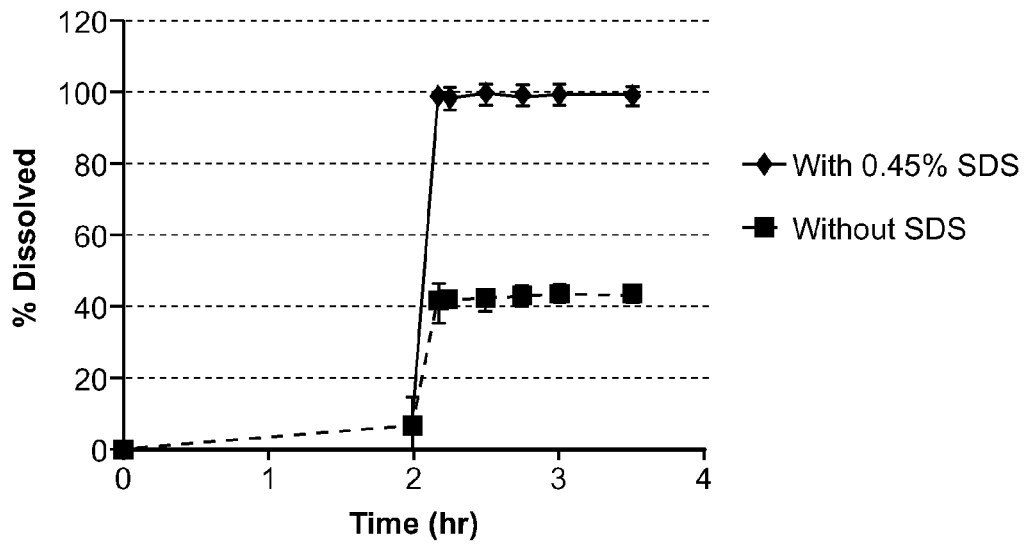
FIG. 64A acid phase 2 hours, buffer phase: P. Buffer, pH. 7.4.
Figure 64B:
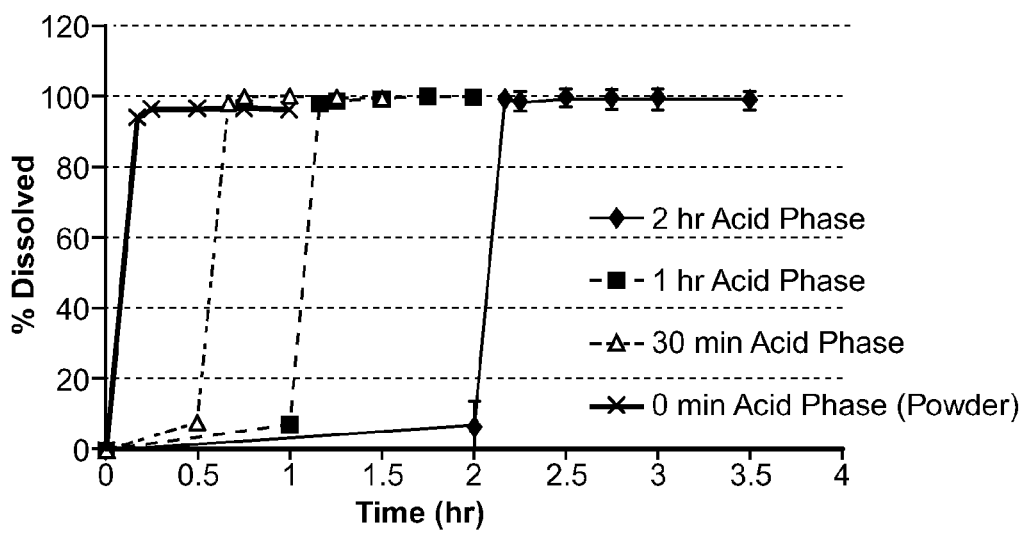
FIG. 64B acid phase: 0.1N HCl with various exposure times, buffer phase: P. buffer, pH 7.4 with 0.45% SDS.
Figure 64C:
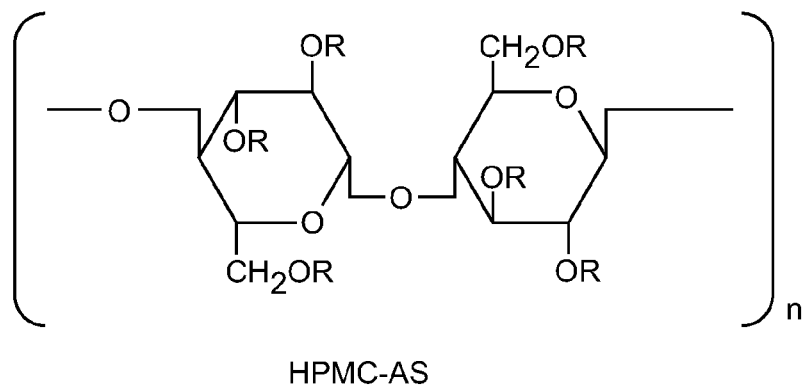
FIG. 64C shows the general structure of hydroxypropyl methylcellulose (HMPC).
Figure 64D:
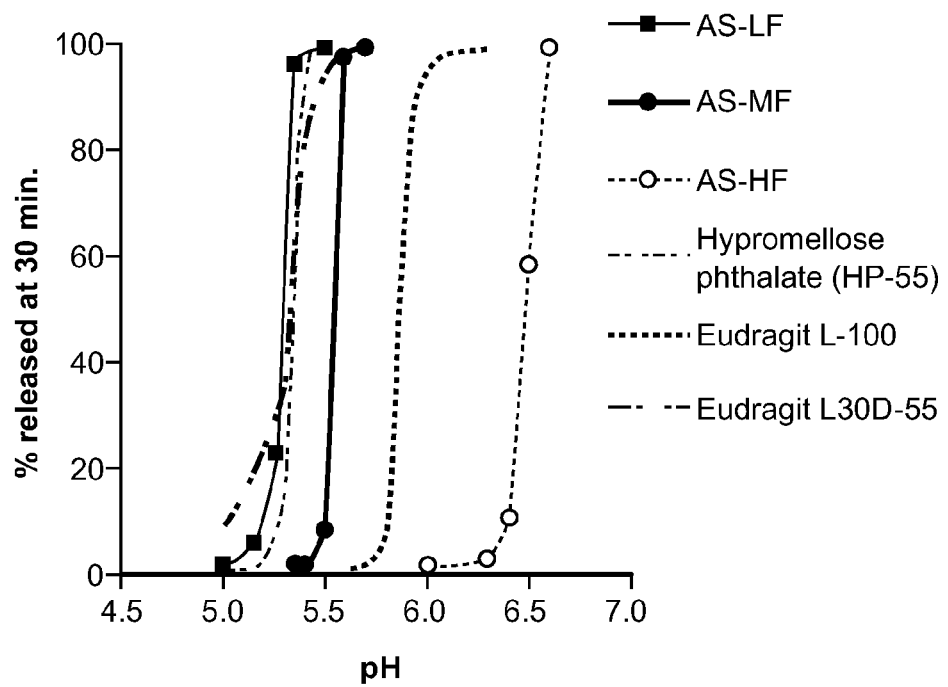
FIG. 64D represents the percent released at 30 min as a function of pH.

FIGS. 61-63 show the rifaximin solid dispersion (SD) capsules in various buffers; with and without SDS; and compared to amorphous rifaximin. FIG. 61 shows results of dissolution studies of rifaximin SD capsules in acid phase: 0.1 N HCl with variable exposure times in a buffer containing 0.45% SDS at pH 6.8. FIG. 62 shows results of dissolution studies of rifaximin SD capsules in acid phase for 2 hours buffered at pH 6.8 with and without SDS. FIG. 63 shows results of dissolution studies of rifaximin SD capsules in acid phase in a phosphate buffer at pH 6.8 with 0.45% SDS compared to amorphous rifaximin. As shown in the FIGS. 61-63 rifaximin SD near 100% dissolution is achieved in 0.45% SDS and the SD formulation dissolves more slowly than the amorphous rifaximin.

Example 5

Pharmacokinetic (PK) Studies of Solid Dispersion in Capsules

Presented herein are dog pharmacokinetics (PK) studies comparing various forms of rifaximin. PK following administration of rifaximin API in capsule, micronized API in capsule, nanocrystal API in capsule (containing surfactant), amorphous in capsule, and solid dispersion (SD) in capsule were tested.

In the SD dosage form, the polymer used was HPMC-AS at a drug to polymer ratio of 50:50. The formulation also comprised pluronic F127 and crosscarmellose sodium (see Example 4).

Figure 60:
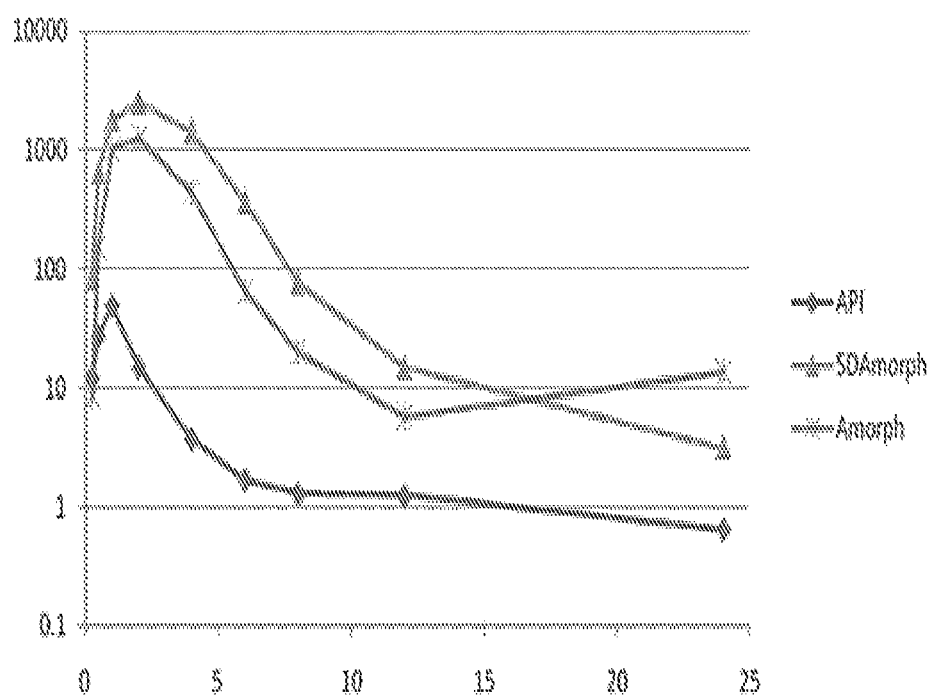
FIG. 60. Pharmacokinetic data of solid dispersion in dogs.

A brief study design: male beagle dogs (N=6, approximately 10 kg) received rifaximin 2200 mg in the dosage forms described above as a single dose (capsules, 275 mg, 8 capsules administered in rapid succession), in a cross-over design with one week washout between phases. Blood was collected at timed intervals for 24 h after dosage administration, and plasma was harvested for LC-MS/MS analysis. The mean concentrations are shown in FIG. 60.

Table 25 shows the PK parameters. From the table it can be seen that systemic exposure of the solid dispersion formulation is greater than that of amorphous or crystalline form (API) of rifaximin.

TABLE 25

PK Parameters of API, Amorphous and Solid Dispersion to Dogs

| ID | Half-life* h | Tmax h | Cmax ng/mL | AUClast h*ng/mL | AUCINF_obs h*ng/mL | AUC_0-24 h*ng/mL |
|---|---|---|---|---|---|---|
| 901_API | 16.76 | 0.5 | 65.5 | 101 | 118 | 101 |
| 902_API | 9.41 | 1 | 3.83 | 25 | 29 | 25 |
| 903_API | 10.03 | 1 | 197 | 344 | 360 | 344 |
| 904_API | 3.56 | 1 | 1.21 | 5 | 6 | 6 |
| 905_API | 2.94 | 1 | 1.53 | 5 | 6 | 6 |
| 906_API |  | 24 | 0.52 | 7 |  | 7 |
| mean | 6.98 | 1 | 44.93 | 81 | 104 | 82 |
| SD |  | [0.5-24] | 78.75 | 134 | 150 | 134 |
| 901_amorph | 5.38 | 1 | 536 | 1407 | 1421 | 1407 |
| 902_amorph | 5.93 | 2 | 4100 | 12258 | 12762 | 12258 |
| 903_amorph | 6.25 | 2 | 1050 | 3375 | 3523 | 3375 |
| 904_amorph | 4.77 | 2 | 763 | 2291 | 2306 | 2291 |
| 905_amorph | 7.72 | 1 | 1200 | 2041 | 2059 | 2041 |
| 906_amorph | 5.63 | 2 | 704 | 2076 | 2090 | 2076 |
| mean | 5.88 | 2 | 1392.17 | 3908 | 4027 | 3908 |
| SD |  | [1-2] | 1348.24 | 4141 | 4334 | 4141 |
| 901_SD amorph | 6.66 | 2 | 491 | 1354 | 1394 | 1354 |
| 902_SD amorph | 2.04 | 2 | 6550 | 25140 | 25149 | 25140 |
| 903_SD amorph | 2.8 | 4 | 2410 | 10490 | 10508 | 10490 |
| 904_SD amorph | 2.24 | 1 | 1410 | 6343 | 6350 | 6343 |
| 905_SD amorph | 3.97 | 2 | 2860 | 7885 | 7895 | 7885 |
| 906_SD amorph | 4.89 | 2 | 1900 | 4532 | 4558 | 4532 |
| mean | 3.01 | 2 | 3026 | 10878 | 10892 | 10878 |
| SD |  | [1-4] | 2043.58 | 8267 | 8264 | 8267 |

*geometric mean
**median and range

API exposures were low, in keeping with what has been previously observed for rifaximin. In contrast, mean exposures (AUCinf) following amorphous and SD rifaximin administration were substantially higher, with ~40- and ~100-fold greater exposure, respectively, as compared with API. Variability was high in all three dose groups. In general, the shapes of all three profiles were similar, suggesting effects of the dosage forms on bioavailability without effects on clearance or volume of distribution.

Example 6

Human Clinical Studies

Figure 65A:
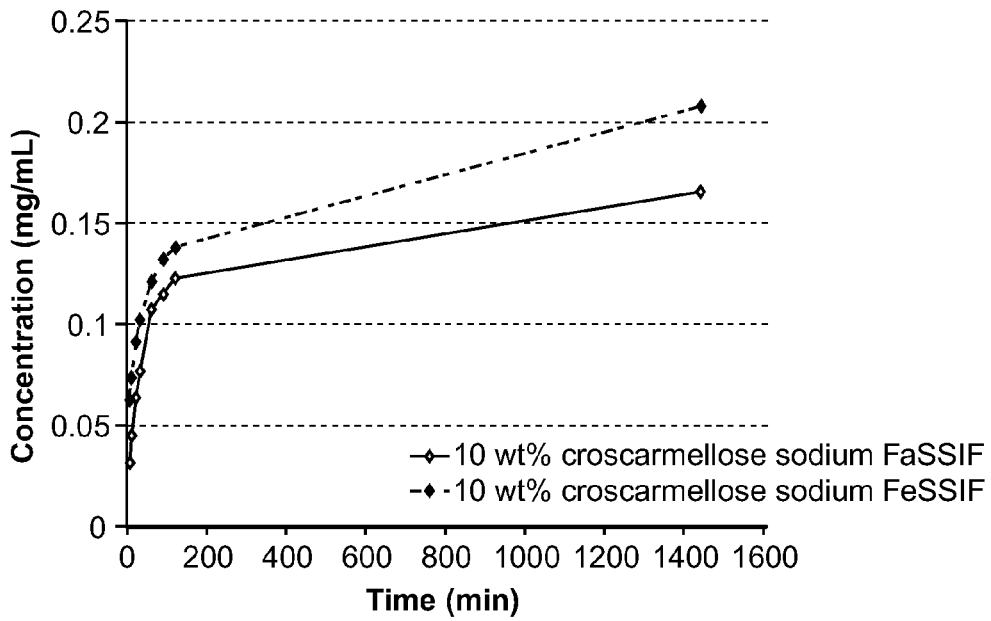
FIG. 65A kinetic solubility Rifamixin SD granules. 10% wt % CS sodium FaSSIF, 10% wt % CS sodium FeSSIF.
Figure 65B:
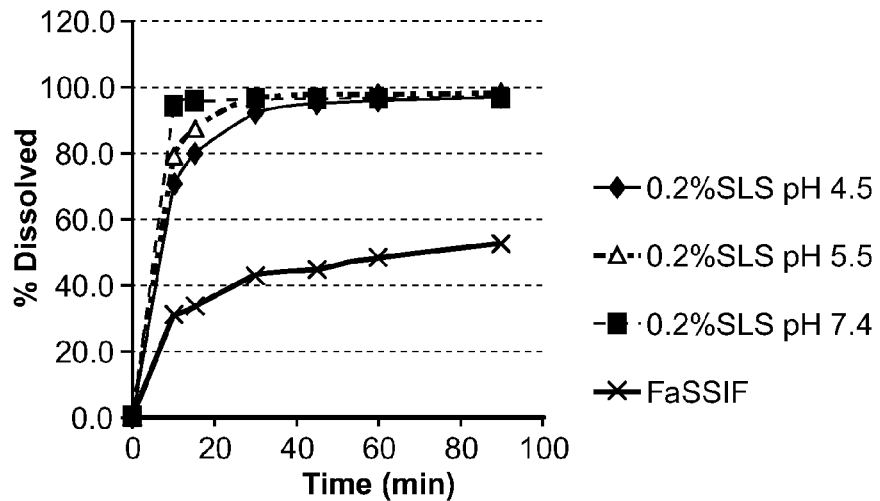
FIG. 65B dissolution profiles SDD tablet 10% CS. 0.2% SLS, pH4.5; 0.2% SLS, pH5.5; 0.2% SLS, pH 7.4; FaSSIF.
Figure 66A:
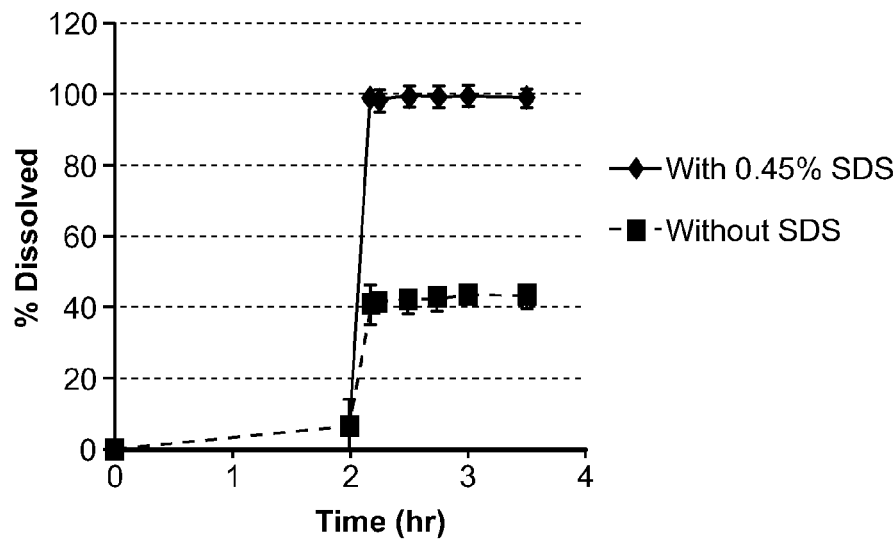
FIG. 66A acid phase 2 hours, buffer phase: P. Buffer, pH. 7.4. With 0.45% SDS; without SDS.
Figure 66B:
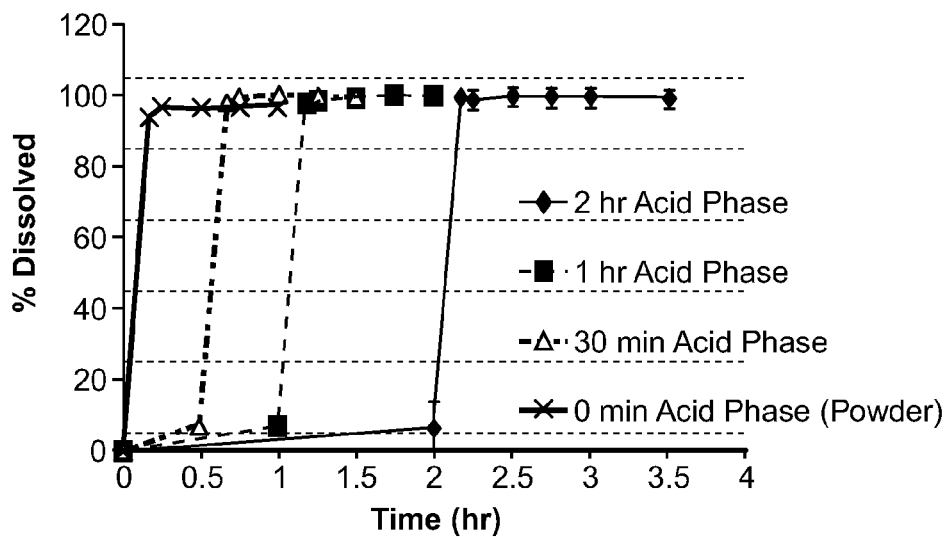
FIG. 66B acid phase: 0.1N HCl with variable exposure times, buffer phase: P. buffer, pH 7.4 with 0.45% SDS.

Rifaximin SDD with 10% CS formulation was used in human clinical studies. FIG. 65 shows the kinetic solubility of rifaximin SD granules 10% wt CS FaSSIF or 10% wt CS FeSSIF (a) and the dissolution profiles of SDD tablet 10% CS in 0.2% SLS at pH 4.5, 5.5 and 7.4. As shown in the FIG. 65, rifaximin SDD 100%, or near 100%, dissolution is achieved in 0.2% SLS, pH 4.5, 5.5 and 7.4. FIG. 66 shows that release can be delayed up to two hours and extended up to three hours.

Example 7

Effects of Media pH on Dissolution

Figure 67A:
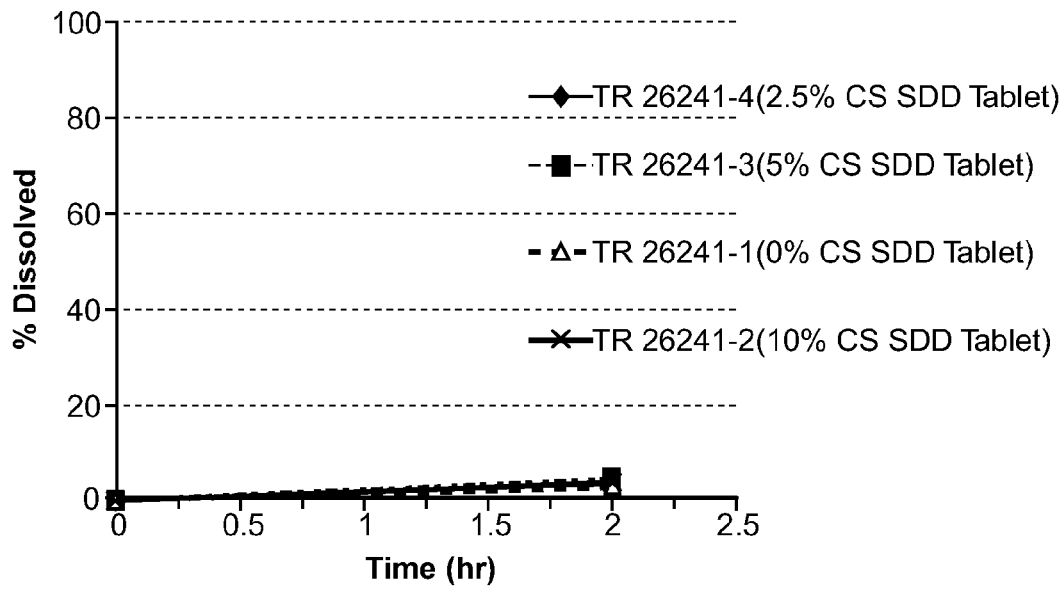
FIG. 67A Rifaxamin SDD tablet dissolution. Acid phase: 2 hours, pH 2.0, FIG. 67B Dissolution profiles 0.2% SDS at pH 4.5, SDD tablet dissolution at various levels of CS: 0%, 2.5%, 5%, and 10% CS.
Figure 67B:
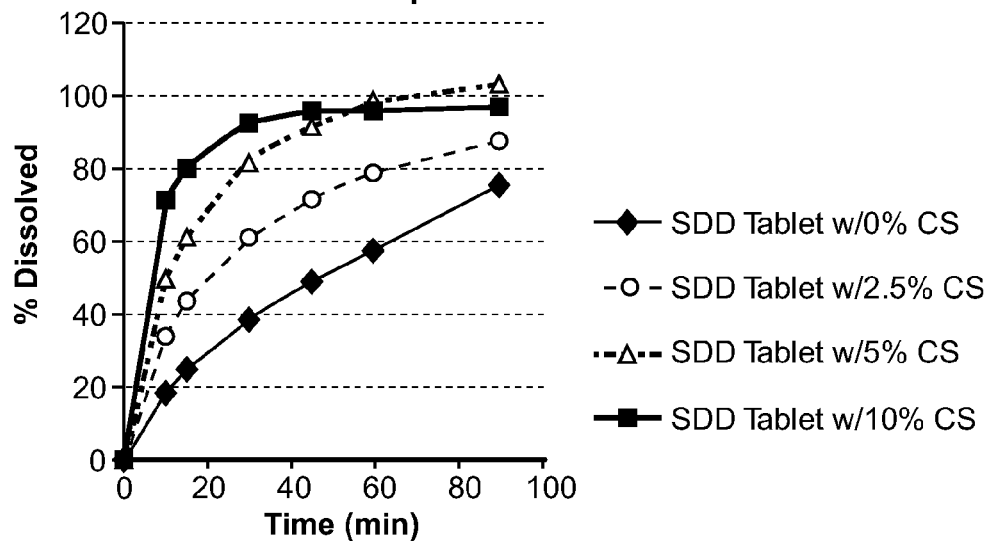
FIG. 67. Effects of media pH on dissolution.
Figure 68A:
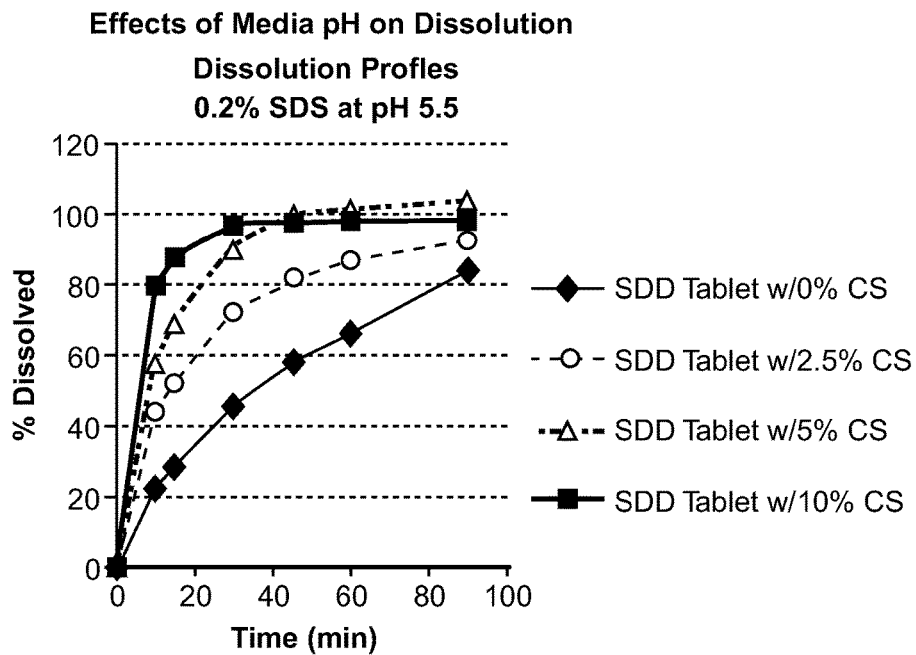
FIG. 68A Rifaxamin SDD tablet dissolution at various levels of CS: 0%, 2.5%, 5%, and 10% CS, 0.2% SDS at pH 5.5.
Figure 68B:
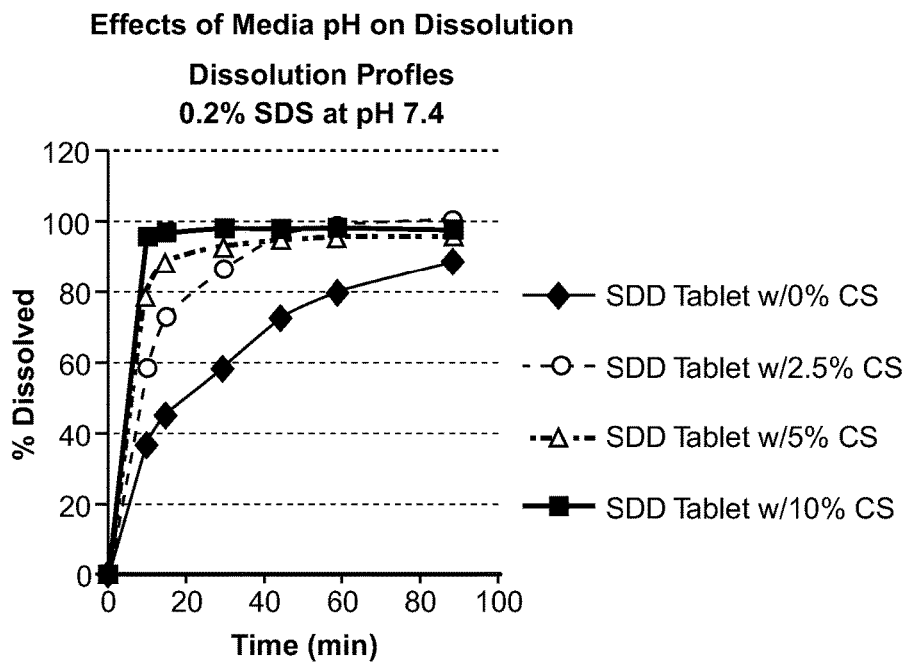
FIG. 68B Dissolution profiles SDD tablet dissolution at various levels of CS: 0%, 2.5%, 5%, and 10% CS, 0.2% SDS at pH 7.4.
Figure 69A:
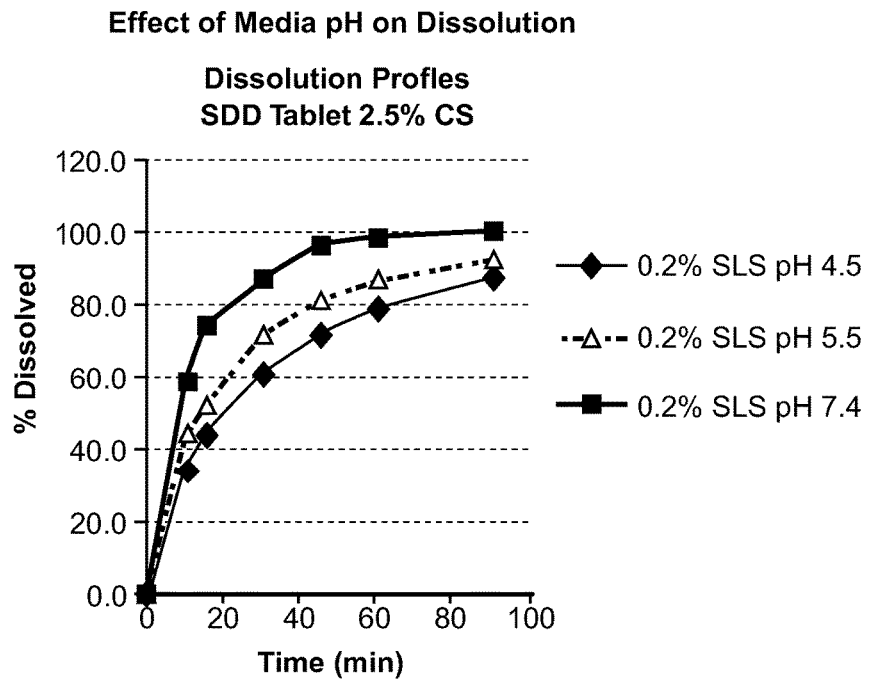
FIG. 69A Rifaxamin SDD tablet dissolution 2.5% CS, 0.2% SLS, pH4.5, 0.2% SLS, pH 5.5, 0.2% SLS, pH 7.4.
Figure 69B:
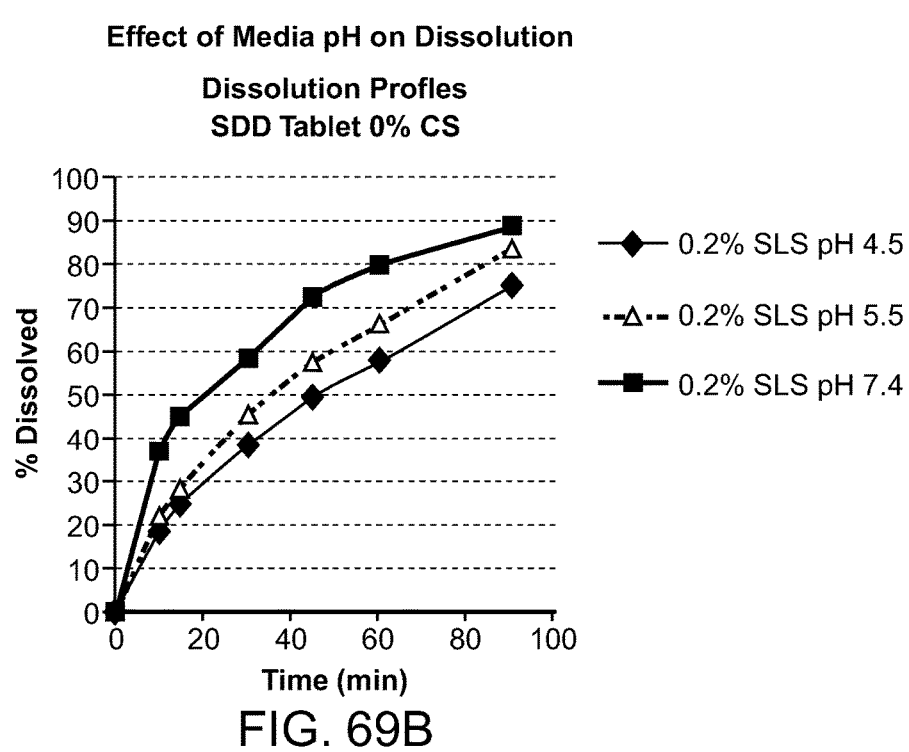
FIG. 69B Rifaxamin SDD tablet dissolution 0% CS, 0.2% SLS, pH4.5, 0.2% SLS, pH 5.5, 0.2% SLS, pH 7.4.
Figure 70A:
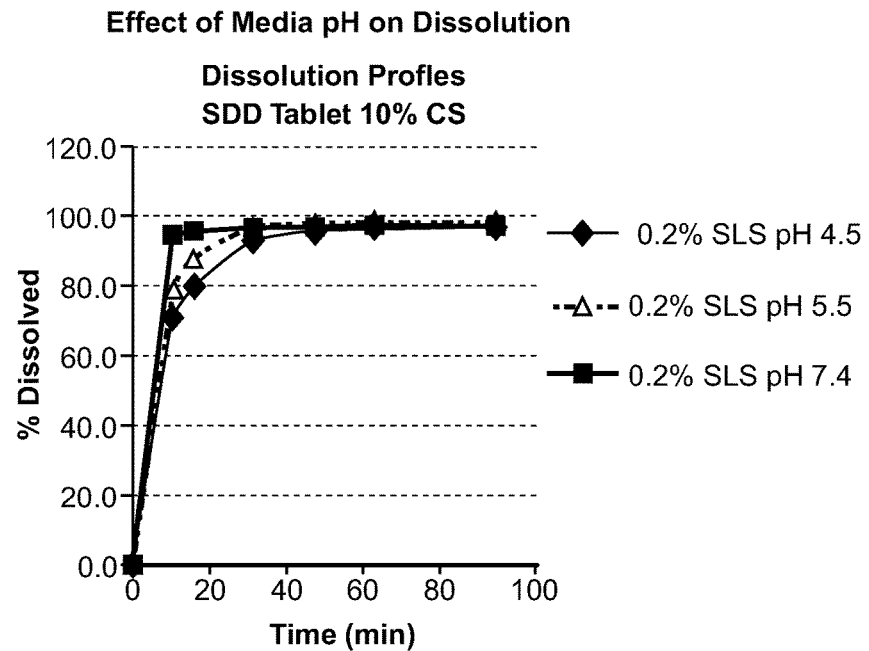
FIG. 70A Rifaxamin SDD tablet dissolution 10% CS, 0.2% SLS, pH4.5, 0.2% SLS, pH 5.5, 0.2% SLS, pH 7.4.
Figure 70B:
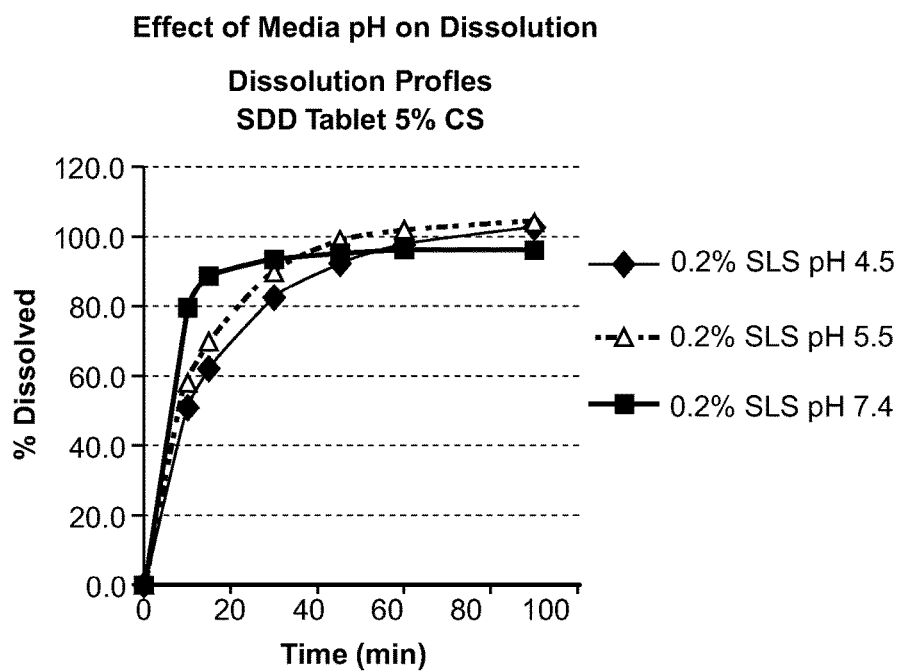
FIG. 70B Rifaxamin SDD tablet dissolution 5% CS, 0.2% SLS, pH4.5, 0.2% SLS, pH 5.5, 0.2% SLS, pH 7.4.
Figure 71A:
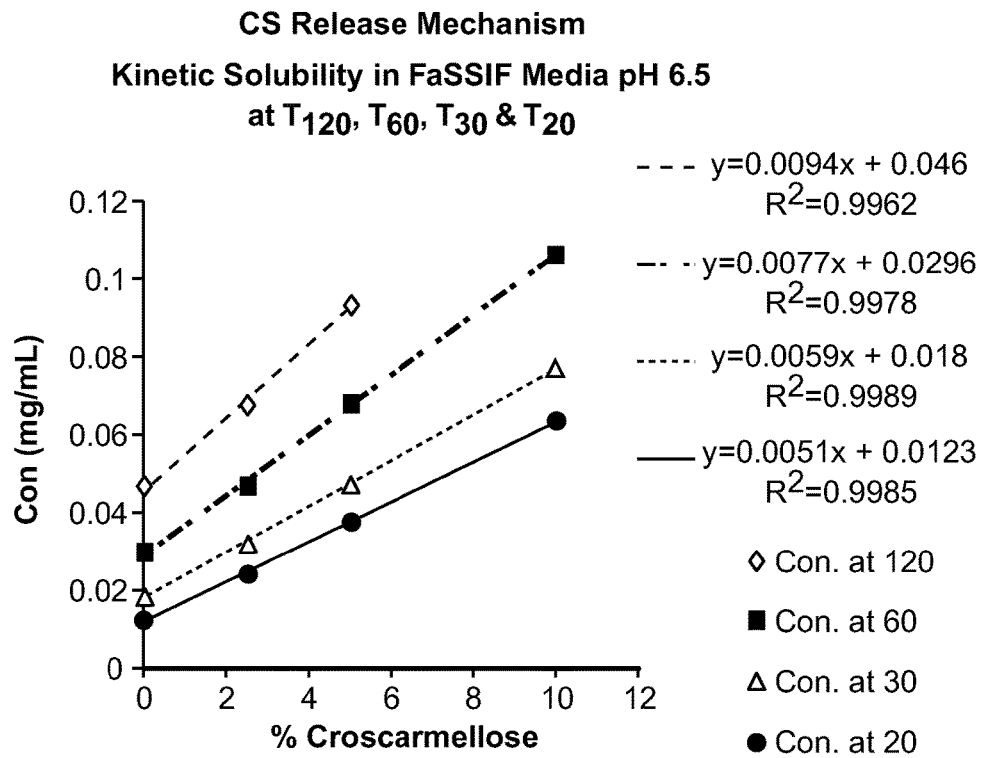
FIG. 71A Kinetic solubility in FaSSIF media, pH 6.5, FIG. 71B slope vs. time point.
Figure 71B:
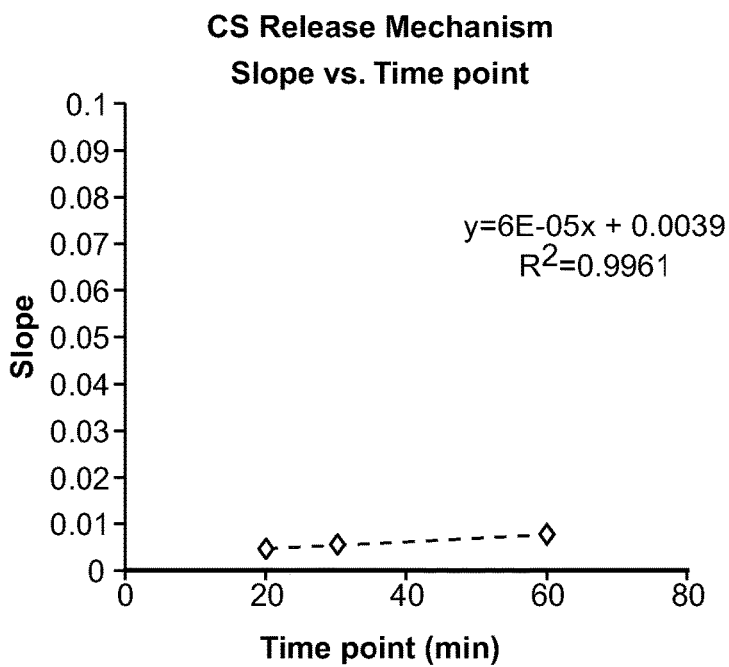
FIG. 71. CS release mechanism.

FIGS. 67-70 show the effects of media pH on Rifaximin SDD tablet SDD tablet dissolution at various levels of CS: 0%, 2.5%, 5%, and 10% CS. FIGS. 67 and 68 show dissolution profiles of SDD tablet with 0%, 2.5%, 5% or 10% CS in 0.2% SDS at 2 hours pH 2.0, pH 4.5, 0.2% SDS pH 5.5, or 0.2% SDS, pH 7.4. FIGS. 69 and 70 show the dissolution profiles of SDD tablet 2.5% CS, 0% CS, 10% CS and 5% CS in 0.2% SLS, pH4.5, 0.2% SLS, pH 5.5 and 0.2% SLS, pH 7.4. FIG. 71 shows CS release mechanism.

Example 8

Described herein are the preparation and characterization of rifaximin quaternary dispersions with antioxidants. Antioxidants used were butylated hydroxyanisole (BHA), butylated hydroxytoluene (BHT) and propyl gallate (PG).

Sample Preparation and Characterization

Three rifaximin quaternary samples were prepared by spray drying from methanol. Spray drying parameters are summarized in Table 26. Table 2 Parameters for Samples Prepared by Spray Drying

TABLE 26

| Sample ID | Inlet temp. (set, ° C.) | Aspirator % | Pump % | Inlet temp. (measured, ° C.) | Outlet temp. (measured, ° C.) | Spray rate (a) mL/min |
|---|---|---|---|---|---|---|
| 0.063 wt % of BHA in the dispersion | 120 | 95 | 45-35 | 120-124 | 61-49 | 19 |
| 0.063 wt % of BHT in the dispersion | 120 | 95 | 45-35 | 120-121 | 60-50 | 20 |
| 0.094 wt % of propyl gallate in the dispersion | 120 | 95 | 45-35 | 119-120 | 60-48 | 20 |

(a): flow rates are estimated based on initial pump % of 45%.

TABLE 27

Characterization of Rifaximin Quaternary Samples

| Habit/Description | Analysis | Results (b) |
|---|---|---|
| orange solids, irregular aggregates, no B/E | XRPD mDSC | x-ray amorphous 133° C. (midpoint, $T_g$) 0.3 J/g•° C. ($\Delta Cp$) |
| orange solids, irregular aggregates, no B/E | XRPD mDSC | x-ray amorphous 133° C. (midpoint, $T_g$) 0.4 J/g•° C. ($\Delta Cp$) |
| orange solids, irregular aggregates, no B/E | XRPD mDSC | x-ray amorphous 134° C. (midpoint, $T_g$) 0.4 J/g•° C. ($\Delta Cp$) |

A small sub-lot from each of spray dried materials was visually inspected by PLM and then characterized by XRPD and mDSC. Characterization results are summarized in Table 27.

Figure 72:
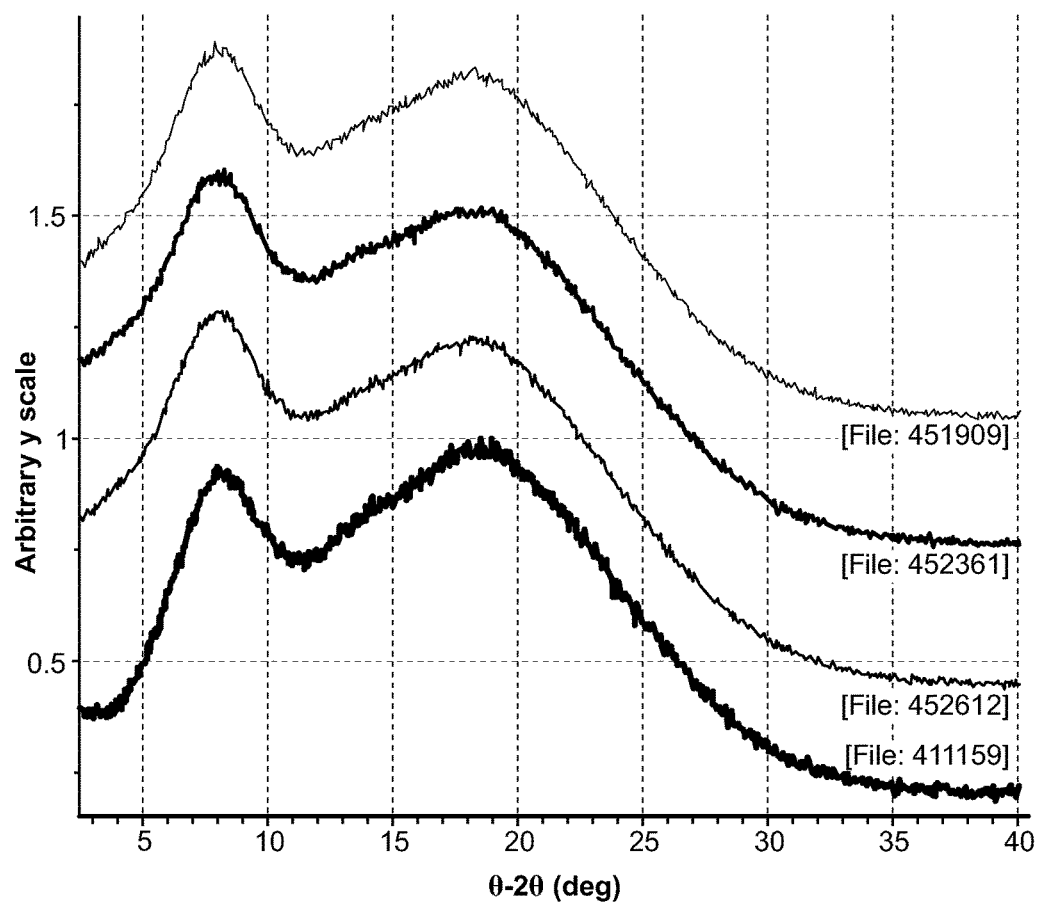
FIG. 72 depicts an overlay of XRPD patterns of rifaximin quaternary samples spray dried from methanol. The top is a rifaximin quaternary sample containing 0.063 wt % BHA. The second is rifaximin quaternary sample containing 0.063 wt % BHT. The third: is rifaximin quaternary sample containing 0.094 wt % PG, and the bottom is a spray dried rifaximin ternary dispersion.

The prepared materials are x-ray amorphous, as shown in FIG. 72 the overlay of XRPD patterns, which agree with their PLM observations.

Figure 73:
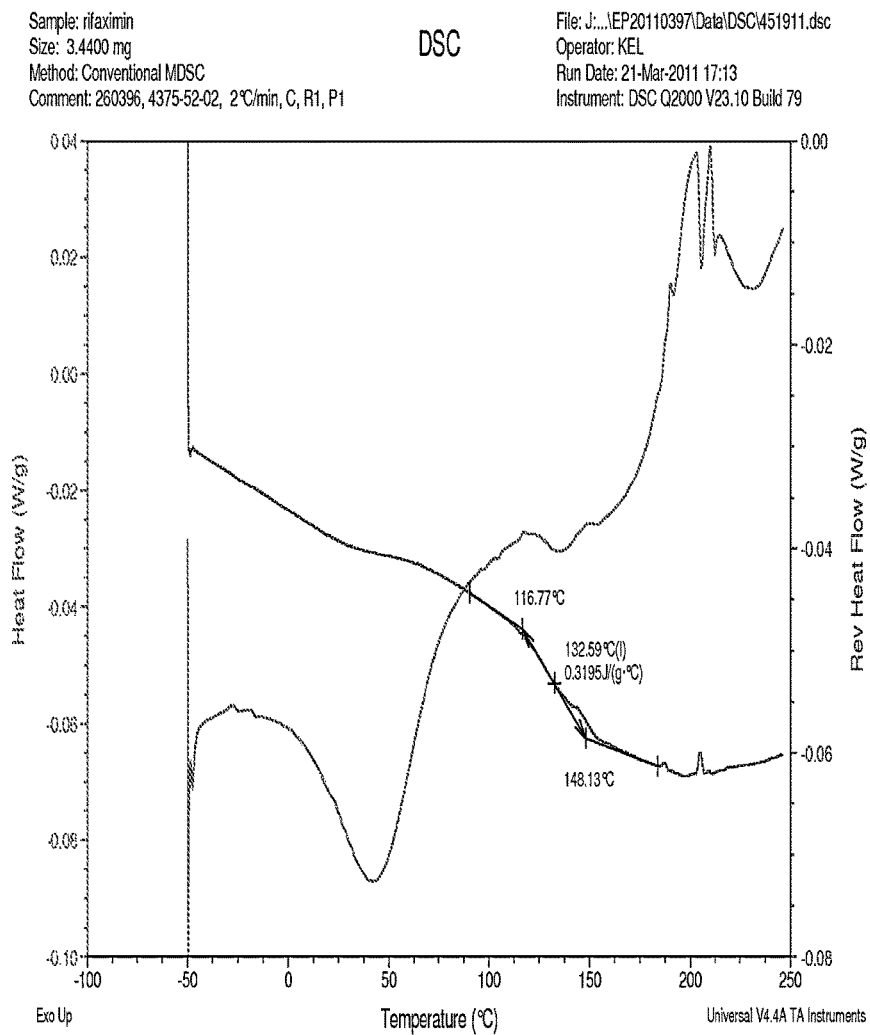
FIG. 73 depicts an mDSC thermogram of rifaximin quaternary sample containing 0.063 wt % BHA.
Figure 74:
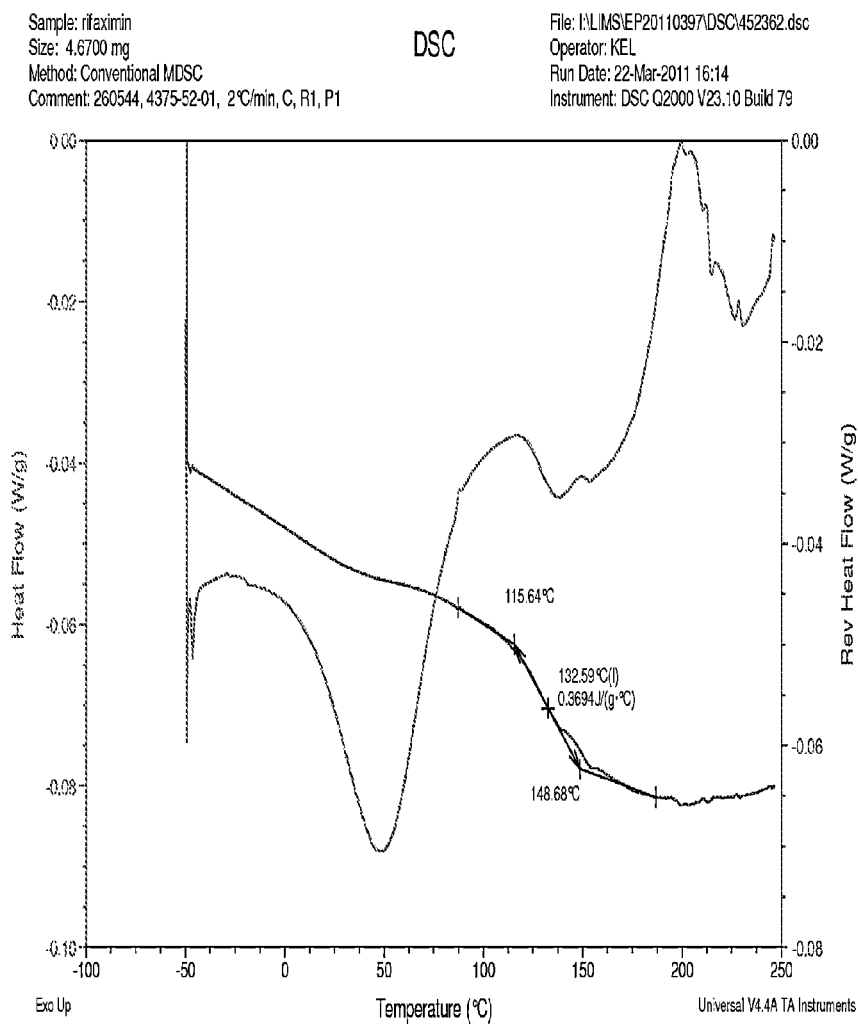
FIG. 74 depicts an mDSC thermogram of rifaximin quaternary sample containing 0.063 wt % BHT.
Figure 75:
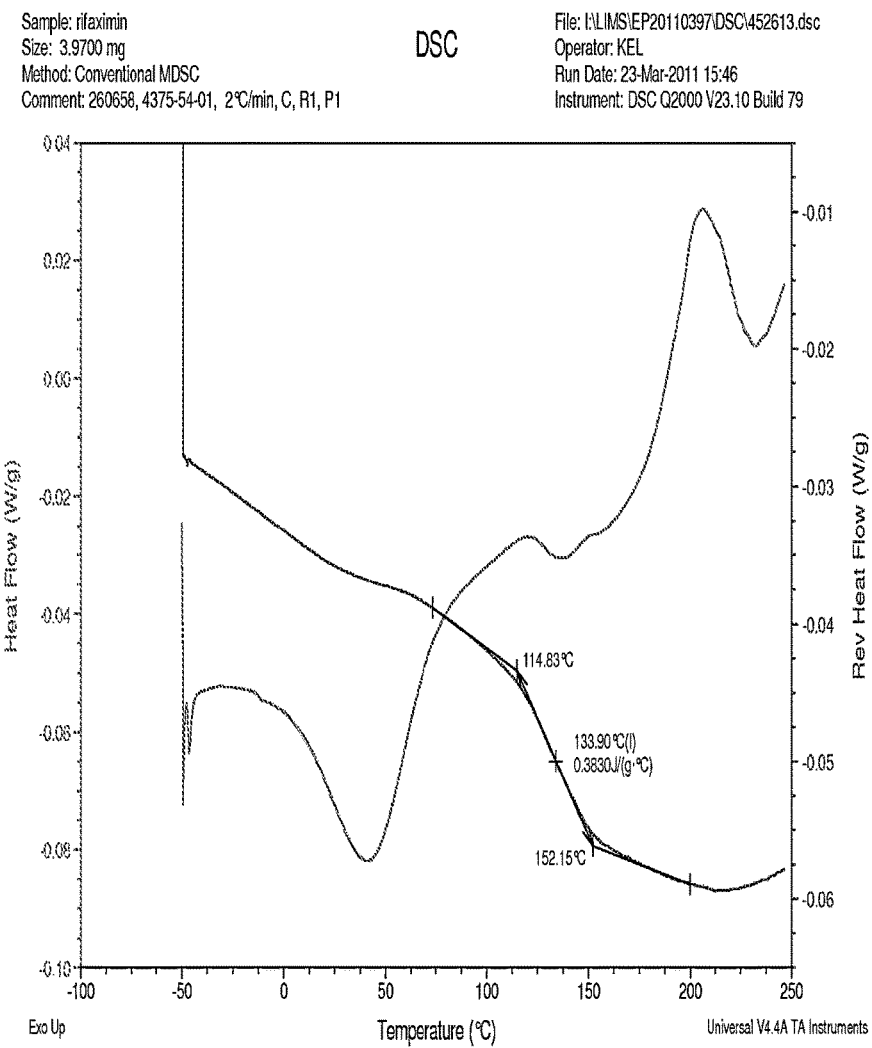
FIG. 75 depicts a mDSC thermogram of rifaximin quaternary sample containing 0.094 wt % PG.

In the mDSC, each of material displays a single apparent $T_g$ in the reversing heat flow signal at approximately 133° C. (FIG. 73, with 0.063 wt % BHA), 133° C. (FIG. 74, with 0.063 wt % BHT), and 134° C. (FIG. 75, with 0.094 wt % PG), which is consistent with the $T_g$ of the spray dried rifaximin ternary dispersion of 47.2:47.2:5.6 w/w/w/rifaximin/HPMC-AS MG/Pluronic F-127 (135 or 136° C.).

Example 9

Rifaximin Solid Dispersions

This example sets forth exemplary microgranules of rifaximin and pharmaceutical compositions comprising the same.

Spray dry dispersion (SDD), solid dispersion, amorphous solid dispersion are used interchangabley herein to refer to the rifaximin formulations.

The complete statement of the components and quantitative composition of Rifaximin Solid Dispersion Formulation (Intermediate) is given in Table 28

TABLE 28

Composition of Rifaximin Solid Dispersion Formulation

| Component | Quantity (%) | Function |
|---|---|---|
| Rifaximin Drug Substance | 42.48 | Active Ingredient |
| Hypromellose Acetate Succinate (HPMC-AS) | 42.48 | Solubility Enhancer |
| Poloxamer 407 | 5.04 | Surfactant |
| Croscarmellose Sodium | 10.00 | Dissolution Enhancer |

Composition of Rifaximin Solid Dispersion IR Capsule

TABLE 29

Composition of Rifaximin solid dispersion IR capsule

| Component | Quantity | Function |
|---|---|---|
| Rifaximin solid dispersion (amorphous) | 75 mg-275 mg* | Active ingredient |
| Hard Gelatin capsules Coni-Snap, Size 000, Transparent | 1 unit | Capsule |

*Rifaximin dose equivalent

Description of Manufacturing Process and Process Controls

Manufacturing Process for Rifaximin Solid Dispersion Formulation

Table 30 sets forth the manufacture of Rifaximin solid dispersion microgranules

TABLE 30

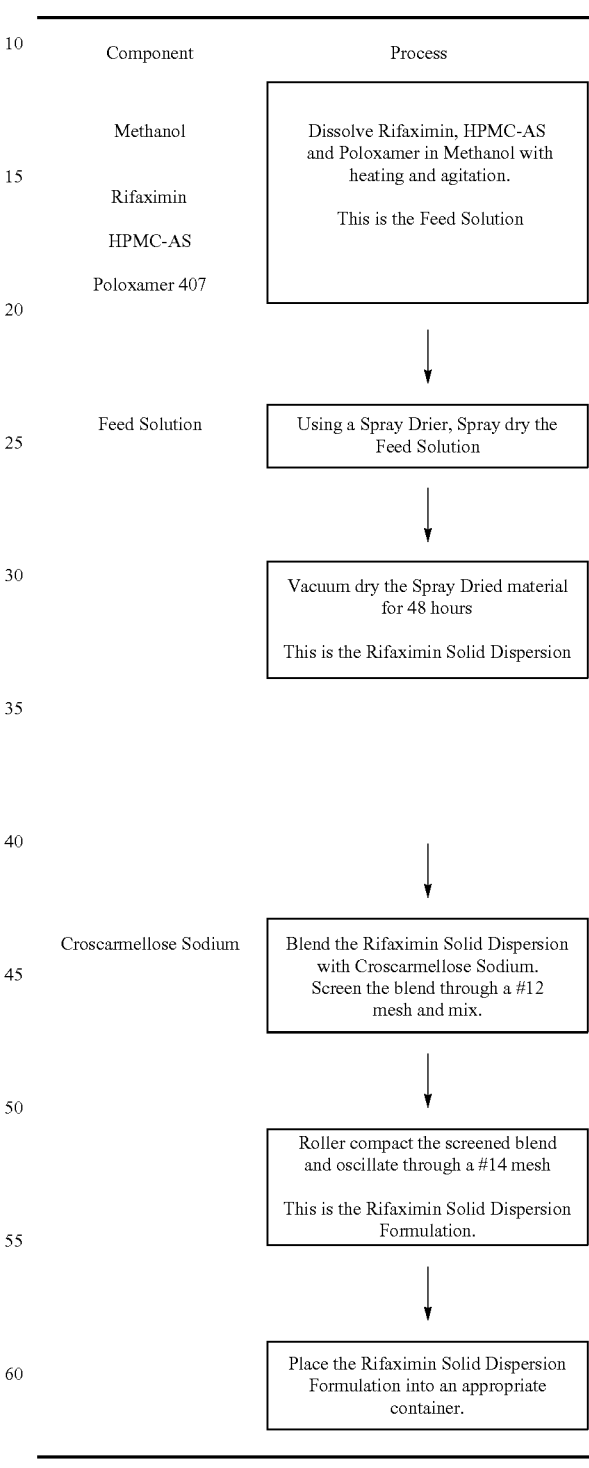

Manufacturing Process for Rifaximin Solid Dispersion IR Capsules

The manufacturing process the Rifaximin solid dispersion IR capsules is given in Table 31.

TABLE 31

Manufacture of Rifaximin solid dispersion microgranules in IR capsules

| Component | Process |
|---|---|
| Rifaximin solid dispersion Formulation | Transfer the required amount of Rifaximin solid dispersion Formulation into each capsule and close the capsule. |
| | ↓ |
| | Place each capsule individually into appropriate container |

Exemplary spray drying processes are set forth in Table 32.

Three roller compacted material of Amorphous Solid Dispersion Rifaximin with varying levels (0, 2.5%, 5%) of croscarmellose sodium were dissolution tested. Results are compared to dissolution of the rifaximin granules with 10% croscarmellose sodium.

Dissolution Studies with USP Paddle Method

Dissolution tests were performed on as received roller compacted materials of Solid Dispersion Rifaximin with 0, 2.5 wt %, and 5 wt % croscarmellose sodium. Powders of solids were directly added into pH 6.5 FaSSIF buffer with gentle agitation of the media (50 rpm paddle stirrer) at 37° C. for 24 hrs.

At designated time points of 5, 10, 20, 30, 60, 90, 120, 240 and 1440 minutes, aliquots were removed from each of the samples. Analysis of the date indicates that an increase in rifaximin concentration is apparent with the rising croscarmellose sodium level in materials, particularly in the early stage of the dissolution. After 24 hrs, the rifaximin concentration from granules containing 5 wt % croscarmellose sodium is similar to granules with 10 wt % croscarmellose sodium.

TABLE 32

Spray Drying Process:

Spray Dryer-PSD 1
Two Fluid Niro Nozzle
Nozzle orifice-1 mm
Inlet gas temperature-125 ± 3 deg C.
Process gas flow (mmH2O)-44
Atomizing gas pressure-1 bar
Feed rate-4.7 kg/Hr
Outlet temperature-55 ± 3 deg C.
Solution temperature-36 deg C.
Post spray drying vacuum dry at 40 deg C. for 48 hrs

| Ingredients | Micronized Caps % | Micronized Caps g/dose | API Caps % | API Caps g/dose | Amorphous Caps % | Amorphous Caps g/dose | Amorphous SD caps % | Amorphous SD caps g/dose | Micronized Tab % | Micronized Tab g/dose |
|---|---|---|---|---|---|---|---|---|---|---|
| Rifaximin | 95.5 | 2.2 | 47.2 | 2.2 | 51.7 | 2.2 | 42.47 | 2.2 | 50 | 2.2 |
| Ac-di-sol | 4.5 | 0.1 | 5 | 0.23 | 5 | 0.21 | 10.02 | 0.52 | 7.5 | 0.33 |
| Mannitol 160C | — | — | 47.8 | 2.23 | 43.3 | 1.84 | — | — | — | — |
| Pluronic 188 | — | — | — | — | — | — | 5.04 | 0.26 | — | — |
| HPMC AS | — | — | — | — | — | — | 42.47 | 2.2 | — | — |
| Avicel 113 | — | — | — | — | — | — | — | — | 26 | 1.14 |
| Avicel 112 | — | — | — | — | — | — | — | — | 15 | 0.66 |
| Magnesium Stearate | — | — | — | — | — | — | — | — | 1 | 0.04 |
| Cab-o-sil | — | — | — | — | — | — | — | — | 0.5 | 0.02 |
| Avicel CL-611 | — | — | — | — | — | — | — | — | — | — |
| Mannitol 160C | — | — | — | — | — | — | — | — | — | — |
| Total | 100 | 2.3 | 100 | 4.66 | 100 | 4.26 | 100 | 5.18 | 100 | 4.4 |

Example 10

Characterization of Drug Product Samples Containing Rifaximin Solid Dispersion

Disclosed herein is dissolution data for roller compacted materials of Solid Dispersion Rifaximin with varying levels (0, 2.5%, 5%, and 10%) of croscarmellose sodium.

Example 11

Characterization of Rifaximin Solid Dispersion Powder 42.48% w/w

Described herein is the characterization of Rifaximin Solid Dispersion Powder 42.48% w/w. Dissolution testing was also performed on the material at pH 6.5 in FaSSIF at 37° C.

A sample of rifaximin ternary dispersion was characterized by XRPD, mDSC, TG-IR, SEM and KF.

Figure 76:
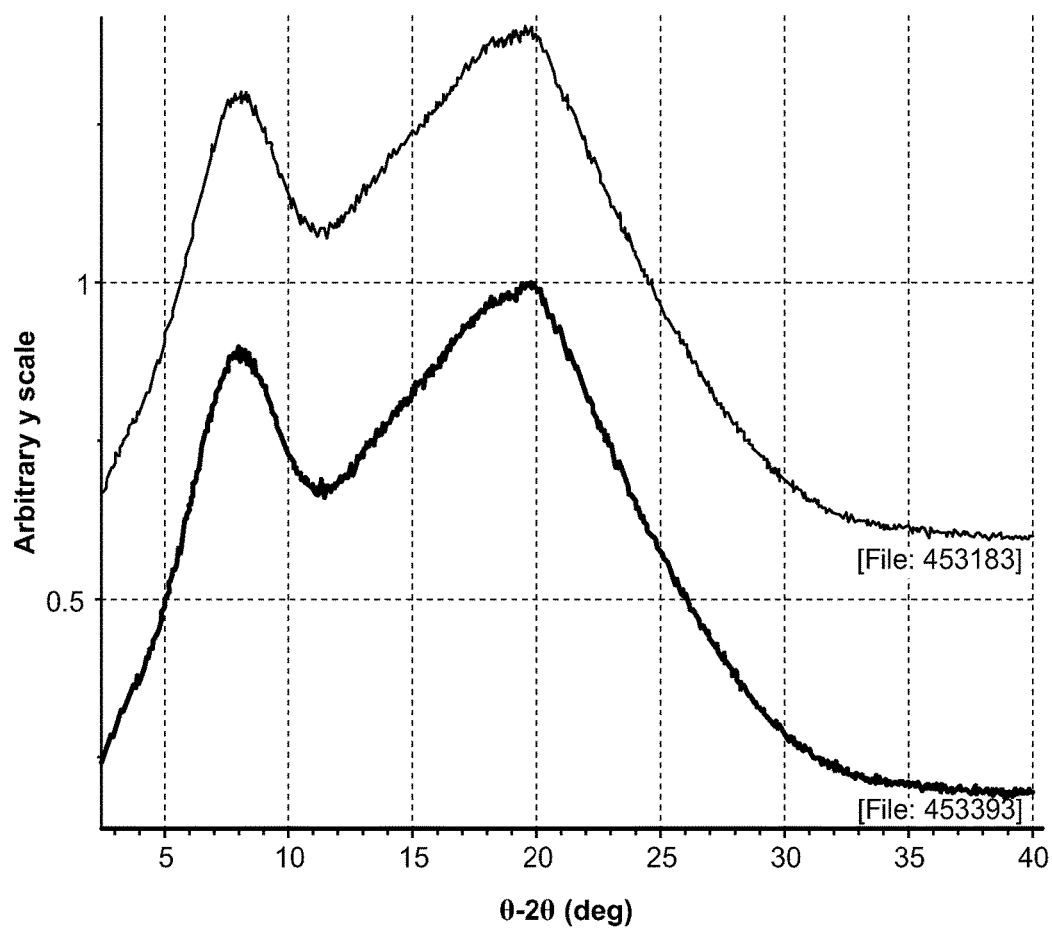
FIG. 76 depicts an XRPD pattern comparison of rifaximin solid dispersion powder 42.48% w/w with roller compacted material of rifaximin blend. Top: Rifaximin Solid Dispersion Powder 42.48% w/w; Bottom: roller compacted rifaximin blend.

X-ray powder diffraction (XRPD) analysis using a method for Rifaximin Solid Dispersion Powder 42.48% w/w was conducted. The XRPD pattern by visual inspection is x-ray amorphous with no sharp peaks (FIG. 76). By mDSC a single apparent $T_g$ is observed from the step change in the reversing heat flow signal at approximately 134° C. with a heat capacity change at $T_g$ of approximately 0.36 J/g·° C.

Thermogravimetric analysis coupled with infra-red spectroscopy (TG-IR) was performed to analyze volatiles generated upon heating. The total weight loss of sample was approximately 0.4 wt % to 100° C., and a dramatic change in the slope occurs at approximately 190° C. which is likely due to decomposition. The Gram-Schmidt plot corresponds to the overall IR intensity associated with volatiles released by a sample upon heating at 20° C./min Gram-Schmidt indicates that volatiles are released upon heating after ~8 min, and volatiles were identified as residual methanol from the processing solvent in spray drying and possible acetic acid from HPMC-AS MG.

KF analysis indicates that the material contains 1.07 wt % water [(1.00+1.13)/2=1.07%].

Example 12

Methods for Spray Drying Rifaximin Ternary Dispersion (50:50 w/w Rifaximin:HPMC-AS MG with 5.9 Wt % Pluronic F-127)

Provided herein are procedures to spray dry Rifaximin ternary dispersion (50:50 w/w Rifaximin:HPMC-AS MG with 5.9 wt % Pluronic F-127).

Rifaximin ternary dispersions (50:50 w/w Rifaximin: HPMC-AS MG with 5.9 wt % Pluronic F-127) were prepared from methanol using Büchi B-290 Mini Spray Dryer in closed mode suitable for processing organic solvents. Ingredients are listed in Table 33 below:

TABLE 33

| No. | Component | mg/g | Purpose |
|---|---|---|---|
| 1 | Rifaximin | 472 | active pharmaceutical ingredient |
| 2 | Hydroxypropylmethyl cellulose acetate succinate (HPMC-AS), Type MG | 472 | stabilizing agent |
| 3 | Pluronic F-127 | 56 | wetting agent |
| 4 | Methanol | — | volatile; removed during process |

Rifaximin ternary dispersions were prepared by spray drying in both small scale (~1 g API) and large scale (≥34 g API in a single batch).

For a small-scale sample, rifaximin and then the methanol were added into a clean flask. The mixture was stirred at ambient for ~5 min to give a clear solution. HPMC-AS MG and Pluronic F-127 were added in succession and the sample was stirred for ~1 hr. An orange solution was obtained.

For a large-scale sample, a solution was prepared at ~40° C. Rifaximin and then methanol were added to a clean flask and the mixture was stirred at ~40° C. for ~5 min until clear. HPMC-AS MG, and then Pluronic F-127 were added into the rifaximin solution under stirring at ~40° C. The sample continued to stir for ~1.5 hr to 2 hr at this temperature. A dark red solution was obtained. The sample was removed from the hot plate and left at ambient to cool.

Experimental conditions to prepare Rifaximin ternary solutions are summarized in Table 34 below:

TABLE 34

| Solvent | weight (API/HPMC AS MG/Pluronic F127, g) | Temperature | Concentration (g/L) |
|---|---|---|---|
| methanol, 100 mL | 1.0535/1.0529/0.1249 | ambient | 22.3 |
| methanol, 1000 mL | 34.07/34.07/4.02 | ~40 C. | 72.2 |
| methanol, 1250 mL | 50.34/50.32/5.94 | ~40 C. | 85.3 |
| methanol, 1250 mL | 50.16/50.14/5.92 | ~40 C. | 85.0 |
| methanol, 1250 mL | 50.05/50.06/5.91 | ~40 C. | 85.0 |

During spray drying process, both the small and large scale rifaximin ternary solutions were kept at ambient temperature. The Pump % was decreased during process in attempt to control outlet temperature above 40° C. The operating parameters used for processing are presented in Table 35 below.

TABLE 35

| Description (a) | Inlet temp. (set, ° C.) | Aspirator % | Pump % | Inlet temp. (measured, ° C.) | Outlet temp. (measured, ° C.) | Spray rate (b) mL/min |
|---|---|---|---|---|---|---|
| 50:50 | 120 | 95 | 35 | 120 | 60-55 | 10.4 |
| Rifaximin:HPMC-AS | 120 | 95 | 65-30 | 120-119 | 61-42 | 23 |
| MG | 120 | 95 | 50-30 | 120-119 | 67-43 | 16 |
| 5.9 wt % Pluronic F | 120 | 95 | 50-30 | 120-119 | 65-43 | 16 |
| 127 | 120 | 95 | 50-30 | 120-119 | 67-43 | 16 |

(a): 50:50 is approximate ratio of Rifaximin to polymer, by weight; 5.9 wt % Pluronic is weight fraction to 50:50 Rifaximin:HPMC-AS MG dispersion.
(b): flow rates are estimated. Flow rate for 4103-41-01 was measured at pump 35%; for 4103-56-01 was measured at pump 65%, while for others were measured at pump 50%.

Solids recovered after spray drying were dried at 40° C. under vacuum for 24 hours and then stored at sub-ambient (freezer) over desiccant.

Example 13

Non-Clinical Data-Form/Formulation Comparison and Dose Ranging in Dogs

Figure 77:
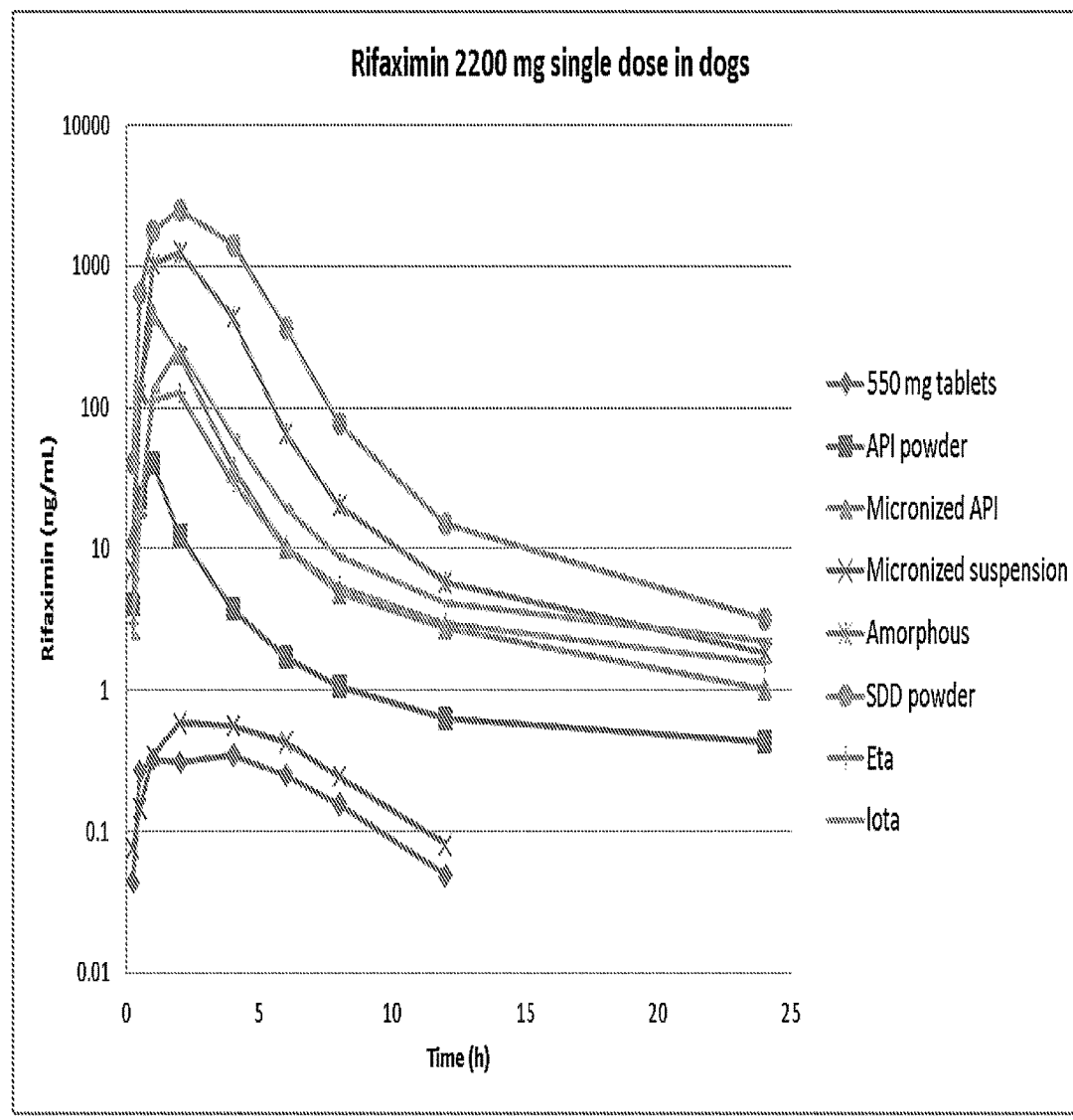
FIG. 77 depicts the pharmacokinetics of rifaximin following administration of varying forms and formulations following a single oral dose of 2200 mg in dogs.

Described herein is non-clinical data, form/formulation comparison in dogs and SDD dose ranging in dogs. FIG. 77 indicates the results of two studies conducted to characterize the pharmacokinetics of rifaximin following administration of varying forms and formulations following a single oral dose. Blood samples were collected at timed intervals over the 24 h after single dose administration (2200 mg total dose in each case) and processed to plasma for analysis of rifaximin concentrations. PK parameters were estimated by noncompartmental methods. The results are shown in FIG. 77. Of the forms/formulations shown, the spray-dried dispersion showed that the highest exposure, and therefore the highest bioavailability, resulted from administration of the SDD formulation (dosed as SDD powder in gelatin capsules). In order of decreasing exposure among forms dosed in gelatin capsule formulation, SDD>amorphous>iota>micronzed>eta>current crystalline API. Lower in systemic exposure than all of those are the micronized suspension formulation (reconstituted powder for oral suspension) and the current 550 mg Xifaxan tablet. Table 36, below, shows Pk parameters for dog forms.

TABLE 36

| HL_Lambda_z | Tmax h | Cmax h | AUCall ng/mL | AUCINF_obs h*ng/mL | h*ng/mL |
|---|---|---|---|---|---|
| Eta | 9.70 | 1.5 | 162.28 | 434.14 | 608.14 |
| Iota | 6.56 | 2 | 276.50 | 718.23 | 739.94 |
| Amorphous | 5.82 | 2 | 1392.17 | 3907.84 | 4026.86 |
| API capsules | 5.64 | 1 | 44.93 | 81.20 | 103.83 |
| SDD | 3.16 | 2 | 2603.50 | 9290.71 | 9308.83 |
| Micronized capsules | 8.10 | 1 | 473.43 | 894.65 | 905.97 |
| Micronized suspension | 5.22 | 3 | 0.68 | 5.11 | 8.41 |
| Micronized tablets | 4.77 | 5 | 0.83 | 6.81 | 10.20 |
| Nanocrystal capsules | 5.01 | 5 | 0.99 | 9.05 | 8.70 |

Figure 78:
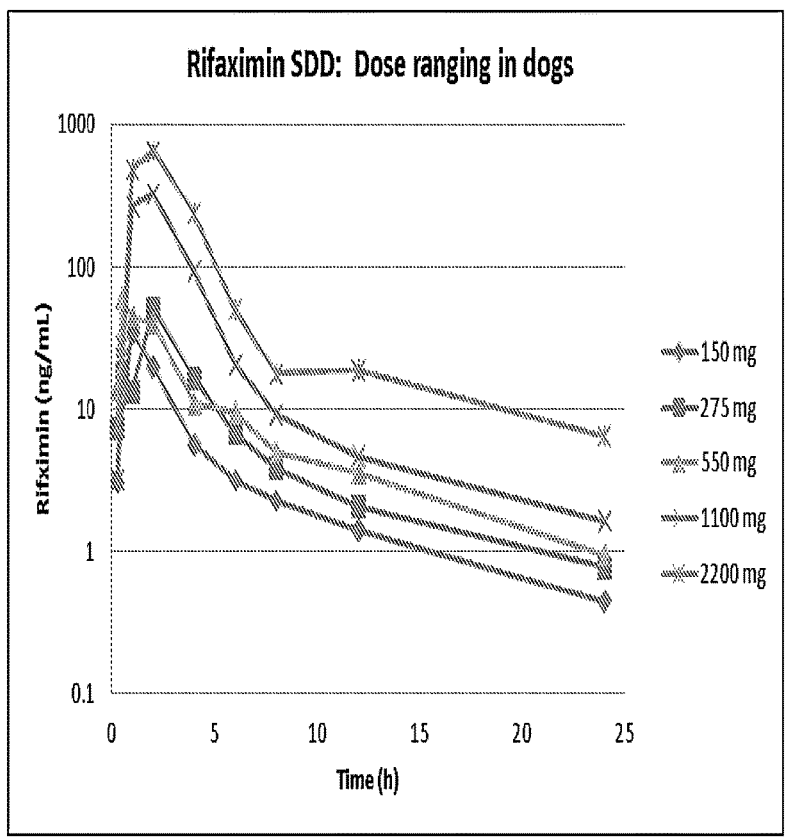
FIG. 78 depicts Rifaximin SDD in dogs.

FIG. 78 shows the results of the dog dose escalation, in which dogs received single doses of the SDD formulation in capsules, at doses from 150 mg to 2200 mg. The results indicate an essentially linear dose escalation (increases in exposure that are approximately proportional to increase in dose) up to 550 mg, followed by a greater-than-proportional increase at 1100 mg and 2200 mg. This is quite unusual in the linear range in that the current crystalline form of rifaxmin does not dose escalate, generally, exposure does not increase substantially on increasing dose. The greater than dose proportional increase on increasing dose is also remarkable and suggests that, at the higher doses, rifaximin is saturating intestinal P-glycoprotein transport that would otherwise limit systemic absorption, thereby allowing increased absorption.

Example 14

Human Studies

Figure 79:
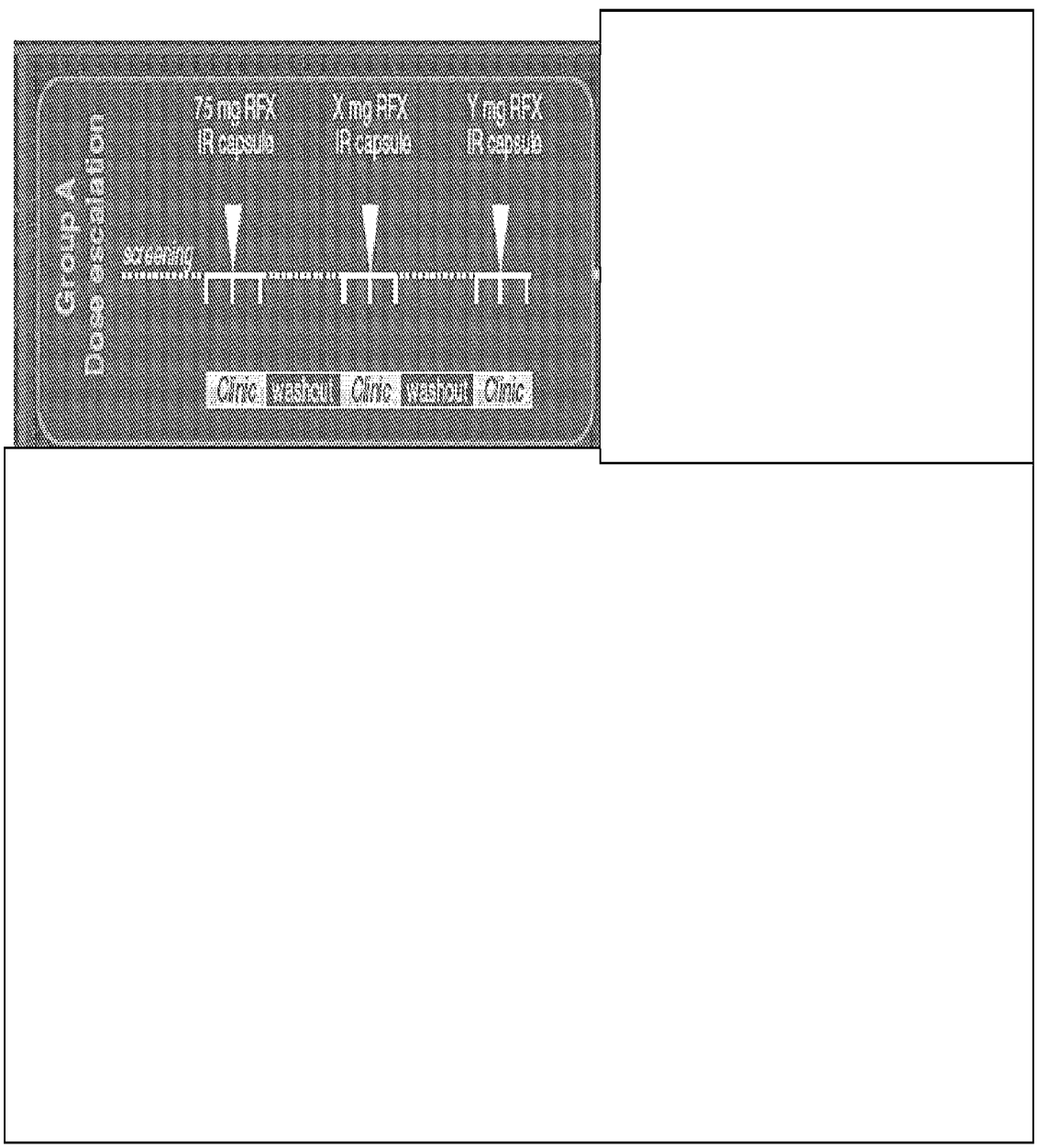
FIG. 79 depicts the quotient study design.
Figure 81:
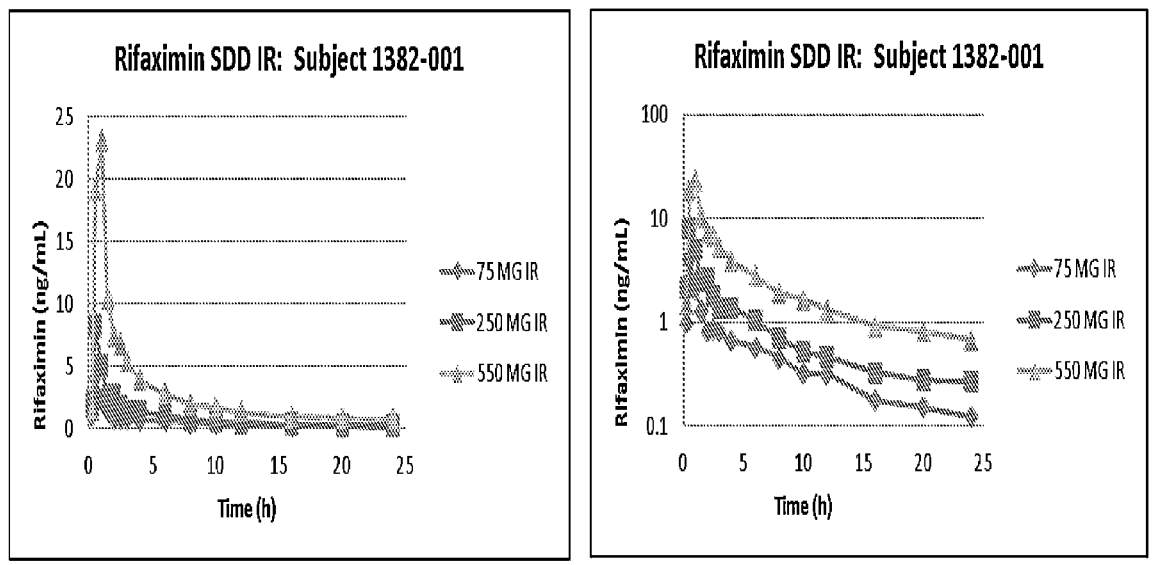
FIG. 81 depicts representative subject data from a dose escalation study.
Figure 82:
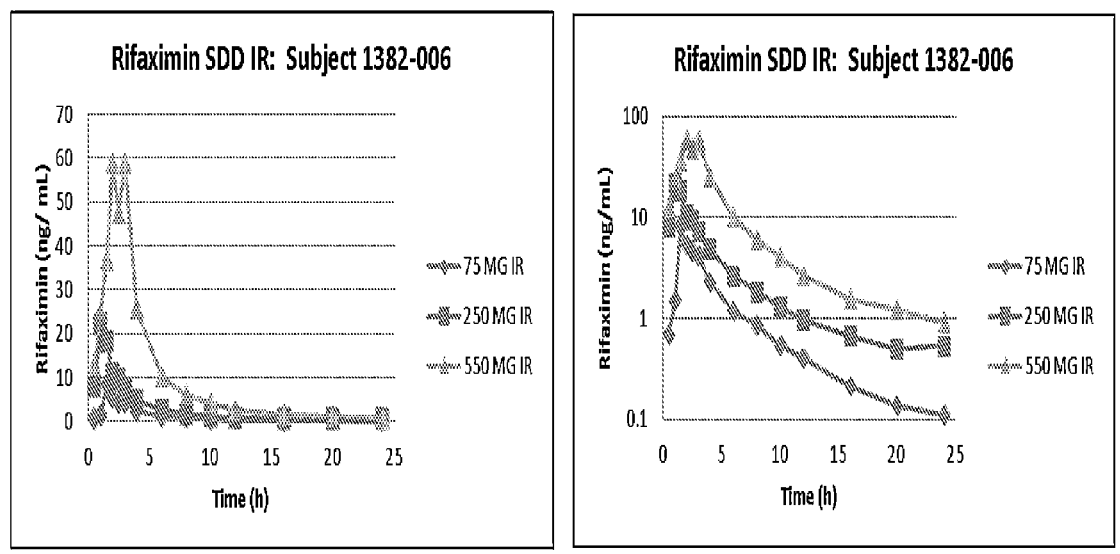
FIG. 82 depicts representative subject data from a dose escalation study.
Figure 83:
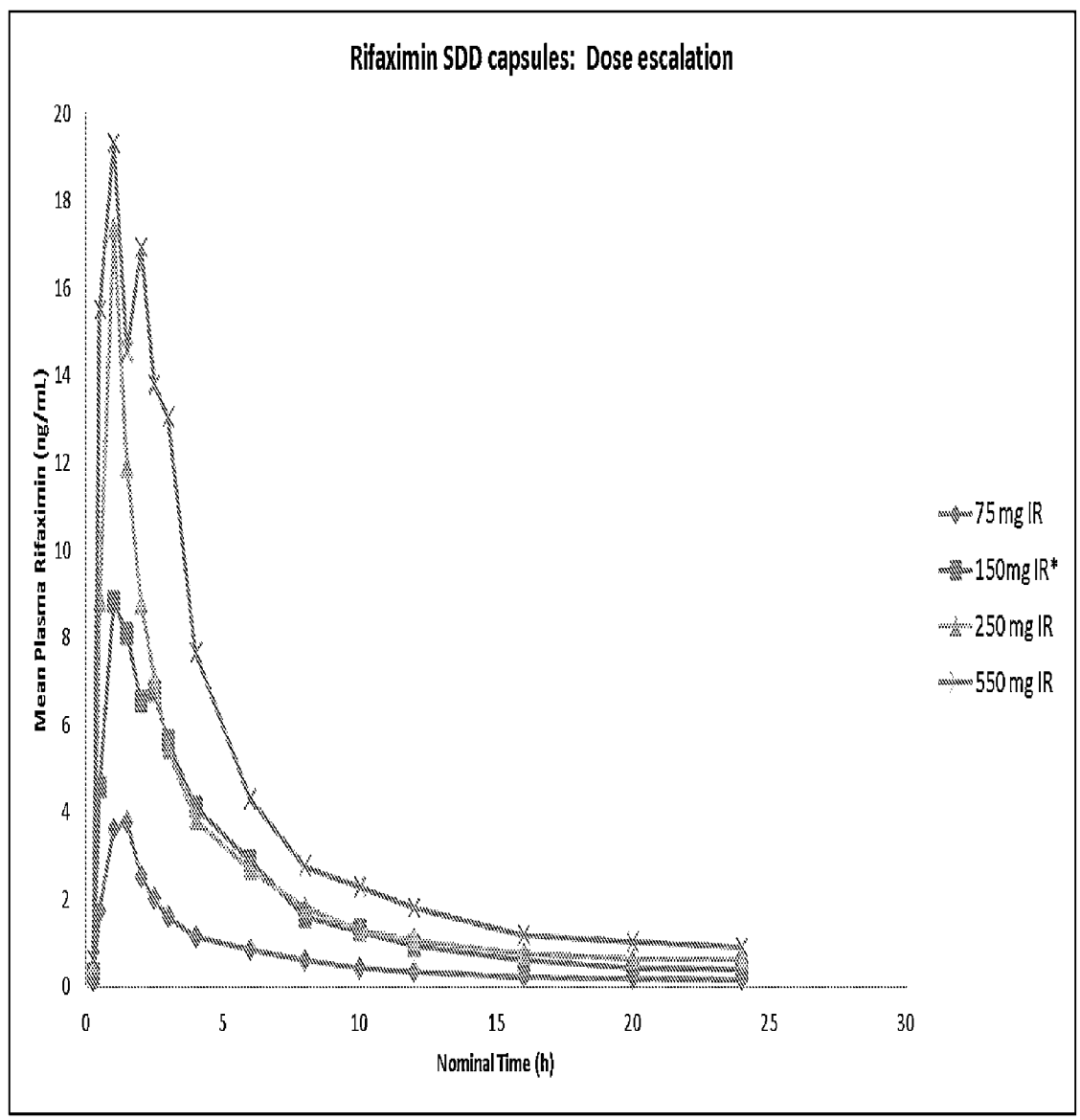
FIG. 83 depicts mean dose escalation data, on a linear scale.
Figure 84:
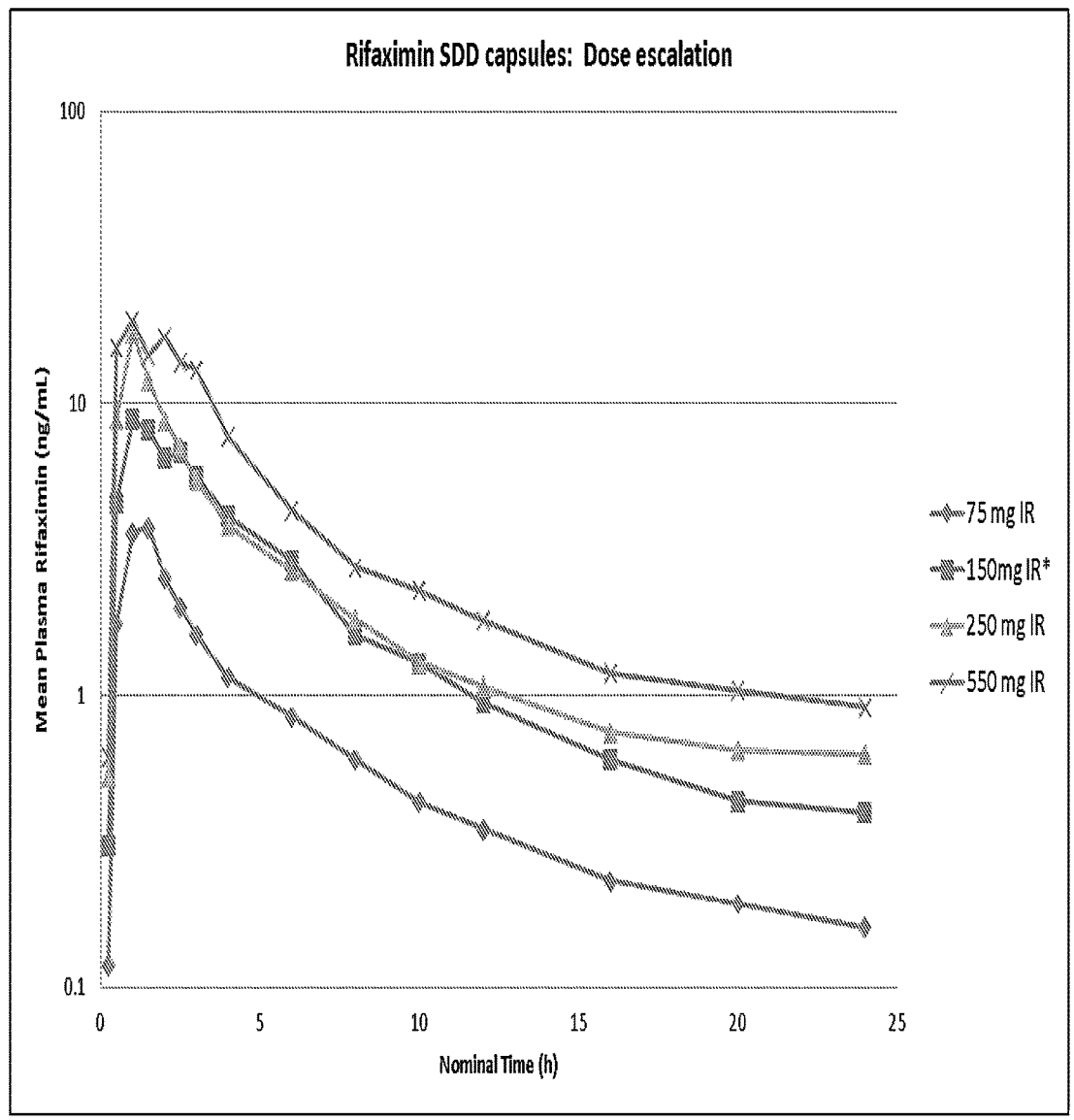
FIG. 84 depicts mean dose escalation data, on a log scale.
Figure 85:
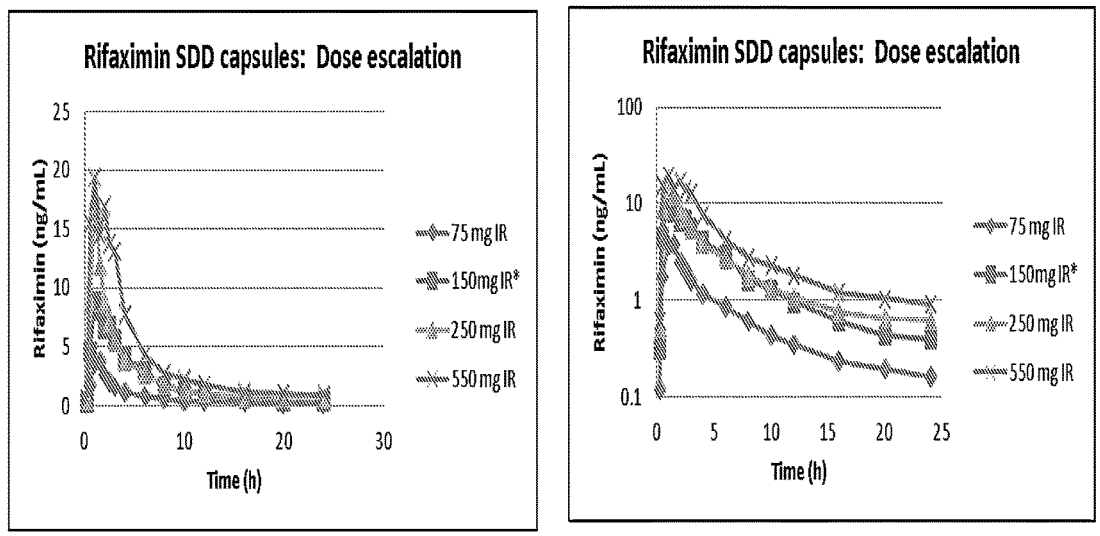
FIG. 85 depicts a summary of Rifaximin SDD dose escalation studies.

Described herein are clinical studies carried in ten male human subjects. FIG. 79 sets out the quotient study design for rifaximin SDD dose escalation. FIG. 80 outlines the dose escalation/regional absorption study, dose escalation/dose selection. FIGS. 81 and 82 show representative subject data from an exemplary dose escalation study. Mean data (linear scale and log scale) is shown in FIGS. 83 and 84, respectively. Mean profiles, log scale. Terminal phases are parallel, in clearance mechanisms. A summary of rifaximin SDD dose escalation is shown indicating that it is likely that there is not saturation of any metabolic or other systemic FIG. 85. To summarize, there are roughly dose proportional increases in exposure ($C_{max}$ and AUC) with increases in dose, as shown by $C_{max}$ multiple and AUC multiple columns $T_{max}$ is not delayed by dose increases, further indicating an early absorption window (corroborated by regional absorption data). The percent of dose in urine is remarkable in that it stays low, approximately 0.2% or less of the dose excreted over 24 h. This result is surprising in that this is quite low in spite of the significant increases in systemic exposure as compared with the crystalline formulation. Taken together, the results indicate a considerably increased solubility that presumably leads to increased local/lumenal soluble rifaximin, with accompanying increases in systemic exposure, but without significant increases in urinary excretion that are reflective of percent of rifaximin dose absorbed.

Dose/dosage form comparisons are shown in FIGS. 86 and 87. The tables compare SDD at increasing doses to the current crystalline formulation in terms of systemic PK. As noted in FIG. 87, as compared to the PK of rifaximin from the current formulation, the SDD formulation at the same dose shows an approximate 6.4-fold increase in $C_{max}$ and an approximate 8.9-fold increase in AUC. Nonetheless, these exposures are less than those observed in any hepatic impaired subject with the current tablet formulation.

Example 15

Exemplary Tablet Formulations

According to certain exemplary embodiments, microgranules, blends and tablets are formulated as set forth in Table 37, below

TABLE 37

| Rifaximin SDD Granules | | | | | |
|---|---|---|---|---|---|
| Component | Function | % w/w (0% CS) | % w/w (2.5% CS) | % w/w (5% CS) | % w/w (10% CSf) |
| Rifaximin | Drug | 47.2 | 46.02 | 44.84 | 42.48 |
| HPMC-AS | Polymer | 47.2 | 46.02 | 44.84 | 42.48 |
| Pluronic F-127 | Wetting agent | 5.6 | 5.46 | 5.32 | 5.04 |
| Croscarmellose Na (CS) | Rate controlling | 0 | 2.5 | 5 | 10 |
| Total | | 100 | 100 | 100 | 100 |
| Granule Blend | | | | | |
| | | mg/Tab | mg/Tab | mg/Tab | mg/Tab |
| Roller Compacted Granules | Granules | 635.59 | 652.34 | 669.05 | 706.21 |
| Avicel PH102 | Filler | 166 | 149.18 | 132.52 | 95.38 |
| Croscarmellose Na (Extra-granuler) | Disintegrant | 42.5 | 42.5 | 42.5 | 42.5 |
| Cab-O-Sil | Glidant | 1.7 | 1.7 | 1.7 | 1.7 |
| Magnesium Stearate | Lubricant | 4.25 | 4.25 | 4.25 | 4.25 |
| Total | | 850.04 | 849.97 | 850.02 | 850.04 |
| Overall Rifaximin Tablet Composition | | | | | |
| Component | Function | % w/w (0% CS) | % w/w (2.5% CS) | % w/w (5% CS) | % w/w (10% CS) |
| Rifamixin | Drug | 35.29 | 35.32 | 35.29 | 35.29 |
| HPMC-AS | Polymer | 35.29 | 35.32 | 35.29 | 35.29 |
| Pluronic F-127 | Wetting agent | 4.19 | 4.19 | 4.19 | 4.19 |
| Croscarmellose Na (intra-granuler) | Rate controlling | 0.00 | 1.92 | 3.94 | 8.31 |

TABLE 37-continued

| | | | | | |
|---|---|---|---|---|---|
| Avicel PH102 | Filler | 19.53 | 17.55 | 15.59 | 11.22 |
| Croscarmellose Na (Extra-granuler) | Disintegrant | 5.00 | 5.00 | 5.00 | 5.00 |
| Cab-O-Sil | Glidant | 0.20 | 0.20 | 0.20 | 0.20 |
| Magnesium Stearate | Lubricant | 0.50 | 0.50 | 0.50 | 0.50 |
| | Total | 100 | 100 | 100 | 100 |

What is claimed is:

1. A solid dispersion form of rifaximin, comprising rifaximin and one or more polymers selected from hydroxypropyl methylcellulose phthalate (HPMC-P), hydroxypropyl methylcellulose acetate succinate (HPMC-AS), polyvinylpyrrolidone, and a polymethacrylate, wherein the ratio of rifaximin to polymer is 25:75, 50:50, or 75:25 by weight, and wherein the solid dispersion form of rifaximin is characterized by an XRPD spectrum of one or more of the XRPD spectra of FIGS. 7, 12, 17, 22, 31 and 36.

2. A solid dispersion form of rifaximin, comprising rifaximin and one or more polymers selected from hydroxypropyl methylcellulose phthalate (HPMC-P), hydroxypropyl methylcellulose acetate succinate (HPMC-AS), polyvinylpyrrolidone, and a polymethacrylate, wherein the ratio of rifaximin to polymer is 25:75, 50:50, or 75:25 by weight, and wherein the solid dispersion form of rifaximin is characterized by a Thermogram of one or more of the Thermogram of FIGS. 8-11, 13-16, 18-21, 23-26, 27-30 and 32.

3. The solid dispersion form according to claim 1, wherein the solid dispersion form has the appearance of a single glass transition temperature (Tg).

4. The solid dispersion form according to claim 1, wherein a Tg of the solid dispersion form increases with an increased rifaximin concentration.

5. The solid dispersion form according to claim 1, wherein when the solid dispersion form is stressed at 70° C./75% RH for 1 week, solids are still x-ray amorphous according to XRPD.

6. The solid dispersion form according to claim 1, wherein when the solid dispersion form is stressed at 70° C./75% RH for 3 weeks, solids are still x-ray amorphous according to XRPD.

7. The solid dispersion form according to claim 1, wherein when the solid dispersion form is stressed at 70° C./75% RH for 6 weeks, solids are still x-ray amorphous according to XRPD.

8. The solid dispersion form according to claim 1, wherein when the solid dispersion form is stressed at 70° C./75% RH for 12 weeks, solids are still x-ray amorphous according to XRPD.

9. A pharmaceutical composition comprising the solid dispersion form of rifaximin of claim 1, a polymer, a surfactant, and a release controlling agent.

10. The pharmaceutical composition of claim 9, comprising the solid dispersion form of rifaximin, HPMC-AS, pluronic F127, and croscarmellose Na (CS).

11. The pharmaceutical composition of claim 9, wherein the pharmaceutical composition is a tablet or pill.

12. The pharmaceutical composition of claim 9, further comprising fillers, glidants or lubricants.

13. The solid dispersion form of rifaximin of claim 1, wherein the HPMC-AS is grade HG or MG.

14. The solid dispersion form dispersion of rifaximin of claim 1, wherein the HPMC-P is grade 55.

15. The solid dispersion form of rifaximin of claim 1, wherein the solid dispersion of rifaximin comprises a ternary dispersion.

\* \* \* \* \*